United States Patent
Zhu et al.

(10) Patent No.: US 6,406,863 B1
(45) Date of Patent: Jun. 18, 2002

(54) HIGH THROUGHPUT GENERATION AND SCREENING OF FULLY HUMAN ANTIBODY REPERTOIRE IN YEAST

(75) Inventors: Li Zhu, Palo Alto; Shaobing Benjamin Hua, Cupertino, both of CA (US)

(73) Assignee: GeneTastix Corporation, San Jose, CA (US)

( * ) Notice: Subject to any disclaimer, the term of this patent is extended or adjusted under 35 U.S.C. 154(b) by 0 days.

(21) Appl. No.: 09/603,663

(22) Filed: Jun. 23, 2000

(51) Int. Cl.$^7$ .......................... G01N 33/53; C12Q 1/02; C12P 21/04

(52) U.S. Cl. .......................... 435/7.1; 435/7.8; 435/29; 435/69.7; 435/71.1

(58) Field of Search .......................... 435/7.1, 7.8, 29, 435/69.7, 71.1

(56) References Cited

U.S. PATENT DOCUMENTS

| | | | |
|---|---|---|---|
| 5,811,238 A | 9/1998 | Stemmer et al. | 435/6 |
| 5,869,250 A | 2/1999 | Cheng et al. | 435/6 |
| 5,888,773 A | 3/1999 | Jost et al. | 435/69.6 |
| 5,922,545 A | 7/1999 | Mattheakis et al. | 435/6 |
| 5,928,868 A | 7/1999 | Liu et al. | 435/6 |
| 5,962,255 A | 10/1999 | Griffiths et al. | 435/69.1 |
| 6,057,101 A * | 5/2000 | Nandabalan et al. | 435/6 |
| 6,072,036 A | 6/2000 | Marasco et al. | 530/387.3 |

FOREIGN PATENT DOCUMENTS

| | | | |
|---|---|---|---|
| WO | WO 99/28502 | * | 6/1999 |
| WO | WO 99/53049 | | 10/1999 |

OTHER PUBLICATIONS

Hua et al. (1998) Gene 215: 143–152.*
Gietz et al. (1995) Methods in Molecular and Cellular Biology 5 255–269.*
Terret, N.K. (1998) "Combinatorial Chemictry," Oxford University Press, pp.2–5.*
Fields et al., "A Novel Genetic System To Detect Protein–Protein Interactions", Letters to Nature, vol. 340; Jul. 20, 1989.
Finley R.L. et al., "Interaction Mating Reveals Binary and Ternary Connections Between Drosophila Cell Cycle Regulators", Proc. Natl. Acad. Sci, USA; vol. 91, pp. 12980–12984, Dec. 1994.
Ehlers, M.D., "Synapse Structure: Glutamate Receptors Connected By the Shanks"Current Biology, vol. 9, No. 22; 1999.
Lecrenier, N., et al. "Two–Hybrid Systematic Screening of the Yeast Proteome"Bioessays, vol. 20.1.
Fromont–Racine, M. et al., "Toward A Functional Analysis of the Yeast Genome Through Exhaustive Two–Hybrid Screens", Nature Genetics, vol. 16, Jul. 1997.

Cha, JH. et al., "Cell Surface Monkey CD9 Antigen Is a Coreceptor That Increases Diphtheria Toxin Sensitivity and Diphtheria Toxin Receptor Affinity", Journal of Biological Chemistry, vol. 275, No. 10; Mar. 10, 1999.
Shoji, H. et al., "Identification and Characterization of a PDZ Protein That Interacts With Activin Type II Receptors", Journal of Biological Chemistry, vol. 275, No. 8; Feb. 15, 1999.
Puga, A. et al., "Aromatic Hydrocarbon Receptor Interaction With the Retinoblastoma Protein Potentiates Repression of E2F–Dependant Transcription and Cell Cycle Arrest", Journal of Biological Chemistry, vol. 275, No. 4; Jan. 28, 2000.
Lezcano, N. et al., "Dual Signaling Regulated By Calcyon, a D1 Dopamine Receptor Interacting Protein" Science Magazine, vol. 287; Mar. 3, 2000.
Garcia, R.A.G. et al., "The Neuregulin Receptor ErbB–4 Interacts With PDZ–containing Proteins at Neuronal Synapses", National Institute of Health, vol. 97, No. 7; Mar. 28, 2000.
BioTechniques; "Purification And Application of a Single–Chain Fv Antibody Fragment Specific to Hepititis B Virus Surface Antigen", Biotech Net, short technical report; vol. 19, No. 4; 1995.
Mimran, A. et al., "GCN4–Based Expression System (pGES): Transationally Regulated Yeast Expression Vectors", Biotechniques, research report; vol. 28, No. 3; 2000.
Castelli, L.A. et al.; "High–Level Secretion of Correctily Processed B–Lactamase From *Saccharomyces Ceravisiae* Using A High–Copy–Number Secretion Vector", Biomolecular Research Institute, vol. 142, pp. 113–117; 1994.
Allen, J.B. et al., "Finding Prospective Partners In The Library: The Two–Hybrid System and Phage Display Find A Match", TIBS 20, reviews; Dec. 1995.

(List continued on next page.)

Primary Examiner—Padmashri Ponnaluri
Assistant Examiner—Tomas Friend
(74) Attorney, Agent, or Firm—David J. Weitz; Shirley Cheh; Wilson Sonsini Goodrich & Rosati

(57) ABSTRACT

Compostions, kits and methods are provided for generating highly diverse libraries of proteins such as antibodies via homologous recombination in vivo, and screening these libraries against protein, peptide and nucleic acid targets using a two-hybrid method in yeast. The method for screening a library of tester proteins against a target protein or peptide comprises: expressing a library of tester proteins in yeast cells, each tester protein being a fusion protein comprised of a first polypeptide subunit whose sequence varies within the library, a second polypeptide subunit whose sequence varies within the library independently of the first polypeptide, and a linker peptide which links the first and second polypeptide subunits; expressing one or more target fusion proteins in the yeast cells expressing the tester proteins, each of the target fusion proteins comprising a target peptide or protein; and selecting those yeast cells in which a reporter gene is expressed, the expression of the reporter gene being activated by binding of the tester fusion protein to the target fusion protein.

26 Claims, 14 Drawing Sheets

OTHER PUBLICATIONS

Couto, J.R. et al., "Designing Human Consensus Antibodies With Minimal Positional Templates", Cancer Research Fund of Contra Costa; pp. 5973–5977.

Tsurushita, N. et al., "Phage Display Vectors For In Vivo Recombination of Immunoglobin Heavy and Light Chain Genes To Make Large Combinatorial Libraries", Protein Design Labs, vol. 72, pp. 59–63; 1996.

Boder, E.T. et al., "Yeast Surface Display For Screening Combinatorial Polypeptide Libraries", Dept. of Chemical Engineering, vol. 15; Jun. 1997.

Kontermann, R.E. et al., "Intracellular and Cell Surface Displayed Single–Chain Diabodies", Journal of Immunological Methods, vol. 226, pp. 179–188; 1999.

Fan, Z et al., "Therapeutic Application of Anti–Growth Factor Receptor Antibodies", Current Opinion in Oncology, vol. 10, pp. 67–73; 1998.

Conf. Of Molecular Library Technologies at the Millenium, "Molecular Library Technologies at the Millenium", Meeting Report, Oct. 1999.

Portner–Taliana, A. et al., "In Vivo Selection of Single–Chain Antibodies Using A Yeast Two–Hybrid System", Journal of Immunological Methods, vol. 238, pp. 161–172; 2000.

Visintin, M. et al., "Selection of Antibodies For Intracellular Function Using A Two–Hybrid In Vivo System", Biochemistry, vol. 96, No. 21, pp. 11723–11728; Oct. 12, 1999.

Fusco, C. et al., "In Vivo Construction of cDNA Libraries For Use In the Yeast Two–Hybrid System", Yeast, vol. 15, pp. 715–720; 1999.

Oldenburd, K.R. et al., "Recombination–Mediated PCR–Directed Plasmid Construction In Vivo in Yeast", Nucleic Acids Research, vol. 25, No. 2; pp. 451–452; 1997.

Hua, SB et al., "Construction of A Modular Yeast Two–Hybrid cDNA Library From Human EST Clones For the Human Genome Protein Linkage Map", International Journal of Genes, vol. 215, pp. 143–152; 1998.

* cited by examiner

Selection of Clones Indicating
Positive Binding Between
the V1-V2 Protein and the Target DNA Selection of Clones Indicating
Positive Binding Between
the V1-V2 Protein and the Target Protein

SEQUENCE LISTING

<160> NUMBER OF SEQ ID NOS: 75

<210> SEQ ID NO 1
<211> LENGTH: 34
<212> TYPE: DNA
<213> ORGANISM: Artificial Sequence
<220> FEATURE:
<223> OTHER INFORMATION: Description of Artificial Sequence: LoxP WT

<400> SEQUENCE: 1
ataacttcgt ataatgtatg ctatacgaag ttat                    34

```
<210> SEQ ID NO 2
<211> LENGTH: 34
<212> TYPE: DNA
<213> ORGANISM: Artificial Sequence
<220> FEATURE:
<223> OTHER INFORMATION: Description of Artificial Sequence: LoxP511

<400> SEQUENCE: 2
ataacttcgt atagtataca ttatacgaag ttat                    34

<210> SEQ ID NO 3
<211> LENGTH: 34
<212> TYPE: DNA
<213> ORGANISM: Artificial Sequence
<220> FEATURE:
<223> OTHER INFORMATION: Description of Artificial Sequence: LoxC2

<400> SEQUENCE: 3
acaacttcgt ataatgtatg ctatacgaag ttat                    34

<210> SEQ ID NO 4
<211> LENGTH: 34
<212> TYPE: DNA
<213> ORGANISM: Artificial Sequence
<220> FEATURE:
<223> OTHER INFORMATION: Description of Artificial Sequence: loxP1

<400> SEQUENCE: 4
ataacttcgt ataatatatg ctatacgaag ttat                    34

<210> SEQ ID NO 5
<211> LENGTH: 34
<212> TYPE: DNA
<213> ORGANISM: Artificial Sequence
<220> FEATURE:
<223> OTHER INFORMATION: Description of Artificial Sequence: LoxP2

<400> SEQUENCE: 5
ataacttcgt atagcataca ttatacgaag ttat                    34

<210> SEQ ID NO 6
<211> LENGTH: 34
<212> TYPE: DNA
<213> ORGANISM: Artificial Sequence
<220> FEATURE:
<223> OTHER INFORMATION: Description of Artificial Sequence: LoxP3

<400> SEQUENCE: 6
ataacttcgt ataatgtata ctatacgaag ttat                    34

<210> SEQ ID NO 7
<211> LENGTH: 33
<212> TYPE: DNA
<213> ORGANISM: Artificial Sequence
<220> FEATURE:
<223> OTHER INFORMATION: Description of Artificial Sequence: LoxP4

<400> SEQUENCE: 7
ataacttcgt ataatataaa ctatacgaag tta                     33

<210> SEQ ID NO 8
<211> LENGTH: 34
<212> TYPE: DNA
<213> ORGANISM: Artificial Sequence
<220> FEATURE:
<223> OTHER INFORMATION: Description of Artificial Sequence: LoxP5
```

```
<400> SEQUENCE: 8
ataacttcgt ataatctaac ctatacgaag ttat                               34

<210> SEQ ID NO 9
<211> LENGTH: 34
<212> TYPE: DNA
<213> ORGANISM: Artificial Sequence
<220> FEATURE:
<223> OTHER INFORMATION: Description of Artificial Sequence: LoxP6

<400> SEQUENCE: 9
ataacttcgt ataacatagc ctatacgaag ttat                               34

<210> SEQ ID NO 10
<211> LENGTH: 34
<212> TYPE: DNA
<213> ORGANISM: Artificial Sequence
<220> FEATURE:
<223> OTHER INFORMATION: Description of Artificial Sequence: LoxP7

<400> SEQUENCE: 10
ataacttcgt ataacatacc ctatacgaag ttat                               34

<210> SEQ ID NO 11
<211> LENGTH: 34
<212> TYPE: DNA
<213> ORGANISM: Artificial Sequence
<220> FEATURE:
<223> OTHER INFORMATION: Description of Artificial Sequence: LoxP8

<400> SEQUENCE: 11
attacctcgt atagcataca ttatacgaag ttat                               34

<210> SEQ ID NO 12
<211> LENGTH: 34
<212> TYPE: DNA
<213> ORGANISM: Artificial Sequence
<220> FEATURE:
<223> OTHER INFORMATION: Description of Artificial Sequence: LoxP9

<400> SEQUENCE: 12
ataacttcgt atagcataca ttatatgaag ttat                               34

<210> SEQ ID NO 13
<211> LENGTH: 34
<212> TYPE: DNA
<213> ORGANISM: Artificial Sequence
<220> FEATURE:
<223> OTHER INFORMATION: Description of Artificial Sequence: LoxP10

<400> SEQUENCE: 13
attacctcgt atagcataca ttatatgaag ttat                               34

<210> SEQ ID NO 14
<211> LENGTH: 82
<212> TYPE: DNA
<213> ORGANISM: Artificial Sequence
<220> FEATURE:
<223> OTHER INFORMATION: Description of Artificial Sequence: PCR primer

<400> SEQUENCE: 14
accccaccaa acccaaaaaa agagatctgt atggcttacc catacgatgt tccagattac   60
caggtgcagc tgcaggagtc sg                                           82
```

<210> SEQ ID NO 15
<211> LENGTH: 81
<212> TYPE: DNA
<213> ORGANISM: Artificial Sequence
<220> FEATURE:
<223> OTHER INFORMATION: Description of Artificial Sequence: PCR primer

<400> SEQUENCE: 15
accccaccaa acccaaaaaa agagatctgt atggcttacc catacgatgt tccagattac    60
caggtacagc tgcagcagtc a                                              81

<210> SEQ ID NO 16
<211> LENGTH: 82
<212> TYPE: DNA
<213> ORGANISM: Artificial Sequence
<220> FEATURE:
<223> OTHER INFORMATION: Description of Artificial Sequence: PCR primer

<400> SEQUENCE: 16
accccaccaa acccaaaaaa agagatctgt atggcttacc catacgatgt tccagattac    60
caggtgcagc tacagcagtg gg                                             82

<210> SEQ ID NO 17
<211> LENGTH: 81
<212> TYPE: DNA
<213> ORGANISM: Artificial Sequence
<220> FEATURE:
<223> OTHER INFORMATION: Description of Artificial Sequence: PCR primer

<400> SEQUENCE: 17
accccaccaa acccaaaaaa agagatctgt atggcttacc catacgatgt tccagattac    60
gaggtgcagc tgktggagwc y                                              81

<210> SEQ ID NO 18
<211> LENGTH: 83
<212> TYPE: DNA
<213> ORGANISM: Artificial Sequence
<220> FEATURE:
<223> OTHER INFORMATION: Description of Artificial Sequence: PCR primer

<400> SEQUENCE: 18
accccaccaa acccaaaaaa agagatctgt atggcttacc catacgatgt tccagattac    60
caggtccagc tkgtrcagtc tgg                                            83

<210> SEQ ID NO 19
<211> LENGTH: 82
<212> TYPE: DNA
<213> ORGANISM: Artificial Sequence
<220> FEATURE:
<223> OTHER INFORMATION: Description of Artificial Sequence: PCR primer

<400> SEQUENCE: 19
accccaccaa acccaaaaaa agagatctgt atggcttacc catacgatgt tccagattac    60
cagrtcacct tgaaggagtc tg                                             82

<210> SEQ ID NO 20
<211> LENGTH: 83
<212> TYPE: DNA
<213> ORGANISM: Artificial Sequence
<220> FEATURE:
<223> OTHER INFORMATION: Description of Artificial Sequence: PCR primer

<400> SEQUENCE: 20

```
accccaccaa acccaaaaaa agagatctgt atggcttacc catacgatgt tccagattac      60
caggtgcagc tggtgsartc tgg                                              83

<210> SEQ ID NO 21
<211> LENGTH: 82
<212> TYPE: DNA
<213> ORGANISM: Artificial Sequence
<220> FEATURE:
<223> OTHER INFORMATION: Description of Artificial Sequence: PCR primer

<400> SEQUENCE: 21
actgcctcca ccaccgctgc cacctccgcc agatcctccg ccgcctgatc caccaccgcc      60
tgaggagacr gtgaccaggg tg                                               82

<210> SEQ ID NO 22
<211> LENGTH: 82
<212> TYPE: DNA
<213> ORGANISM: Artificial Sequence
<220> FEATURE:
<223> OTHER INFORMATION: Description of Artificial Sequence: PCR primer

<400> SEQUENCE: 22
actgcctcca ccaccgctgc cacctccgcc agatcctccg ccgcctgatc caccaccgcc      60
tgaggagacg gtgaccaggg tt                                               82

<210> SEQ ID NO 23
<211> LENGTH: 81
<212> TYPE: DNA
<213> ORGANISM: Artificial Sequence
<220> FEATURE:
<223> OTHER INFORMATION: Description of Artificial Sequence: PCR primer

<400> SEQUENCE: 23
actgcctcca ccaccgctgc cacctccgcc agatcctccg ccgcctgatc caccaccgcc      60
tgaagagacg gtgaccattg t                                                81

<210> SEQ ID NO 24
<211> LENGTH: 83
<212> TYPE: DNA
<213> ORGANISM: Artificial Sequence
<220> FEATURE:
<223> OTHER INFORMATION: Description of Artificial Sequence: PCR primer

<400> SEQUENCE: 24
actgcctcca ccaccgctgc cacctccgcc agatcctccg ccgcctgatc caccaccgcc      60
tgaggagacg gtgaccgtgg tcc                                              83

<210> SEQ ID NO 25
<211> LENGTH: 80
<212> TYPE: DNA
<213> ORGANISM: Artificial Sequence
<220> FEATURE:
<223> OTHER INFORMATION: Description of Artificial Sequence: PCR primer

<400> SEQUENCE: 25
actgcctcca ccaccgctgc cacctccgcc agatcctccg ccgcctgatc caccaccgcc      60
ggttggggcg gatgcactcc                                                  80

<210> SEQ ID NO 26
<211> LENGTH: 81
<212> TYPE: DNA
```

<213> ORGANISM: Artificial Sequence
<220> FEATURE:
<223> OTHER INFORMATION: Description of Artificial Sequence: PCR primer

<400> SEQUENCE: 26
actgcctcca ccaccgctgc cacctccgcc agatcctccg ccgcctgatc caccaccgcc    60
sgatgggccc ttggtggarg c                                             81

<210> SEQ ID NO 27
<211> LENGTH: 83
<212> TYPE: DNA
<213> ORGANISM: Artificial Sequence
<220> FEATURE:
<223> OTHER INFORMATION: Description of Artificial Sequence: PCR primer

<400> SEQUENCE: 27
ggcggtggtg gatcaggcgg cggaggatct ggcggaggtg gcagcggtgg tggaggcagt    60
cagtctgtsb tgacgcagcc gcc                                           83

<210> SEQ ID NO 28
<211> LENGTH: 82
<212> TYPE: DNA
<213> ORGANISM: Artificial Sequence
<220> FEATURE:
<223> OTHER INFORMATION: Description of Artificial Sequence: PCR primer

<400> SEQUENCE: 28
ggcggtggtg gatcaggcgg cggaggatct ggcggaggtg gcagcggtgg tggaggcagt    60
tcctatgwgc tgacwcagcc ac                                            82

<210> SEQ ID NO 29
<211> LENGTH: 83
<212> TYPE: DNA
<213> ORGANISM: Artificial Sequence
<220> FEATURE:
<223> OTHER INFORMATION: Description of Artificial Sequence: PCR primer

<400> SEQUENCE: 29
ggcggtggtg gatcaggcgg cggaggatct ggcggaggtg gcagcggtgg tggaggcagt    60
tcctatgagc tgayrcagcy acc                                           83

<210> SEQ ID NO 30
<211> LENGTH: 80
<212> TYPE: DNA
<213> ORGANISM: Artificial Sequence
<220> FEATURE:
<223> OTHER INFORMATION: Description of Artificial Sequence: PCR primer

<400> SEQUENCE: 30
ggcggtggtg gatcaggcgg cggaggatct ggcggaggtg gcagcggtgg tggaggcagt    60
cagcctgtgc tgactcaryc                                               80

<210> SEQ ID NO 31
<211> LENGTH: 83
<212> TYPE: DNA
<213> ORGANISM: Artificial Sequence
<220> FEATURE:
<223> OTHER INFORMATION: Description of Artificial Sequence: PCR primer

<400> SEQUENCE: 31
ggcggtggtg gatcaggcgg cggaggatct ggcggaggtg gcagcggtgg tggaggcagt    60
cagdctgtgg tgacycagga gcc                                           83

<210> SEQ ID NO 32
<211> LENGTH: 83
<212> TYPE: DNA
<213> ORGANISM: Artificial Sequence
<220> FEATURE:
<223> OTHER INFORMATION: Description of Artificial Sequence: PCR primer

<400> SEQUENCE: 32
ggcggtggtg gatcaggcgg cggaggatct ggcggaggtg gcagcggtgg tggaggcagt    60
cagccwgkgc tgactcagcc mcc                                           83

<210> SEQ ID NO 33
<211> LENGTH: 83
<212> TYPE: DNA
<213> ORGANISM: Artificial Sequence
<220> FEATURE:
<223> OTHER INFORMATION: Description of Artificial Sequence: PCR primer

<400> SEQUENCE: 33
ggcggtggtg gatcaggcgg cggaggatct ggcggaggtg gcagcggtgg tggaggcagt    60
tcctctgagc tgastcagga scc                                           83

<210> SEQ ID NO 34
<211> LENGTH: 81
<212> TYPE: DNA
<213> ORGANISM: Artificial Sequence
<220> FEATURE:
<223> OTHER INFORMATION: Description of Artificial Sequence: PCR primer

<400> SEQUENCE: 34
ggcggtggtg gatcaggcgg cggaggatct ggcggaggtg gcagcggtgg tggaggcagt    60
cagtctgyyc tgaytcagcc t                                             81

<210> SEQ ID NO 35
<211> LENGTH: 82
<212> TYPE: DNA
<213> ORGANISM: Artificial Sequence
<220> FEATURE:
<223> OTHER INFORMATION: Description of Artificial Sequence: PCR primer

<400> SEQUENCE: 35
ggcggtggtg gatcaggcgg cggaggatct ggcggaggtg gcagcggtgg tggaggcagt    60
aattttatgc tgactcagcc cc                                            82

<210> SEQ ID NO 36
<211> LENGTH: 80
<212> TYPE: DNA
<213> ORGANISM: Artificial Sequence
<220> FEATURE:
<223> OTHER INFORMATION: Description of Artificial Sequence: PCR primer

<400> SEQUENCE: 36
gagatggtgc acgatgcaca gttgaagtga acttgcgggg tttttcagta tctacgattc    60
taggacggts ascttggtcc                                               80

<210> SEQ ID NO 37
<211> LENGTH: 80
<212> TYPE: DNA
<213> ORGANISM: Artificial Sequence
<220> FEATURE:
<223> OTHER INFORMATION: Description of Artificial Sequence: PCR primer

```
<400> SEQUENCE: 37
gagatggtgc acgatgcaca gttgaagtga acttgcgggg ttttcagta tctacgattc      60 gaggacggtc agctgggtgc                                                  80

<210> SEQ ID NO 38
<211> LENGTH: 83
<212> TYPE: DNA
<213> ORGANISM: Artificial Sequence
<220> FEATURE:
<223> OTHER INFORMATION: Description of Artificial Sequence: PCR primer

<400> SEQUENCE: 38
ggcggtggtg gatcaggcgg cggaggatct ggcggaggtg gcagcggtgg tggaggcagt      60
gacatccrgd tgacccagtc tcc                                              83

<210> SEQ ID NO 39
<211> LENGTH: 83
<212> TYPE: DNA
<213> ORGANISM: Artificial Sequence
<220> FEATURE:
<223> OTHER INFORMATION: Description of Artificial Sequence: PCR primer

<400> SEQUENCE: 39
ggcggtggtg gatcaggcgg cggaggatct ggcggaggtg gcagcggtgg tggaggcagt      60
gaaattgtrw tgacrcagtc tcc                                              83

<210> SEQ ID NO 40
<211> LENGTH: 83
<212> TYPE: DNA
<213> ORGANISM: Artificial Sequence
<220> FEATURE:
<223> OTHER INFORMATION: Description of Artificial Sequence: PCR primer

<400> SEQUENCE: 40
ggcggtggtg gatcaggcgg cggaggatct ggcggaggtg gcagcggtgg tggaggcagt      60
gatattgtgm tgacbcagwc tcc                                              83

<210> SEQ ID NO 41
<211> LENGTH: 82
<212> TYPE: DNA
<213> ORGANISM: Artificial Sequence
<220> FEATURE:
<223> OTHER INFORMATION: Description of Artificial Sequence: PCR primer

<400> SEQUENCE: 41
ggcggtggtg gatcaggcgg cggaggatct ggcggaggtg gcagcggtgg tggaggcagt      60
gaaacgacac tcacgcagtc tc                                               82

<210> SEQ ID NO 42
<211> LENGTH: 80
<212> TYPE: DNA
<213> ORGANISM: Artificial Sequence
<220> FEATURE:
<223> OTHER INFORMATION: Description of Artificial Sequence: PCR primer

<400> SEQUENCE: 42
gagatggtgc acgatgcaca gttgaagtga acttgcgggg ttttcagta tctacgattc      60 tttgatttcc accttggtcc                                                  80

<210> SEQ ID NO 43
<211> LENGTH: 80
```

<212> TYPE: DNA
<213> ORGANISM: Artificial Sequence
<220> FEATURE:
<223> OTHER INFORMATION: Description of Artificial Sequence: PCR primer

<400> SEQUENCE: 43
gagatggtgc acgatgcaca gttgaagtga acttgcgggg tttttcagta tctacgattc    60
tttgatctcc ascttggtcc                                                80

<210> SEQ ID NO 44
<211> LENGTH: 80
<212> TYPE: DNA
<213> ORGANISM: Artificial Sequence
<220> FEATURE:
<223> OTHER INFORMATION: Description of Artificial Sequence: PCR primer

<400> SEQUENCE: 44
gagatggtgc acgatgcaca gttgaagtga acttgcgggg tttttcagta tctacgattc    60
tttgatatcc actttggtcc                                                80

<210> SEQ ID NO 45
<211> LENGTH: 80
<212> TYPE: DNA
<213> ORGANISM: Artificial Sequence
<220> FEATURE:
<223> OTHER INFORMATION: Description of Artificial Sequence: PCR primer

<400> SEQUENCE: 45
gagatggtgc acgatgcaca gttgaagtga acttgcgggg tttttcagta tctacgattc    60
tttaatctcc agtcgtgtcc                                                80

<210> SEQ ID NO 46
<211> LENGTH: 78
<212> TYPE: DNA
<213> ORGANISM: Artificial Sequence
<220> FEATURE:
<223> OTHER INFORMATION: Description of Artificial Sequence: PCR primer

<400> SEQUENCE: 46
tcgaggcggt ggtggatcag gcggcggagg atctggcgga ggtggcagcg gtggtggagg    60
cagtgcgcgc ttaattaa                                                  78

<210> SEQ ID NO 47
<211> LENGTH: 78
<212> TYPE: DNA
<213> ORGANISM: Artificial Sequence
<220> FEATURE:
<223> OTHER INFORMATION: Description of Artificial Sequence: PCR primer

<400> SEQUENCE: 47
tcgattaatt aagcgcgcac tgcctccacc accgctgcca cctccgccag atcctccgcc    60
gcctgatcca ccaccgcc                                                  78

<210> SEQ ID NO 48
<211> LENGTH: 85
<212> TYPE: DNA
<213> ORGANISM: Artificial Sequence
<220> FEATURE:
<223> OTHER INFORMATION: Description of Artificial Sequence: PCR primer

<400> SEQUENCE: 48
actgcctcca cctgataact tcgtatagca tatattatac gaagttattg atccaccacc    60

```
gcctgaggag acrgtgacca gggtg                                            85

<210> SEQ ID NO 49
<211> LENGTH: 85
<212> TYPE: DNA
<213> ORGANISM: Artificial Sequence
<220> FEATURE:
<223> OTHER INFORMATION: Description of Artificial Sequence: PCR primer

<400> SEQUENCE: 49
actgcctcca cctgataact tcgtatagca tatattatac gaagttattg atccaccacc     60
gcctgaggag acggtgacca gggtt                                            85

<210> SEQ ID NO 50
<211> LENGTH: 84
<212> TYPE: DNA
<213> ORGANISM: Artificial Sequence
<220> FEATURE:
<223> OTHER INFORMATION: Description of Artificial Sequence: PCR primer

<400> SEQUENCE: 50
actgcctcca cctgataact tcgtatagca tatattatac gaagttattg atccaccacc     60
gcctgaagag acggtgacca ttgt                                             84

<210> SEQ ID NO 51
<211> LENGTH: 86
<212> TYPE: DNA
<213> ORGANISM: Artificial Sequence
<220> FEATURE:
<223> OTHER INFORMATION: Description of Artificial Sequence: PCR primer

<400> SEQUENCE: 51
actgcctcca cctgataact tcgtatagca tatattatac gaagttattg atccaccacc     60
gcctgaggag acggtgaccg tggtcc                                           86

<210> SEQ ID NO 52
<211> LENGTH: 83
<212> TYPE: DNA
<213> ORGANISM: Artificial Sequence
<220> FEATURE:
<223> OTHER INFORMATION: Description of Artificial Sequence: PCR primer

<400> SEQUENCE: 52
actgcctcca cctgataact tcgtatagca tatattatac gaagttattg atccaccacc     60
gccggttggg gcggatgcac tcc                                              83

<210> SEQ ID NO 53
<211> LENGTH: 84
<212> TYPE: DNA
<213> ORGANISM: Artificial Sequence
<220> FEATURE:
<223> OTHER INFORMATION: Description of Artificial Sequence: PCR primer

<400> SEQUENCE: 53
actgcctcca cctgataact tcgtatagca tatattatac gaagttattg atccaccacc     60
gccsgatggg cccttggtgg argc                                             84

<210> SEQ ID NO 54
<211> LENGTH: 86
<212> TYPE: DNA
<213> ORGANISM: Artificial Sequence
<220> FEATURE:
<223> OTHER INFORMATION: Description of Artificial Sequence: PCR primer
```

<400> SEQUENCE: 54
ggcggtggtg gatcaataac ttcgtataat atatgctata cgaagttatc aggtggaggc    60
agtcagtctg tsbtgacgca gccgcc                                        86

<210> SEQ ID NO 55
<211> LENGTH: 85
<212> TYPE: DNA
<213> ORGANISM: Artificial Sequence
<220> FEATURE:
<223> OTHER INFORMATION: Description of Artificial Sequence: PCR primer

<400> SEQUENCE: 55
ggcggtggtg gatcaataac ttcgtataat atatgctata cgaagttatc aggtggaggc    60
agttcctatg wgctgacwca gccac                                         85

<210> SEQ ID NO 56
<211> LENGTH: 86
<212> TYPE: DNA
<213> ORGANISM: Artificial Sequence
<220> FEATURE:
<223> OTHER INFORMATION: Description of Artificial Sequence: PCR primer

<400> SEQUENCE: 56
ggcggtggtg gatcaataac ttcgtataat atatgctata cgaagttatc aggtggaggc    60
agttcctatg agctgayrca gcyacc                                        86

<210> SEQ ID NO 57
<211> LENGTH: 83
<212> TYPE: DNA
<213> ORGANISM: Artificial Sequence
<220> FEATURE:
<223> OTHER INFORMATION: Description of Artificial Sequence: PCR primer

<400> SEQUENCE: 57
ggcggtggtg gatcaataac ttcgtataat atatgctata cgaagttatc aggtggaggc    60
agtcagcctg tgctgactca ryc                                           83

<210> SEQ ID NO 58
<211> LENGTH: 86
<212> TYPE: DNA
<213> ORGANISM: Artificial Sequence
<220> FEATURE:
<223> OTHER INFORMATION: Description of Artificial Sequence: PCR primer

<400> SEQUENCE: 58
ggcggtggtg gatcaataac ttcgtataat atatgctata cgaagttatc aggtggaggc    60
agtcagdctg tggtgacyca ggagcc                                        86

<210> SEQ ID NO 59
<211> LENGTH: 86
<212> TYPE: DNA
<213> ORGANISM: Artificial Sequence
<220> FEATURE:
<223> OTHER INFORMATION: Description of Artificial Sequence: PCR primer

<400> SEQUENCE: 59
ggcggtggtg gatcaataac ttcgtataat atatgctata cgaagttatc aggtggaggc    60
agtcagccwg kgctgactca gccmcc                                        86

<210> SEQ ID NO 60

<210> SEQ ID NO 60
<211> LENGTH: 86
<212> TYPE: DNA
<213> ORGANISM: Artificial Sequence
<220> FEATURE:
<223> OTHER INFORMATION: Description of Artificial Sequence: PCR primer

<400> SEQUENCE: 60
ggcggtggtg gatcaataac ttcgtataat atatgctata cgaagttatc aggtggaggc    60
agttcctctg agctgastca ggascc    86

<210> SEQ ID NO 61
<211> LENGTH: 84
<212> TYPE: DNA
<213> ORGANISM: Artificial Sequence
<220> FEATURE:
<223> OTHER INFORMATION: Description of Artificial Sequence: PCR primer

<400> SEQUENCE: 61
ggcggtggtg gatcaataac ttcgtataat atatgctata cgaagttatc aggtggaggc    60
agtcagtctg yyctgaytca gcct    84

<210> SEQ ID NO 62
<211> LENGTH: 85
<212> TYPE: DNA
<213> ORGANISM: Artificial Sequence
<220> FEATURE:
<223> OTHER INFORMATION: Description of Artificial Sequence: PCR primer

<400> SEQUENCE: 62
ggcggtggtg gatcaataac ttcgtataat atatgctata cgaagttatc aggtggaggc    60
agtaatttta tgctgactca gcccc    85

<210> SEQ ID NO 63
<211> LENGTH: 50
<212> TYPE: DNA
<213> ORGANISM: Artificial Sequence
<220> FEATURE:
<223> OTHER INFORMATION: Description of Artificial Sequence: PCR primer

<400> SEQUENCE: 63
cttcgtataa tgtatgctat acgaagttat taggacggts ascttggtcc    50

<210> SEQ ID NO 64
<211> LENGTH: 50
<212> TYPE: DNA
<213> ORGANISM: Artificial Sequence
<220> FEATURE:
<223> OTHER INFORMATION: Description of Artificial Sequence: PCR primer

<400> SEQUENCE: 64
cttcgtataa tgtatgctat acgaagttat gaggacggtc agctgggtgc    50

<210> SEQ ID NO 65
<211> LENGTH: 86
<212> TYPE: DNA
<213> ORGANISM: Artificial Sequence
<220> FEATURE:
<223> OTHER INFORMATION: Description of Artificial Sequence: PCR primer

<400> SEQUENCE: 65
ggcggtggtg gatcaataac ttcgtataat atatgctata cgaagttatc aggtggaggc    60
agtgacatcc rgdtgaccca gtctcc    86

```
<210> SEQ ID NO 66
<211> LENGTH: 86
<212> TYPE: DNA
<213> ORGANISM: Artificial Sequence
<220> FEATURE:
<223> OTHER INFORMATION: Description of Artificial Sequence: PCR primer

<400> SEQUENCE: 66
ggcggtggtg gatcaataac ttcgtataat atatgctata cgaagttatc aggtggaggc      60
agtgaaattg trwtgacrca gtctcc                                          86

<210> SEQ ID NO 67
<211> LENGTH: 86
<212> TYPE: DNA
<213> ORGANISM: Artificial Sequence
<220> FEATURE:
<223> OTHER INFORMATION: Description of Artificial Sequence: PCR primer

<400> SEQUENCE: 67
ggcggtggtg gatcaataac ttcgtataat atatgctata cgaagttatc aggtggaggc      60
agtgatattg tgmtgacbca gwctcc                                          86

<210> SEQ ID NO 68
<211> LENGTH: 85
<212> TYPE: DNA
<213> ORGANISM: Artificial Sequence
<220> FEATURE:
<223> OTHER INFORMATION: Description of Artificial Sequence: PCR primer

<400> SEQUENCE: 68
ggcggtggtg gatcaataac ttcgtataat atatgctata cgaagttatc aggtggaggc      60
agtgaaacga cactcacgca gtctc                                           85

<210> SEQ ID NO 69
<211> LENGTH: 50
<212> TYPE: DNA
<213> ORGANISM: Artificial Sequence
<220> FEATURE:
<223> OTHER INFORMATION: Description of Artificial Sequence: PCR primer

<400> SEQUENCE: 69
cttcgtataa tgtatgctat acgaagttat tttgatttcc accttggtcc                50

<210> SEQ ID NO 70
<211> LENGTH: 50
<212> TYPE: DNA
<213> ORGANISM: Artificial Sequence
<220> FEATURE:
<223> OTHER INFORMATION: Description of Artificial Sequence: PCR primer

<400> SEQUENCE: 70
cttcgtataa tgtatgctat acgaagttat tttgatctcc ascttggtcc                50

<210> SEQ ID NO 71
<211> LENGTH: 50
<212> TYPE: DNA
<213> ORGANISM: Artificial Sequence
<220> FEATURE:
<223> OTHER INFORMATION: Description of Artificial Sequence: PCR primer

<400> SEQUENCE: 71
cttcgtataa tgtatgctat acgaagttat tttgatatcc actttggtcc                50

<210> SEQ ID NO 72
```

```
<211> LENGTH: 50
<212> TYPE: DNA
<213> ORGANISM: Artificial Sequence
<220> FEATURE:
<223> OTHER INFORMATION: Description of Artificial Sequence: PCR primer

<400> SEQUENCE: 72
cttcgtataa tgtatgctat acgaagttat tttaatctcc agtcgtgtcc            50

<210> SEQ ID NO 73
<211> LENGTH: 78
<212> TYPE: DNA
<213> ORGANISM: Artificial Sequence
<220> FEATURE:
<223> OTHER INFORMATION: Description of Artificial Sequence: PCR primer

<400> SEQUENCE: 73
gagatggtgc acgatgcaca gttgaagtga acttgcgggg tttttcagta tctacgataa  60
cttcgtataa tgtatgct                                                78

<210> SEQ ID NO 74
<211> LENGTH: 63
<212> TYPE: DNA
<213> ORGANISM: Artificial Sequence
<220> FEATURE:
<223> OTHER INFORMATION: Description of Artificial Sequence: Suc 2
      signal

<400> SEQUENCE: 74
atgcttttgc aagctttcct tttccttttg gctggttttg cagccaaaat atctgcatca  60
atg                                                                63

<210> SEQ ID NO 75
<211> LENGTH: 20
<212> TYPE: PRT
<213> ORGANISM: Artificial Sequence
<220> FEATURE:
<223> OTHER INFORMATION: Description of Artificial Sequence: Linker
      peptide

<400> SEQUENCE: 75

Gly Gly Gly Gly Ser Gly Gly Gly Gly Ser Gly Gly Gly Gly Ser Gly
 1               5                  10                  15

Gly Gly Gly Ser
            20
```

HIGH THROUGHPUT GENERATION AND SCREENING OF FULLY HUMAN ANTIBODY REPERTOIRE IN YEAST

BACKGROUND OF THE INVENTION

1. Field of the Invention

This invention relates to compositions, methods and kits for generating libraries of recombinant expression vectors and using these libraries in screening of affinity-binding pairs, and, more particularly, for generating libraries of recombinant human antibodies and screening for their affinity binding with target antigens.

2. Description of Related Art

Antibodies are a diverse class of molecules. Delves, P. J. (1997) "Antibody production: essential techniques", New York, John Wiley & Sons, pp. 90–113. It is estimated that even in the absence of antigen stimulation a human makes at least $10^{15}$ different antibody molecules—its Permian antibody repertoire. The antigen-binding sites of many antibodies can cross-react with a variety of related but different antigenic determinants, and the Permian repertoire is apparently large enough to ensure that there will be an antigen-binding site to fit almost any potential antigenic determinant, albeit with low affinity.

Structurally, antibodies or immunoglobulins (Igs) are composed of one or more Y-shaped units. For example, immunoglobulin G (IgG) has a molecular weight of 150 kDa and consists of just one of these units. Typically, an antibody can be proteolytically cleaved by the proteinase papain into two identical Fab (fragment antigen binding) fragments and one Fc (fragment crystallizable) fragment. Each Fab contains one binding site for antigen, and the Fc portion of the antibodies mediates other aspects of the immune response.

A typical antibody contains four polypeptides-two identical copies of a heavy (H) chain and two copies of a light (L) chain, forming a general formula $H_2L_2$. Each L chain is attached to one H chain by a disulfide bond. The two H chains are also attached to each other by disulfide bonds. Papain cleaves N-terminal to the disulfide bonds that hold the H chains together. Each of the resulting Fabs consists of an entire L chain plus the N-terminal half of an H chain; the Fc is composed of the C-terminal halves of two H chains. Pepsin cleaves at numerous sites C-terminal to the inter-H disulfide bonds, resulting in the formation of a divalent fragment [F(ab')] and many small fragments of the Fc portion. IgG heavy chains contain one N-terminal variable ($V_H$) plus three C-terminal constant ($C_H1$, $C_H2$ and $C_H3$) regions. Light chains contain one N-terminal variable ($V_L$) and one C-terminal constant ($C_L$) region each. The different variable and constant regions of either heavy or light chains are of roughly equal length (about 110 amino residues per region). Fabs consist of one $V_L$, $V_H$, $C_H1$, and $C_L$ region each. The $V_L$ and $V_H$ portions contain hypervariable segments (complementarity-determining regions or CDR) that form the antibody combining site.

The $V_L$ and $V_H$ portions of a monoclonal antibody have also been linked by a synthetic linker to form a single chain protein (scFv) which retains the same specificity and affinity for the antigen as the monoclonal antibody itself. Bird, R. E., et al. (1988) "Single-chain antigen-binding proteins" Science 242:423–426. A typical scFv is a recombinant polypeptide composed of a $V_L$ tethered to a $V_H$ by a designed peptide, such as $(Gly_4\text{-}Ser)_3$, that links the carboxyl terminus of the $V_L$ to the amino terminus of the $V_H$ sequence. The construction of the DNA sequence encoding a scFv can be achieved by using a universal primer encoding the $(Gly_4\text{-}Ser)_3$ linker by polymerase chain reactions (PCR). Lake, D. F., et al. (1995) "Generation of diverse single-chain proteins using a universal $(Gly_4\text{-}Ser)_3$ encoding oligonucleotide" Biotechniques 19:700–702.

The mammalian immune system has evolved unique genetic mechanisms that enable it to generate an almost unlimited number of different light and heavy chains in a remarkably economical way by joining separate gene segments together before they are transcribed. For each type of Ig chain—κ light chains, λ light chains, and heavy chain—there is a separate pool of gene segments from which a single peptide chain is eventually synthesized. Each pool is on a different chromosome and usually contains a large number of gene segments encoding the V region of an Ig chain and a smaller number of gene segments encoding the C region. During B cell development a complete coding sequence for each of the two Ig chains to be synthesized is assembled by site-specific genetic recombination, bringing together the entire coding sequences for a V region and the coding sequence for a C region. In addition, the V region of a light chain is encoded by a DNA sequence assembled from two gene segments—a V gene segment and short joining or J gene segment. The V region of a heavy chain is encoded by a DNA sequence assembled from three gene segments—a V gene segment, a J gene segment and a diversity or D segment.

The large number of inherited V, J and D gene segments available for encoding Ig chains makes a substantial contribution on its own to antibody diversity, but the combinatorial joining of these segments greatly increases this contribution. Further, imprecise joining of gene segments and somatic mutations introduced during the V-D-J segment joining at the pre-B cell stage greatly increases the diversity of the V regions.

After immunization against an antigen, a mammal goes through a process known as affinity maturation to produce antibodies with higher affinity toward the antigen. Such antigen-driven somatic hypermutation fine-tunes antibody responses to a given antigen, presumably due to the accumulation of point mutations specifically in both heavy-and light-chain V region coding sequences and a selected expansion of high-affinity antibody-bearing B cell clones.

Great efforts have made to mimic such a natural maturation of antibodies against various antigens, especially antigens associated with diseases such as autoimmune diseases, cancer, AIDS and asthma. In particular, phage display technology has been used extensively to generate large libraries of antibody fragments by exploiting the capability of bacteriophage to express and display biologically functional protein molecule on the its surface. Combinatorial libraries of antibodies have been generated in bacteriophage lambda expression systems which may be screened as bacteriophage plaques or as colonies of lysogens (Huse et al. (1989) Science 246: 1275; Caton and Koprowski (1990) Proc. Natl. Acad. Sci. (U.S.A.) 87: 6450; Mullinax et al (1990) Proc. Natl. Acad. Sci. (U.S.A.) 87: 8095; Persson et al. (1991) Proc. Natl. Acad. Sci. (U.S.A.) 88: 2432). Various embodiments of bacteriophage antibody display libraries and lambda phage expression libraries have been described (Kang et al. (1991) Proc. Natl. Acad. Sci. (U.S.A.) 88: 4363; Clackson et al. (1991) Nature 352: 624; McCafferty et al. (1990) Nature 348: 552; Burton et al. (1991) Proc. Natl. Acad. Sci. (U.S.A.) 88: 10134; Hoogenboom et al. (1991) Nucleic Acids Res. 19: 4133; Chang et al. (1991) J. Immunol. 147: 3610; Breitling et al. (1991) Gene 104: 147; Marks et al. (1991) J. Mol. Biol. 222: 581; Barbas et al. (1992) Proc. Natl. Acad. Sci. (U.S.A.) 89: 4457; Hawkins and Winter (1992) J. Immunol. 22: 867; Marks et al. (1992) Biotechnology 10: 779; Marks et al. (1992) J. Biol. Chem. 267: 16007; Lowman et al (1991) Biochemistry 30: 10832; Lerner et al. (1992) Science 258: 1313). Also see review by Rader, C. and Barbas, C. F. (1997) "Phage display of combinatorial antibody libraries" Curr. Opin. Biotechnol. 8:503–508.

Various scFv libraries displayed on bacteriophage coat proteins have been described. Marks et al. (1992) Biotechnology 10: 779; Winter G and Milstein C (1991) Nature 349: 293; Clackson et al. (1991) op.cit.; Marks et al. (1991) J. Mol. Biol. 222: 581; Chaudhary et al. (1990) Proc. Natl. Acad. Sci. (USA) 87: 1066; Chiswell et al. (1992) TIBTECH 10: 80; and Huston et al. (1988) Proc. Natl. Acad. Sci. (USA) 85: 5879.

Generally, a phage library is created by inserting a library of a random oligonucleotide or a cDNA library encoding antibody fragment such as $V_L$ and $V_H$ into gene 3 of M13 or fd phage. Each inserted gene is expressed at the N-terminal of the gene 3 product, a minor coat protein of the phage. As a result, peptide libraries that contain diverse peptides can be constructed. The phage library is then affinity screened against immobilized target molecule of interest, such as an antigen, and specifically bound phages are recovered and amplified by infection into *Escherichia coli* host cells. Typically, the target molecule of interest such as a receptor (e.g., polypeptide, carbohydrate, glycoprotein, nucleic acid) is immobilized by covalent linkage to a chromatography resin to enrich for reactive phage by affinity chromatography) and/or labeled for screen plaques or colony lifts. This procedure is called biopanning. Finally, amplified phages can be sequenced for deduction of the specific peptide sequences. During the inherent nature of phage display, the antibodies displayed on the surface of the phage may not adopt its native conformation under such in vitro selection conditions as in a mammalian system. In addition, bacteria do not readily process, assemble, or express/secrete functional antibodies.

Transgenic animals such as mice have been used to generate fully human antibodies by using the XENOMOUSE™ technology developed by companies such as Abgenix, Inc., Fremont, Calif. and Medarex, Inc. Annandale, N.J. Strains of mice are engineered by suppressing mouse antibody gene expression and functionally replacing it with human antibody gene expression. This technology utilizes the natural power of the mouse immune system in surveillance and affinity maturation to produce a broad repertoire of high affinity antibodies. However, the breeding of such strains of transgenic mice and selection of high affinity antibodies can take a long period of time. Further, the antigen against which the pool of the human antibody is selected has to be recognized by the mouse as a foreign antigen in order to mount immune response; antibodies against a target antigen that does not have immunogenicity in a mouse may not be able selected by using this technology. In addition, there may be a regulatory issue regarding the use of transgenic animals, such as transgenic goats (developed by Genzyme Transgenics, Framingham, Mass.) and chickens (developed by Geneworks, Inc., Ann Arbor, Mich.), to produce antibody, as well as safety issues concerning containment of transgenic animals infected with recombinant viral vectors.

Antibodies and antibody fragments have also been produced in transgenic plants. Plants, such as corn plants (developed by Integrated Protein Technologies, St. Louis, Mo.), are transformed with vectors carrying antibody genes, which results in stable integration of these foreign genes into the plant genome. In comparison, most microorganisms transformed with plasmids can lose the plasmids during a prolonged fermentation. Transgenenic plant may be used as a cheaper means to produce antibody in large scales. However, due to the long growth circles of plants screening for antibody with high binding affinity toward a target antigen may not be efficient and feasible for high throughput screening in plants.

SUMMARY OF THE INVENTION

The present invention compositions, methods and kits for efficiently generating and screening for protein-protein or protein DNA binding pairs in vivo. The production and screening of the binding pairs can be adopted for high throughput screening in vivo.

In one aspect of the present invention, compositions are provided. These compositions may be used for screening affinity binding pairs between a tester protein and a target molecule including protein, peptide, DNA, RNA, and small molecules in vitro or in vivo.

In one embodiment, a library of yeast expression vectors is provided. The yeast expression vectors forming in the library comprise a first nucleotide sequence encoding a first polypeptide subunit; a second nucleotide sequence encoding a second polypeptide subunit; and a linker sequence encoding a linker peptide that links the first nucleotide sequence and the second nucleotide sequence. The first polypeptide subunit, the second polypeptide subunit, and the linker polypeptide are expressed as a single fusion protein. In addition, the first and second nucleotide sequence each independently varies within the library of expression vectors.

According to the embodiment, the yeast expression vector may be a $2\mu$ plasmid vector, preferably a yeast-bacterial shuttle vector which contains a bacterial origin of replication.

In another embodiment, a library of expression vectors is provided. The expression vectors forming in the library comprise: a transcription sequence encoding an activation domain or a DNA binding domain of a transcription activator; a first nucleotide sequence encoding a first polypeptide subunit; a second nucleotide sequence encoding a second polypeptide subunit; and a linker sequence encoding a linker peptide that links the first nucleotide sequence and the second nucleotide sequence. The activation domain or the DNA binding domain of the transcription activator, the first polypeptide subunit, the second polypeptide subunit, and the linker polypeptide are expressed as a single fusion protein. In addition, the first and second nucleotide sequences each independently varies within the library of expression vectors.

According to this embodiment, the expression vector may be a bacterial, phage, yeast, mammalian and viral expression vector, preferably a yeast expression vector, and more preferably a $2\mu$ plasmid yeast expression vector.

Also according to this embodiment, the transcription activator sequence may be located 5' relative to the first nucleotide sequence, the linker sequence, and the second nucleotide sequence. Alternatively, the transcription activator sequence may be located 3' relative to the first nucleotide sequence, the linker sequence, and the second nucleotide sequence.

In yet another embodiment, a library of transformed yeast cells is provided. The library of yeast cells comprises a library of yeast expression vectors. The expression vectors in the library of transformed yeast cells comprise: a transcription sequence encoding an activation domain or a DNA binding domain of a transcription activator; a first nucleotide sequence encoding a first polypeptide subunit; a second nucleotide sequence encoding a second polypeptide subunit; and a linker sequence encoding a linker peptide that links the first nucleotide sequence and the second nucleotide sequence. The activation domain or the DNA binding domain of the transcription activator, the first polypeptide subunit, the second polypeptide subunit, and the linker polypeptide are expressed as a single fusion protein. In addition, the first and second nucleotide sequences each independently varies within the library of expression vectors.

According to this embodiment, the yeast cells may be diploid yeast cells. Alternatively, the yeast cells may be haploids such as the a and a strain of yeast haploid cells.

In another aspect of the present invention, methods are provided for generating a library of yeast expression vectors that may be used for screening protein-protein or protein-DNA binding pairs.

In one embodiment, the method comprises: transforming into yeast cells a linearized yeast expression vector having a 5'- and 3'-terminus sequence at the site of linearization and a library of insert nucleotide sequences that are linear and double-stranded. The insert sequences comprise a first nucleotide sequence encoding a first polypeptide subunit, a second nucleotide sequence encoding a second polypeptide subunit, and a linker sequence encoding a linker peptide that links the first and second polypeptide subunits. Each of the insert sequences also comprises a 5'- and 3'-flanking sequence at the ends of the insert sequence. The 5'- and 3'-flanking sequence of the insert sequence are sufficiently homologous to the 5'- and 3'-terminus sequences of the linearized yeast expression vector, respectively, to enable homologous recombination to occur. The homologous recombination occurring between the vector and the insert sequence results in inclusion of the insert sequence into the vector in the transformed yeast cells.

In this embodiment, the first polypeptide subunit, the second polypeptide subunit, and the linker polypeptide are expressed as a single fusion protein. Also, the first and second nucleotide sequences each independently varies within the library of expression vectors.

According to the embodiment, the 5'- or 3'-flanking sequence of the insert nucleotide sequence may be preferably between about 30–120 bp in length, more preferably between about 40–90 bp in length, and most preferably between about 60–80 bp in length.

In another embodiment, a method is provided for generating a library of yeast expression vectors. The method comprises:

a) transforming into yeast cells
  i) a linearized yeast expression vector having a 5'- and 3'-terminus sequence at a first site of linearization, and
  ii) a library of first insert nucleotide sequences that are linear, double stranded, each of the first insert sequences comprising a first nucleotide sequence encoding a first polypeptide subunit, a 5'- and 3'-flanking sequence at the ends of the first insert sequence which are sufficiently homologous to the 5'- and 3'-terminus sequences of the vector at the first site of linearization, respectively, to enable homologous recombination to occur;
b) having homologous recombination occur between the vector and the first insert sequence in the transformed yeast cells, such that the first insert sequence is included in the vector;
c) isolating from the transformed yeast cells the vectors that contain the library of the first insert sequences;
d) linearizing the vectors containing the library of the first insert sequences to generate a 5'- and 3'-terminus sequence at a second site of linearization;
e) transforming into the transformed yeast cells
  i) the linearized yeast expression vectors in step d), and
  ii) a library of second insert nucleotide sequences that are linear, double stranded, each of the second insert sequences comprising a second nucleotide sequence encoding a second polypeptide subunit, a 5'- and 3'-flanking sequence at the ends of the second insert sequence which are sufficiently homologous to the 5'- and 3'-terminus sequences of the vector at the second site of linearization, respectively, to enable homologous recombination to occur; and
f) having homologous recombination occur between the linearized yeast expression vector at the second linearization site and the second insert sequences in the transformed yeast cells, such that the second insert sequence is included in the vector and the first and second nucleotide sequences are linked by a linker sequence.

The expression vectors formed by this method express the first polypeptide subunit, the second polypeptide subunit, and the linker polypeptide as a single fusion protein. Also, the first and second nucleotide sequences each independently varies within the library of expression vectors formed by this method.

According to the embodiment, the 5'- or 3'-flanking sequence of the insert nucleotide sequence are preferably between about 30–120 bp in length, more preferably between about 40–90 bp in length, and most preferably between about 60–80 bp in length.

In a variation of the above-described method, the diversity of the library of expression vectors formed by this method may be increased by chain shuffling via site-specific recombination. Accordingly, the method may further comprise: causing site-specific recombination between the members of the library of the yeast expression vectors at the 5'- and 3'-recombination sites, the recombination resulting in exchange of the first or second nucleotide sequences between the members of the library of the yeast expression vectors.

According to this variation, the 5'- and 3'-flanking sequences at the ends of the first or second insert nucleotide sequence comprise a 5'- and 3'-recombination site, respectively, that are recognized by a site-specific recombinase.

Also according to the variation, the 5'- and 3'-site-specific recombination sites are preferably different site-specific recombination sites, more preferably sites which are each independently selected from the group consisting of SEQ ID Nos: 1–13, most preferably loxP of coliphase P1, and the other being a mutant loxP sequence.

Also according to this variation, the site-specific recombinase may be constitutively or inducibly expressed in the yeast cells. The site-specific recombinase may be CRE recombinase that cause the site-specific recombination.

In yet another aspect of the present invention, methods are provided for selecting tester proteins capable of binding to a target peptide, protein, or DNA.

In one embodiment where the target molecule is a target peptide or protein, the method comprise: expressing a library of tester proteins in yeast cells, each tester protein being a fusion protein comprised of a first polypeptide subunit whose sequence varies within the library, a second polypeptide subunit whose sequence varies within the library independently of the first polypeptide, and a linker peptide which links the first and second polypeptide subunits; expressing one or more target fusion proteins in the yeast cells expressing the tester proteins, each of the target fusion proteins comprising a target peptide or protein; and selecting those yeast cells in which a reporter gene is expressed, the expression of the reporter gene being activated by binding of the tester fusion protein to the target fusion protein.

According to this embodiment, expression of the reporter gene may be activated by a functional transcription activator being formed by the binding of the tester protein to the target peptide or protein as in a yeast two-hybrid system.

According, in a variation of the embodiment involving the yeast two-hybrid system, the step of expressing the library of tester fusion proteins may include transforming a library of tester expression vectors into the yeast cells which contain a reporter construct comprising the reporter gene whose expression is under transcriptional control of a transcription activator comprising an activation domain and a DNA binding domain. Each of the tester expression vectors comprises a first transcription sequence encoding either the activation domain or the DNA binding domain of the transcription activator, a first nucleotide sequence encoding the first polypeptide subunit, a second nucleotide sequence encoding the second polypeptide subunit, and a linker sequence encoding a linker peptide that links the first nucleotide sequence and the second nucleotide sequence. Optionally, the step of expressing the target fusion proteins includes transforming a target expression vector into the yeast cells simultaneously or sequentially with the library of tester expression vectors. The target expression vector comprises a second transcription sequence encoding either the activation domain or the DNA binding domain of the transcription activator which is not expressed by the library of tester expression vectors; and a target sequence encoding the target protein or peptide.

In another variation of the embodiment involving the yeast two-hybrid system, the steps of expressing the library of tester fusion proteins and expressing the target fusion protein includes causing mating between first and second populations of haploid yeast cells of opposite mating types. The first population of haploid yeast cells comprises a library of tester expression vectors for the library of tester fusion proteins. Each of the tester expression vector comprises a first transcription sequence encoding either the activation domain or the DNA binding domain of the transcription activator, a first nucleotide sequence encoding the first polypeptide subunit, a second nucleotide sequence encoding the second polypeptide subunit, and a linker sequence encoding a linker peptide that links the first nucleotide sequence and the second nucleotide sequence. The second population of haploid yeast cells comprises a target expression vector. The target expression vector comprises a second transcription sequence encoding either the activation domain or the DNA binding domain of the transcription activator which is not expressed by the library of tester expression vectors; and a target sequence encoding the target protein or peptide. Either the first or second population of haploid yeast cells comprises a reporter construct comprising the reporter gene whose expression is under transcriptional control of the transcription activator.

In this variation, the haploid yeast cells of opposite mating types may preferably be α and a type strains of yeast. The mating between the first and second populations of haploid yeast cells of α and a type strains may be conducted in a rich nutritional culture medium.

Optionally, a plurality of target fusion protein may be expressed and screened against the library of tester proteins at the same time. According to this variation, the steps of expressing the library of tester fusion proteins and expressing the plurality of the target fusion proteins include causing mating between first and second populations of haploid yeast cells of opposite mating types. The first population of haploid yeast cells comprises a library of tester expression vectors for the library of tester fusion proteins. Each of the tester expression vector comprises a first transcription sequence encoding either the activation domain or the DNA binding domain of the transcription activator, a first nucleotide sequence encoding the first polypeptide subunit, a second nucleotide sequence encoding the second polypeptide subunit, and a linker sequence encoding a linker peptide that links the first nucleotide sequence and the second nucleotide sequence. The second population of haploid yeast cells comprises a plurality of target expression vectors. The target expression vectors comprise a second transcription sequence encoding either the activation domain or the DNA binding domain of the transcription activator which is not expressed by the library of tester expression vectors; and a target sequence encoding the target protein or peptide. Either the first or second population of haploid yeast cells comprises a reporter construct comprising the reporter gene whose expression is under transcriptional control of the transcription activator.

According to this variation, the haploid yeast cells of opposite mating types may preferably be α and a type strains of yeast. The mating between the first and second populations of haploid yeast cells of α and a type strains may be conducted in a rich nutritional culture medium.

Also according to this variation, members of the library of tester expression vectors may be arrayed as individual yeast clones in one or more multiple-well plates.

Also according to this variation, the plurality of the target expression vectors may be arrayed as individual yeast clones in one or more multiple-well plates.

Also according to this variation, the mating may be based on clonal mating in which each yeast clone containing a members of the tester expression vectors is mated individually with each of the plurality of target expression vectors.

Also according to this variation, the plurality of the target expression vectors may be a library of expression vectors containing a collection of human EST clones or a collection of domain structures.

According to any of the above-described methods for selecting protein-protein binding pairs, the target fusion protein comprises an antigen associated with a disease state such as a tumor-surface antigen. Optionally, the target fusion protein may comprises a human growth factor receptor such as epidermal growth factors, transferrin, insulin-like growth factor, transforming growth factors, interleukin-1, and interleukin-2.

In another embodiment, a method is provided for screening protein-DNA binding pairs in a yeast one-hybrid system.

The method comprises: expressing a library of tester fusion proteins in yeast cells which contain a reporter construct comprising a reporter gene whose expression is under a transcriptional control of a target DNA sequence; and selecting the yeast cells in which the reporter gene is expressed, the expression of the reporter gene being activated by binding of the tester fusion protein to the target DNA sequence. Each of the tester fusion proteins comprises an activation domain of a transcription activator, a first polypeptide subunit whose sequence varies within the library, a second polypeptide subunit whose sequence varies within the library independently of the first polypeptide subunit, and a linker peptide that links the first polypeptide subunit to the second polypeptide subunit.

In a variation of the embodiment, the step of expressing the library of tester fusion proteins includes transforming into the yeast cells a library of tester expression vectors for the library of tester fusion proteins. Each of the tester expression vectors comprises a transcription sequence encoding the activation domain of the transcription activator, a first nucleotide sequence encoding the first polypeptide subunit, a second nucleotide sequence encoding the second polypeptide subunit, and a linker sequence encoding a linker peptide that links the first nucleotide sequence and the second nucleotide sequence.

In another variation of the embodiment, the step of expressing a library of tester fusion proteins in yeast cells includes causing mating between a first and second populations of haploid yeast cells of opposite mating types. The first population of haploid yeast cells comprises a library of tester expression vectors for the library of tester fusion proteins, each tester expression vector comprising a transcription sequence encoding the activation domain of the transcription activator, a first nucleotide sequence encoding the first polypeptide subunit, a second nucleotide sequence encoding the second polypeptide subunit, and a linker sequence encoding a linker peptide that links the first nucleotide sequence and the second nucleotide sequence. The second population of haploid yeast cells comprises the reporter construct.

According to the variation, the haploid yeast cells of opposite mating types may preferably be α and a type strains of yeast. The mating between the first and second populations of haploid yeast cells of α and a type strains is preferably conducted in a rich nutritional culture medium.

According to any of the above-described methods for selecting protein-DNA binding pairs, the target DNA sequence in the reporter construct is preferably positioned in 2–6 tandem repeats 5' relative to the reporter gene.

The target DNA sequence in the reporter construct is preferably between about 15–75 bp in length and more preferably between about 25–55 bp in length.

In yet another embodiment, a method is provided for screening protein-protein binding pairs in a yeast one-hybrid system. The method comprises: expressing a library of tester fusion proteins in yeast cells which contain a reporter construct comprising a reporter gene whose expression is under a transcriptional control of a specific DNA binding site; expressing a target protein in the yeast cells expressing the tester fusion proteins, where the target protein binds to the specific DNA binding site; and selecting the yeast cells in which the reporter gene is expressed, the expression of the reporter gene being activated by binding of the tester fusion protein to the target protein. Each of the tester fusion proteins comprises an activation domain of a transcription activator, a first polypeptide subunit, a second polypeptide subunit, and a linker peptide that links the first polypeptide subunit to the second polypeptide subunit, wherein the sequences of the first and second polypeptide subunits each independently varies within the library of the tester fusion protein.

In a variation of the embodiment, the step of expressing the library of tester fusion proteins includes transforming into the yeast cells a library of tester expression vectors for the library of tester fusion proteins. Each of the tester expression vectors comprises a transcription sequence encoding the activation domain of the transcription activator, a first nucleotide sequence encoding the first polypeptide subunit, a second nucleotide sequence encoding the second polypeptide subunit, and a linker sequence encoding a linker peptide that links the first nucleotide sequence and the second nucleotide sequence.

In another variation of the embodiment, the steps of expressing the library of tester fusion proteins and expressing the target fusion protein includes causing mating between a first and second populations of haploid yeast cells of opposite mating types. The first population of haploid yeast cells comprises a library of tester expression vectors for the library of tester fusion proteins. Each of the tester expression vectors comprises a transcription sequence encoding the activation domain of the transcription activator, a first nucleotide sequence encoding the first polypeptide subunit, a second nucleotide sequence encoding the second polypeptide subunit, and a linker sequence encoding a linker peptide that links the first nucleotide sequence and the second nucleotide sequence. The second population of haploid yeast cells comprises a target expression vector comprising a target sequence encoding the target protein. Either the first or second population of haploid yeast cells comprises the reporter construct.

In any of the above-described methods for selecting tester proteins capable of binding to a target peptide, protein, or DNA, the method may further comprise isolating the tester expression vectors from the selected yeast cells; and mutagenizing the first and second nucleotide sequences in the isolated tester expression vectors to form a library of mutagenized expression vectors.

Examples of mutagenesis methods include, but are not limited to, error-prone PCR mutagenesis, site-directed mutagenesis, DNA shuffling and combinations thereof. The library of mutagenized expression vectors may be screened against the same or different target peptide, protein or DNA by following similar procedures used for screening the tester expression vectors.

In yet another aspect of the present invention, methods are provided for producing a library of single chain antibodies. In an embodiment, the method comprises: expressing in yeast cells a library of yeast expression vectors. Each of the yeast expression vector comprises a first nucleotide sequence encoding an antibody heavy chain variable region, a second nucleotide sequence encoding an antibody light chain variable region, and a linker sequence encoding a linker peptide that links the antibody heavy chain variable region and the antibody light chain variable region. The antibody heavy chain variable region, the antibody light chain variable region, and the linker peptide are expressed as a single fusion protein. Also, the first and second nucleotide sequences each independently varies within the library of expression vectors to generate a library of single-chain antibodies with a diversity of at least $10^6$.

According to the embodiment, the diversity of the library of single-chain antibodies is preferably between $10^6$–$10^{16}$, more preferably between $10^8$–$10^{16}$, and most preferably between $10^{10}$–$10^{16}$.

In yet another aspect of the present invention, a kit is provided for selecting selecting tester proteins capable of binding to a target peptide, protein, or DNA.

In an embodiment, the kit comprises: a library of tester expression vectors and a yeast cell line. Each of the tester expression vectors comprises a first transcription sequence encoding either an activation domain or a DNA binding domain of a transcription activator, a first nucleotide sequence encoding a first polypeptide subunit, a second nucleotide sequence encoding a second polypeptide subunit, and a linker sequence encoding a linker peptide that links the first nucleotide sequence and the second nucleotide sequence. The first and second nucleotide sequences each independently varies within the library of expression vectors. A reporter construct may be contained in the yeast cell line. The reporter construct comprises a reporter gene whose expression is under a transcriptional control of a specific DNA binding site.

Optionally, the kit may further comprise a target expression vector which comprises a second transcription sequence encoding either the activation domain or the DNA binding domain of the transcription activator which is not expressed by the library of tester expression vectors; and a target sequence encoding the target protein or peptide.

In another embodiment, the kit comprises: a first and second populations of haploid yeast cells of opposite mating types. The first population of haploid yeast cells comprises a library of tester expression vectors for the library of tester fusion proteins. Each of the tester expression vector comprises a first transcription sequence encoding either an activation domain or a DNA binding domain of a transcription activator, a first nucleotide sequence encoding a first polypeptide subunit, a second nucleotide sequence encoding a second polypeptide subunit, and a linker sequence encoding a linker peptide that links the first nucleotide sequence and the second nucleotide sequence. The second population of haploid yeast cells comprises a target expression vector. The target expression vector encodes either the activation domain or the DNA binding domain of the transcription activator which is not expressed by the library of tester expression vectors; and a target sequence encoding the target protein or peptide. Either the first or second population of haploid yeast cells comprises a reporter construct comprising a reporter gene whose expression is under transcriptional control of the transcription activator.

Optionally, the second population of haploid yeast cells comprises a plurality of target expression vectors. Each of the target expression vectors encodes either the activation domain or the DNA binding domain of the transcription activator which is not expressed by the library of tester expression vectors; and a target sequence encoding the target protein or peptide. Either the first or second population of haploid yeast cells comprises a reporter construct comprising a reporter gene whose expression is under transcriptional control of the transcription activator.

According to any of the above-described compositions, methods and kits, the diversity of the first and/or the second polypeptide subunit encoded by the first and second nucleotide sequences within the library of expression vectors is preferably between $10^3$–$10^8$, more preferably between $10^4$–$10^8$, and most preferably between $10^5$–$10^8$.

Also according to any of the above-described compositions, methods and kits, the diversity of the fusion proteins encoded by the library of expression vectors may be preferably at least $10^6$–$10^{18}$, more preferably at least $10^9$–$10^{18}$, and most preferably at least $10^{10}$–$10^{18}$.

Also according to any of the above-described compositions, methods and kits, the diversities of the first and second polypeptide subunits may be each independently derived from libraries of precursor sequences that are not specifically designed for the target peptide or protein.

Also according to any of the above-described compositions, methods and kits, the diversities of the first and second polypeptide subunits optionally are not derived from one or more proteins that are known to bind to the target peptide or protein.

Also according to any of the above-described compositions, methods and kits, the diversities of the first and second polypeptide subunits optionally are not generated by mutagenizing one or more proteins that are known to bind to the target peptide or protein.

Also according to any of the above-described compositions, methods and kits, the first and the second polypeptide subunits may be subunits of a multimeric protein whose sequence varies within a library of multimeric proteins. Examples of multimeric proteins include, but are not limited to, growth factor receptors, T cell receptors, cytokine receptors, tyrosine kinase-associated receptors, and MHC proteins.

Also according to any of the above-described compositions, methods and kits, the first nucleotide sequence may be 5' relative to the second nucleotide sequence. The first nucleotide sequence in the library of expression vectors comprises a coding sequence of an antibody heavy-chain variable region, and the second nucleotide sequence comprises a coding sequence of an antibody light-chain variable region. The source of the coding sequences of the antibody light-chain and heavy-chain variable regions may be from human, non-human primate, or rodent. Optionally, the source of the coding sequences of the antibody light-chain and heavy-chain variable regions may be from one or more non-immunized animals. Preferably, the source of the coding sequences of the antibody light-chain and heavy-chain variable regions may be from human fetal spleen, lymph nodes or peripheral blood cells.

Also according to any of the above-described compositions, methods and kits, the linker peptides expressed by the library of expression vectors may provide a substantially conserved conformation between the first and second polypeptide subunits across the fusion proteins expressed by the library of expression vectors. This may be achieved by having the sequence of the linker peptides be substantially conserved across the library.

Also according to any of the above-described compositions, methods and kits, the conformation of the fusion protein having the first and second polypeptide subunits linked by the linker peptide may mimic a conformation of a single chain antibody. This may be achieved by selection of a linker peptide sequence comprising a Gly-Gly-Gly-Gly-Ser peptide in 3 or 4 tandem repeats.

Also according to any of the above-described compositions, methods and kits, the linker sequences in the library of expression vectors is preferably between 30–120 bp in length, more preferably between 45–102 bp in length, and most preferably between 45–63 bp in length. The linker sequences in the library of expression vectors may optionally comprise a nucleotide sequence encoding an amino acid sequence of Gly-Gly-Gly-Gly-Ser in 3 or 4 tandem repeats.

Also according to any of the above-described compositions, methods and kits, each of the expression vectors may further comprise a sequence encoding an affinity tag. Examples of affinity tags include, but are not limited to, polyhistidine tags, polyarginine tags, glutathione-S-transferase, maltose binding protein, staphylococcal protein A tag, and EE-epitope tags.

Also according to any of the above-described compositions, methods and kits, the transcription activator may be any transcription activator having separable DNA-binding and transcriptional activation domains. Examples of transcription activators include, but are not limited to, GAL4, GCN4, and ADR1 transcription activators.

Also according to any of the above-described compositions, methods and kits, the reporter protein encoded by the reporter gene may be any reporter gene, expression of which shows a distinct genotype or phenotype in a cell. Examples of such a reporter protein include, but are not limited to, β-galactosidase, α-galactosidase, luciferase, β-glucuronidase, chloramphenicol acetyl transferase, secreted embryonic alkaline phosphatase, green fluorescent protein, enhanced blue fluorescent protein, enhanced yellow fluorescent protein, and enhanced cyan fluorescent protein.

DETAILED DESCRIPTION OF THE INVENTION

Figure 1:
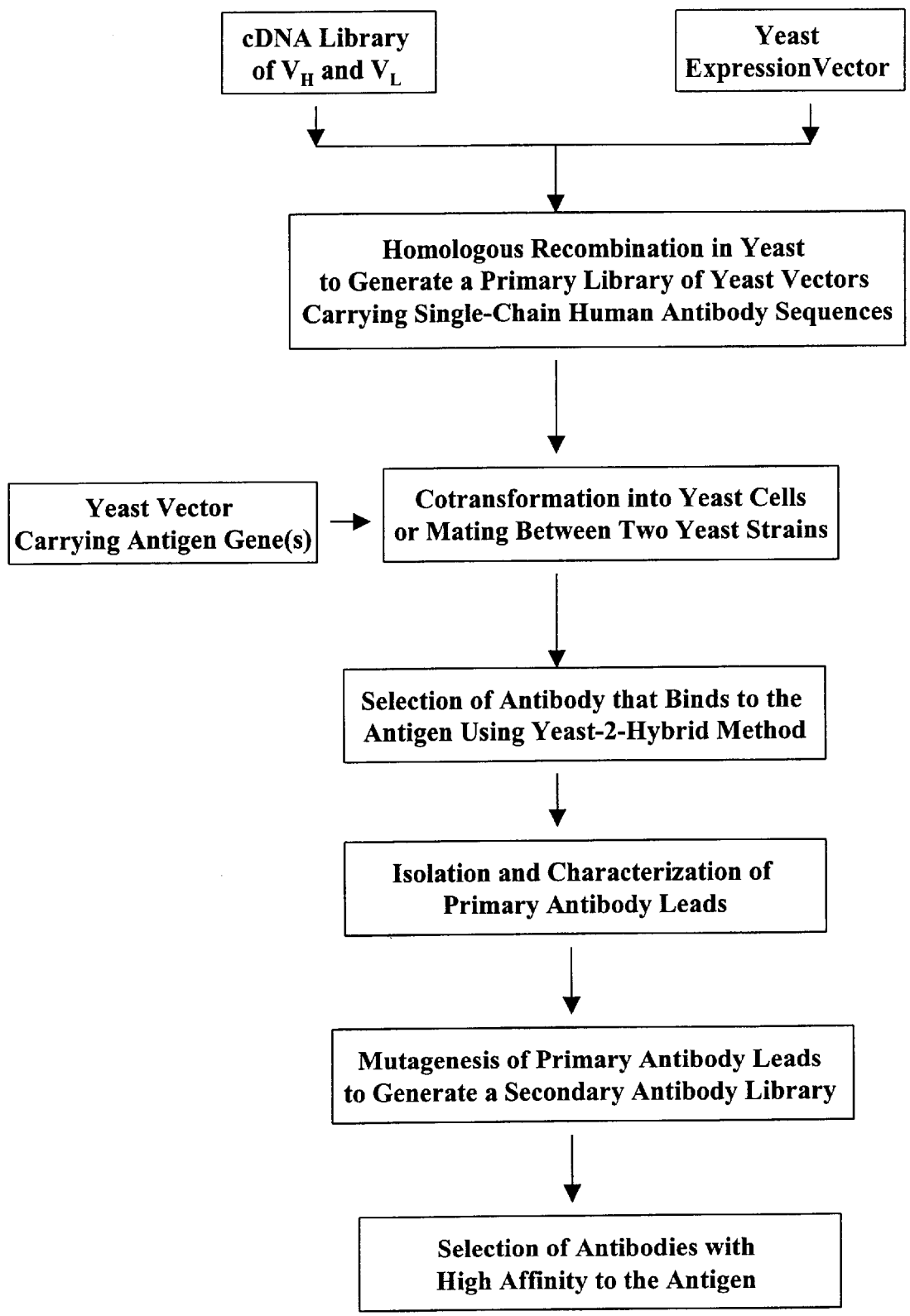
FIG. 1 illustrates a flow chart of a process that may be used in the present invention to screen for high affinity antibodies.

The present invention provides novel compositions, kits and efficient methods for preparing extremely diverse libraries of tester proteins, and selecting from these libraries proteins with high affinity and specificity toward a target protein, peptide or DNA in vivo. In one particular embodiment, highly diverse libraries of human antibodies can be produced and screened against virtually any target antigen by using the compositions, kits and methods of the present invention.

The present invention provides a general method for screening these diverse libraries of tester proteins against a single or a plurality of target proteins or peptides.

The method comprises: expressing a library of tester proteins in yeast cells, each tester protein being a fusion protein comprised of a first polypeptide subunit whose sequence varies within the library, a second polypeptide subunit whose sequence varies within the library independently of the first polypeptide, and a linker peptide which links the first and second polypeptide subunits; expressing one or more target fusion proteins in the yeast cells expressing the tester proteins, each of the target fusion proteins comprising a target peptide or protein; and selecting those yeast cells in which a reporter gene is expressed, the expression of the reporter gene being activated by binding of the tester fusion protein to the target fusion protein.

The library of tester proteins may be any multimeric proteins wherein the first and second polypeptide subunit are subunits of a multimeric protein whose sequence varies within the library of tester proteins.

In a preferred embodiment, the library of tester proteins is a library of antibodies where the first and second polypeptide subunits are an antibody heavy-chain variable region and an antibody light-chain variable region, respectively. The source of the coding sequences of the antibody light-chain and heavy-chain variable regions may be from humans, non-human primates, or rodents.

From these libraries of antibodies, antibodies with high affinity and specificity are selected by screening against the libraries single or a plurality of target antigens and antibodies, in particular, in yeast. Compared to conventional approaches of generating monoclonal antibody by hybridoma technology and the recently developed XENOMOUSE® technology, the present invention provides a more efficient and economical way to screen for fully human antibodies in a much shorter period of time. More importantly, the production and screening of the antibody libraries can be readily adopted for high throughput screening in vivo.

The library of tester proteins may be produced in vivo or in vitro by using any methods known in the art. The present invention provides a novel method for generating and screening libraries of expression vectors encoding these tester proteins against a single or a plurality of target molecules in vivo. These methods are developed by exploiting the intrinsic property of yeast—homologous recombination at an extremely high level of efficiency.

FIG. 1 shows a flow chart delineating a preferred embodiment of the above method of the present invention for generating and screening highly diverse libraries of single-chain human antibodies (scFv) in yeast. As illustrated in FIG. 1, a highly complex library of scFv is constructed in yeast cells. In particular, cDNA libraries of the heavy and light chain variable regions ($V_H$ and $V_L$) are transferred into a yeast expression vector by direct homologous recombination between the sequences encoding $V_H$ and $V_L$, and the yeast expression vector containing homologous recombination sites. The resulting expression vector is called scFv expression vector. This primary antibody library may reach a diversity preferably between $10^6$–$10^{12}$, more preferably between $10^7$–$10^{12}$, and most preferably between $10^8$–$10^{12}$.

The complexity of the primary antibody library generated in yeast can be further increased by "chain-shuffling" between the light or heavy chain sequences contained in the scFv expression vector via site-specific homologous recombination, such as CRE/loxP recombination. This antibody library may reach a complexity of $10^{18}$ after mutagenesis of the scFv sequences in the primary antibody library by exchanging the $V_H$ or $V_L$ sequences between two scFv vectors. Hence, the diversity of the resulting antibody library may preferably be between $10^9$–$10^{18}$, more preferably between $10^{10}$–$10^{18}$, and most preferably between $10^{12-18}$.

The highly complex primary antibody libraries can be used in a wide variety of applications. In particular, this library is used for screening of fully human antibody against a wide variety of targets, such as a defined antigen or a library of antigens associated with diseases.

The screening for antibody-antigen interaction may be conveniently carried out in yeast by using a yeast two-hybrid method. For example, a library of scFv expression vectors are introduced into yeast cells. Expression of the scFv antibody library in the yeast cells produces a library of scFv fusion (tester) proteins, each fusion protein comprising a scFv and an activation domain (AD) of a transcription activator. The yeast cells are also modified to express a recombinant fusion protein comprising a DNA-binding domain (BD) of the transcription activator and a target antigen. The yeast cells are also modified to express a reporter gene whose expression is under the control of a specific DNA binding site. Upon binding of the scFv antibody from the library to the target antigen, the AD is brought into close proximity of BD, thereby causing transcriptional activation of a reporter gene downstream from a specific DNA binding site to which the BD binds. It is noted that the library of scFv expression vectors may contain the BD domain while the modified yeast cells express a fusion protein comprising the AD domain and the target antigen.

These scFv expression vectors may be introduced to yeast cells by co-transformation of diploid yeast cells or by direct mating between two strains of haploid yeast cells. For example, the scFv expression vectors containing libraries of $V_H$ and $V_L$ and an expression vector containing the target antigen can be used to co-transform diploid yeast cells in a form of yeast plasmid or bacteria-yeast shuttle plasmid. Alternatively, two strains haploid yeast cells (e.g. α- and a-type strains of yeast), each containing the scFv expression vector and the target antigen expression vector, respectively, are mated to produce a diploid yeast cell containing both expression vectors. Preferably, the haploid yeast strain containing the target antigen expression vector also contains the reporter gene positioned downstream of the specific DNA binding site.

The yeast clones containing scFv antibodies with binding affinity to the target antigen are selected based on phenotypes of the cells or other selectable markers. The plasmids encoding these primary antibody leads can be isolated and further characterized.

The sequences encoding $V_H$ and $V_L$ of the primary antibody leads are mutagenized in vitro to produce a secondary antibody library. The $V_H$ and $V_L$ sequences can be randomly mutagenized by "poison" PCR (or error-prone PCR), by DNA shuffling, or by any other way of random or site-directed mutagenesis (or cassette mutagenesis). After mutagenesis in the regions of $V_H$ and $V_L$, the complexity of the secondary antibody library may reach $10^4$ or more.

Overall, the combined diversity or complexity of the total antibody libraries generated by using the methods of the present invention, including the primary and the secondary antibody libraries, may reach $10^{18}$ or more. The secondary antibody library are further screened for antibodies that bind the target antigen at high affinity by using the yeast-2-hybrid method as described above or other methods of screening in vivo or in vitro.

An advantage of the present invention is that the overall process of generating, selecting and optimizing large, diverse libraries of antibodies mimics the process of natural antibody diversification and maturation in a mammal. In the natural process of antibody affinity maturation, the affinity of the antibodies against their antigen(s) is progressively increased with the passage of time after immunization, largely due to the accumulation of point mutations specifically in the coding sequences of both the heavy- and light-chain variable regions.

According to the present invention, extensive diversification is achieved by recombination and mutagenesis of the $V_H$ and $V_L$ chain libraries derived from a wide variety of sources including natural and artificial or synthetic sources. The homologous combination of $V_H$ and $V_L$ in vivo to form the primary library of single-chain antibodies mimics the natural process of antibody gene assembly from different pools of gene segments encoding $V_H$ and $V_L$ of the antibodies. Since the method is preferably practiced with yeast cells, the highly efficient homologous recombination in yeast is particularly useful to facilitate such assembly of $V_H$ and $V_L$ in vivo.

The fast proliferation rate of yeast cells and ease of handling makes a process of "molecular evolution" dramatically shorter than the natural process of antibody affinity maturation in a mammal. Therefore, antibody repertoires with extremely high diversity can be produced and screened directly in yeast cells at a much lower cost and higher efficiency than prior processes such as the painstaking, stepwise "humanization" of monoclonal murine antibodies isolated by using the conventional hybridoma technology (a "protein redesign") or the recently-developed XENOMOUSE™ technology.

According to the "protein redesign" approach, murine monoclonal antibodies of desired antigen specificity are modified or "humanized" in vitro in an attempt to reshape the murine antibody to resemble more closely its human counterpart while retaining the original antigen-binding specificity. Riechmann et al. (1988) Nature 332:323–327. This humanization demands extensive, systematic genetic engineering of the murine antibody, which could take months, if not years. Additionally, extensive modification of the backbone of the murine monoclonal antibody may result in reduced specificity and affinity.

In comparison, by using the method of the present invention, fully human antibodies with high affinity to a specified antigen or antigens can be screened and isolated directly from yeast cells without going through site-by-site modification of the antibody, and without sacrifice of specificity and affinity of the selected antibodies.

The XENOMOUSE™ technology has been used to generate fully human antibodies with high affinity by creating strains of transgenic mice that produce human antibodies while suppressing the endogenous murine Ig heavy- and light-chain loci. However, the breeding of such strains of transgenic mice and selection of high affinity antibodies can take a long period of time. The antigen against which the pool of the human antibody is selected has to be recognized by the mouse as a foreign antigen in order to mount immune response; antibodies against a target antigen that does not have immunogenicity in a mouse may not be able to be selected by using this technology.

In contrast, by using the method of the present invention, libraries of antibody can not only be generated at a great diversity and complexity in yeast cells more efficiently and economically, but also be screened against virtually any protein or peptide target regardless of its immunogenicity. According to the present invention, any protein/peptide target can be expressed as a fusion protein with a DNA-binding domain (or an activation domain) of a transcription activator and selected against the library of antibody in a yeast-2-hybrid system. Moreover, multiple protein targets or a library of antigens may be arrayed in multiple-well plates and screened against the library of antibodies in a high throughput and automated manner.

Also compared to other approaches using transgenic goats and chickens to produce antibodies, the method of the present invention can be used to screen and produce fully human antibodies in large amounts without involving serious regulatory issues regarding the use of transgenic animals, as well as safety issues concerning containment of transgenic animals infected with recombinant viral vectors.

By using the method of the present invention, many requisite steps in the traditional construction of cDNA libraries can be eliminated. For example, the time-consuming and labor-intensive steps of ligation and recloning of cDNA libraries into expression vectors can be eliminated by direct recombination or "gap-filling" in yeast through general homologous recombination and/or site-specific recombination. Throughout the whole process of antibody library construction, the DNA fragments encoding $V_H$ and $V_L$ are directly incorporated into a linearized yeast expression vector via homologous recombination without the recourse to extensive recloning.

Compared with the approach of using phage display to screen for high affinity antibodies in vitro, the method of the present invention provides efficient ways of screening for high affinity antibodies in eukaryotic cells in vivo. By using phage display technology, human Ig heavy- and light chain variable regions are cloned, combinatorially reassorted, expressed and displayed as antigen-binding human Fab or scFv fragements on the surface of filamentous phage. Winter et al. (1994) Ann. Rev. Immunol. 433–455; and Rader et al. (1997) Current Opinion in Biotechnol. 8:503–508. The phage-displayed human antigen-binding fragments are then screened for their ability to bind an immobilized target antigen in vitro, a process called biopanning. When high affinity human antibodies are desired, the phage display approach can be problematic, presumably due to non-native conformation of antibody display on the surface and/or extensive selection or panning required for selection under in vitro conditions which bear little resemblance to the physiological condition of a human body. In contrast, by using the method of the present invention antibodies are selected based on their binding affinity to the target antigen in vivo. The antibodies are expressed in the cell, go through protein folding, and binds to its target antigen under a natural environment. Thus, the antibodies selected by using the method of the present invention should be more functionally relevant than those selected by panning in vitro.

1. Libraries of the Expression Vectors of the Present Invention

The present invention provides a library of expression vectors. In one embodiment, a library of yeast expression vectors are provided. Each of the yeast expression vectors in the library comprises a first nucleotide sequence V1 encoding a first polypeptide subunit; a second nucleotide sequence V2 encoding a second polypeptide subunit; and a linker sequence L encoding a linker peptide that links the first nucleotide sequence and the second nucleotide sequence. The first polypeptide subunit, the second polypeptide subunit, and the linker polypeptide are expressed as a single fusion protein. In addition, V1 and V2 each independently varies within the library of expression vectors.

According to the embodiment, the yeast expression vector may be a $2\mu$ plasmid vector, preferably a yeast-bacterial shuttle vector which contains a bacterial origin of replication.

In a variation of the embodiment, V1 is a coding sequence of the heavy-chain variable region of an antibody $V_H$. V2 is a coding sequence of the light-chain variable region of an antibody $V_L$.

The linker sequence L may have a specific sequence, or may vary within the library of the yeast expression vectors. Where L varies within the library, its sequence diversity preferably does not substantially alter the resulting conformation of the fusion protein.

When V1 and V2 are expressed by the yeast expression vector in yeast cells, such as cells from the *Saccharomyces cerevisiae* strains, the fusion protein comprising the V1 and V2 polypeptide segments undergoes a process of protein folding to adopt one or more conformations. The peptide sequence encoded by the linker sequence L may facilitate the folding by providing a flexible hinge between the V1 and V2 polypeptide segments. The conformation(s) adopted by the fusion protein may have suitable binding site(s) for a specific target protein. For example, the fusion protein may be a single-chain antibody scFv that binds to its specific target antigen.

In another embodiment, a library of expression vectors is provided. The expression vector in the library comprises: a transcription sequence encoding an activation domain AD or a DNA binding domain BD of a transcription activator; a first nucleotide sequence V1 encoding a first polypeptide subunit; a second nucleotide sequence V2 encoding a second polypeptide subunit; and a linker sequence L encoding a linker peptide that links the first nucleotide sequence and the second nucleotide sequence. The activation domain or the DNA binding domain of the transcription activator, the first polypeptide subunit, the second polypeptide subunit, and the linker polypeptide are expressed as a single fusion protein. In addition, V1 and V2 each independently varies within the library of expression vectors.

According to the embodiment, the expression vector may be any gene-transferring vector as long as it is able to introduce the library of expression vectors to a desired location within a host cell, such as by transformation, transfection and transduction of the expression vector into a host cell. The expression vector may be a bacterial, phage, yeast, mammalian or a viral expression vector, preferably a yeast expression vector, and more preferably a $2\mu$ plasmid yeast expression vector.

Also according to the embodiment, the transcription activator sequence may be located 5' relative to the first nucleotide sequence, the linker sequence, and the second nucleotide sequence. Alternatively, the transcription activator sequence may be located 3' relative to the first nucleotide sequence, the linker sequence, and the second nucleotide sequence.

In a variation of the embodiment, V1 is a coding sequence of the heavy-chain variable region of an antibody $V_H$. V2 is a coding sequence of the light-chain variable region of an antibody $V_L$. Optionally, AD is an activation domain of yeast GAL 4 transcription activator; and BD is a DNA binding domain of yeast GAL 4 transcription activator.

The linker sequence L may have a specific sequence, or vary within the library of the yeast expression vectors.

When V1 and V2 are expressed by the expression vector in host cells, such as cells from the *Saccharomyces cerevisiae* strains, the fusion protein comprising the AD, V1- and V2-encoded polypeptide segments undergoes a process of protein folding to adopt one or more conformations. The peptide sequence encoded by the linker sequence L also facilitates the folding by providing a flexible hinge between the V1- and V2-encoded polypeptide segments. The conformation(s) adopted by the fusion protein of the AD, V1 and V2-encoded polypeptide segments may have suitable binding site(s) for a specific target protein. For example, the fusion protein of AD, V1- and V2-encoded polypeptide segments may be a single-chain antibody scFv that binds to its specific target antigen. The AD domain of the fusion protein should be able to activate transcription of gene(s) once the AD and BD domains are reconstituted to form an active transcription activator in vitro or in vivo by a two-hybrid method.

According to any of the libraries described above, the diversity of the first and/or the second polypeptide subunit encoded by V1 and V2 within the library of expression vectors may be preferably between $10^3$–$10^8$, more preferably between $10^4$–$10^8$, and most preferably between $10^5$–$10^8$.

According to any of the libraries described above, the diversity of the first and/or the second polypeptide subunit encoded by V1 and V2 within the library of expression vectors may be preferably at least $10^3$, more preferably at least $10^4$, and most preferably at least $10^5$.

Also according to any of the libraries described above, the diversity of the fusion proteins encoded by the library of expression vectors is preferably between $10^6$–$10^{18}$, more preferably between $10^9$–$10^{18}$, and most preferably between $10^{10}$–$10^{18}$.

Also according to any of the libraries described above, the diversities of the first and second polypeptide subunits need not be derived from mutagenizing one or more proteins that are known to bind to a target peptide or protein. For example, the first and second polypeptide subunits need not be derived from mutagenizing a single antibody (e.g. the antibody Herceptin®) which is known to bind to a target peptide or protein (Her-2 receptor). This reflects a novel ability of the present invention to identify new protein-protein binding pairs from a random pool of sequences instead of having to know in advance a protein that binds to a target and then form a library of mutants from that known binding protein.

Also according to any of the libraries described above, the linker sequences L in the library of expression vectors is preferably between 30–120 bp in length, more preferably between 45–102 bp in length, and most preferably between 45–63 bp in length. The linker sequence in the library of expression vectors preferably comprises a nucleotide sequence encoding an amino acid sequence of Gly-Gly-Gly-Gly-Ser in 3 or 4 tandem repeats.

Also according to any of the libraries described above, the linker peptides expressed by the library of expression vectors preferably provide a substantially conserved conformation between the first and second polypeptide subunits across the fusion proteins expressed by the library of expression vectors. For example, a linker peptide Gly-Gly-Gly-Gly-Ser in 4 tandem repeats $(G_4S)_4$ [SEQ ID NO: 75] is believed to provide a substantially conserved conformation of scFv antibodies which preserves its antigen-binding site in the variable regions of the corresponding full antibody.

The elements of the expression vector in the library are described in detail below.

1) The Backbone of the Expression Vector

The expression vector of the present invention may be based on any type of vector as long as the vector that can transform, transfect or transduce a host cell. The expression vector contains a library of the V1 sequences and a library of V2 sequences, and preferably contains a sequence encoding an activation domain (AD) of a transcriptional activator. The acceptor vector may be plasmids, phages or viral vectors as long as it is able to replicate in vitro, or in a host cell, or to convey the library of the V1 and V2 sequences to a desired location within a host cell. Examples of host cells include, but are not limited to, bacterial (e.g. *E. coli, Bacillus subtilis*, etc.), yeast, animal, plant, and insect cells.

In a preferred embodiment, the expression vector is based on a yeast plasmid, especially one from *Saccharomyces cerevisiae*. After transformation of yeast cells, the exogenous DNA encoding the V1 and V2 sequences are uptaken by the cells and subsequently expressed by the transformed cells.

More preferably, the expression vector may be a yeast-bacteria shuttle vector which can be propagated in either *Escherichia coli* or yeast Struhl, et al. (1979) Proc. Natl. Acad. Sci. 76:1035–1039. The inclusion of *E. coli* plasmid DNA sequences, such as pBR322, facilitates the quantitative preparation of vector DNA in *E. coli*, and thus the efficient transformation of yeast.

The types of yeast plasmid vector that may serve as the shuttle may be a replicating vector or an integrating vector. A replicating vector is yeast vector that is capable of mediating its own maintenance, independent of the chromosomal DNA of yeast, by virtue of the presence of a functional origin of DNA replication. An integrating vector relies upon recombination with the chromosomal DNA to facilitate replication and thus the continued maintenance of the recombinant DNA in the host cell. A replicating vector may be a $2\mu$-based plasmid vector in which the origin of DNA replication is derived from the endogenous $2\mu$ plasmid of yeast. Alternatively, the replicating vector may be an autonomously replicating (ARS) vector, in which the "apparent" origin of replication is derived from the chromosomal DNA of yeast. Optionally, the replicating vector may be a centromeric (CEN) plasmid which carries in addition to one of the above origins of DNA replication a sequence of yeast chromosomal DNA known to harbor a centromere.

The vectors may be transformed into yeast cells in a closed circular form or in a linear form. Transformation of yeast by integrating vectors, although with inheritable stability, may not be efficient when the vector is in in a close circular form (e.g. 1–10 transformants per ug of DNA). Linearized vectors, with free ends located in DNA sequences homologous with yeast chromosomal DNA, transforms yeast with higher efficiency (100–1000 fold) and the transforming DNA is generally found integrated in sequences homologous to the site of cleavage. Thus, by cleaving the vector DNA with a suitable restriction endonuclease, it is possible to increase the efficiency of transformation and target the site of chromosomal integration. Integrative transformation may be applicable to the genetic modification of brewing yeast, providing that the efficiency of transformation is sufficiently high and the target DNA sequence for integration is within a region that does not disrupt genes essential to the metabolism of the host cell.

ARS plasmids, which have a high copy number (approximately 20–50 copies per cell) (Hyman et al., 1982), tend to be the most unstable, and are lost at a frequency greater than 10% per generation. However, the stability of ARS plasmids can be enhanced by the attachment of a centromere; centromeric plasmids are present at 1 or 2 copies per cell and are lost at only approximately 1% per generation.

The expression vector of the present invention is preferably based on the $2\mu$ plasmid. The $2\mu$ plasmid is known to be nuclear in cellular location, but is inherited in a non-Mendelian fashion. Cells that lost the $2\mu$ plasmid have been shown to arise from haploid yeast populations having an average copy number of 50 copies of the $2\mu$ plasmid per cell at a rate of between 0.001% and 0.01% of the cells per generation. Futcher & Cox (1983) J. Bacteriol. 154:612. Analysis of different strains of S. cerevisiae has shown that the plasmid is present in most strains of yeast including brewing yeast. The $2\mu$ plasmid is ubiquitous and possesses a high degree of inheritable stability in nature.

The $2\mu$ plasmid harbors a unique bidirectional origin of DNA replication which is an essential component of all $2\mu$-based vectors. The plasmid contains four genes, REP1, REP2, REP3 and FLP which are required for the stable maintenance of high plasmid copy number per cell Jaysram et al. (1983) Cell 34:95. The REP1 and REP2 genes encode trans-acting proteins which are believed to function in concert by interacting with the REP3 locus to ensure the stable partitioning of the plasmid at cell division. In this respect, the REP3 gene behaves as a cis acting locus which effects the stable segregation of the plasmid, and is phenotypically analogous to a chromosomal centromere. An important feature of the $2\mu$ plasmid is the presence of two inverted DNA sequence repeats (each 559 base-pairs in length) which separate the circular molecule into two unique regions. Intramolecular recombination between the inverted repeat sequences results in the inversion of one unique region relative to the other and the production in vivo of a mixed population of two structural isomers of the plasmid, designated A and B. Recombination between the two inverted repeats is mediated by the protein product of a gene called the FLP gene, and the FLP protein is capable of mediating high frequency recombination within the inverted repeat region. This site specific recombination event is believed to provide a mechanism which ensures the amplification of plasmid copy number. Murray et al. (1987) EMBO J. 6:4205.

The expression vector may also contain an *Escherichia coli* origin of replication and *E. coli* antibiotic resistance genes for propagation and antibiotic selection in bacteria. Many *E. coli* origins are known, including ColE1, pMB1 and pBR322, The ColE origin of replication is preferably used in this invention. Many *E. coli* drug resistance genes are known, including the ampicillin resistance gene, the chloramphenoicol resistance gene and the tetracycline resistance gene. In one particular embodiment, the ampicillin resistance gene is used in the vector.

The transformants that carry the V1 and V2 sequences may be selected by using various selection schemes. The selection is typically achieved by incorporating within the vector DNA a gene with a discernible phenotype. In the case of vectors used to transform laboratory yeast, prototrophic genes, such as LEU2, URA3 or TRP1, are usually used to complement auxotrophic lesions in the host. However, in order to transform brewing yeast and other industrial yeasts, which are frequently polyploid and do not display auxotrophic requirements, it is necessary to utilize a selection system based upon a dominant selectable gene. In this respect replicating transformants carrying $2\mu$-based plasmid vectors may be selected based on expression of marker genes which mediate resistance to: antibiotics such as G418, hygromycin B and chloramphenicol, or otherwise toxic materials such as the herbicide sulfometuron methyl, compactin and copper.

2) The V1 and V2 Variable Sequences

The first and the second polypeptide subunits encoded by V1 and V2, respectively, may be subunits of any multimeric protein. The sequence of the multimeric protein varies within a library or a collection of multimeric proteins. Example of the multimeric proteins include, but are not limited to antibodies, growth factor receptors, T cell receptors, cytokine receptors, tyrosine kinaseassociated receptors, and MHC proteins.

In preferred embodiment, the multimeric proteins are a library of antibodies, and more preferably human antibodies. For example, the first and second polypeptide subunits encoded by the library of expression vectors may be a human antibody heavy-chain variable region $V_H$ and a human antibody light-chain variable region $V_L$.

DNA sequences encoding human antibody $V_H$ and $V_L$ segments may be polynucleotide segments of at least 30 contiguous base pairs substantially encoding genes of the immunoglobulin superfamily. A. F. Williams and A. N. Barclay (1989) "The Immunoglobulin Gene Superfamily", in Immunoglobulin Genes, T. Honjo, F. W. Alt, and T. H. Rabbitts, eds., Academic Press: San Diego, Calif., pp.361–387. The $V_H$ and $V_L$ genes are most frequently encoded by human, non-human primate, avian, porcine, bovine, ovine, goat, or rodent heavy chain and light chain gene sequences.

The library of DNA sequences encoding human antibody $V_H$ and $V_L$ segments may be derived from a variety of sources. For example, mRNA encoding the human antibody $V_H$ and $V_L$ libraries may be extracted from cells or organs from immunized or non-immunized animals or humans. Preferably, organs such as human fetal spleen and lymph nodes may be used. Peripheral blood cells from non-immunized humans may also be used. The blood samples may be from an individual donor, from multiple donors, or from combined blood sources.

The human antibody $V_H$- and $V_L$-coding sequences may be derived and amplified by using sets of oligonucleotide primers to amplify the cDNA of human heavy and light chains variable domains by polymerase chain reaction (PCR). Orlandi et al. (1989) Proc. Natl. Acad. Sci. USA 86: 3833–3837. For example, blood sample may be from healthy volunteers and B-lymphocyte in the blood can be isolated. RNA can be prepared by following standard procedures. Cathala et al. (1983) DNA 3:329. The cDNA can be made from the isolated RNA by using reverse transcriptase.

Alternatively, the $V_H$- and $V_L$-coding sequences may be derived from an artificially rearranged immunoglobulin gene or genes. For example, immunoglobulin genes may be rearranged by joining of germ line V segments in vitro to J segments, and, in the case of $V_H$ domains, D segments. The joining of the V, J and D segments may be facilitated by using PCR primers which have a region of random or specific sequence to introduce artificial sequence or diversity into the products.

The fusion protein formed by linking $V_H$ and $V_L$ polypeptides is also referred as a single-chain antibody, scFv. A typical scFv comprises a $V_H$ domain and a $V_L$ domain in polypeptide linkage, generally linked via a spacer/linker peptide L. The linker peptide sequence L may encode an appropriately designed linker peptide, such as (Gly-Gly-Gly-Gly-Ser)$_4$ [SEQ. ID NO: 75] or equivalent linker peptide(s). The linker bridges the C-terminus of the first V region and N-terminus of the second, ordered as either $V_H$-L-$V_L$ or $V_L$-L-$V_H$.

A scFv may comprise additional amino acid sequences at the amino- and/or carboxy-termini. For example, a single-chain antibody may comprise a tether segment for linking to the constant regions of a complete or full antibody. A functional single-chain antibody generally contains a sufficient portion of an immunoglobulin superfamily gene product so as to retain the property of binding to a specific target molecule, typically a receptor or antigen (epitope).

Optionally, the variable sequences V1 and V2 of the library of expression vectors may also be derived from multimeric proteins other than antibodies. V1 and V2 may be different subunits of a non-antibody multimeric protein, such as membrane proteins and cell surfaces receptor proteins, e.g. insulin receptor, MHC proteins (e.g. class I MHC and class II MHC protein), CD3 receptor, T cell receptors, cytokine receptors such as interleukin-2 (IL-2) receptor which is made of α, β, and γ subunits, tyrosine-kinase-associated receptors such as Src, Yes, Fgr, Lck, Lyn, Hck, and Blk. The tyrosine-kinase-associated receptors contain SH2 and SH3 domains which are held there partly by their interactions with transmembrane receptor proteins and partly by covalently attached lipid chains. For example, V1 and V2 sequences may be mutagenized sequences of the SH2 and SH3 domains of a tyrosine-kinase-associated receptor such as Src, respectively, which are incorporated into the expression of vector of the present invention and screened against various ligands for this receptor.

It is noted that V1 and V2 sequences may also be derived from libraries of different and diverse proteins which may be monomeric, and linked by the linker sequence L.

A reflection of the power and versatility of the methods of the present invention is that the V1 and V2 sequences need not be based in any way on a protein sequence known to bind to the target. Instead, V1 and V2 may be from any source and may have a diversity that is entirely independent from the target, or one or more lead proteins known to bind to the target.

3) The Target Proteins and Peptides

The target fusion protein may comprise any target protein or peptide that may be expressed or otherwise present in a host cell. The target protein may be a member of library of proteins or peptides, such as a collection of human ESTs, a total library of human ESTs, a collection of domain structures (e.g. Zn-finger protein domains), or a totally random peptide library.

For example, the target protein or peptide may be a disease-associated antigen, such as tumor surface antigen such as B-cell idiotypes, CD20 on malignant B cells, CD33 on leukemic blasts, and HER2/neu on breast cancer. Antibody selected against these antigens can be used in a wide variety of therapeutic and diagnostic applications, such as treatment of cancer by direct administration of the antibody itself or the antibody conjugated with a radioisotope or cytotoxic drug, and in a combination therapy involving coadministration of the antibody with a chemotherapeutic agent, or in conjunction with radiation therapy.

Alternatively, the target protein may be a growth factor receptor. Examples of the growth factor include, but are not limited to, epidermal growth factors (EGFs), transferrin, insulin-like growth factor, transforming growth factors (TGFs), interleukin-1, and interleukin-2. For example, high expression of EGF receptors have been found in a wide variety of human epithelial primary tumors. TGF-α have been found to mediate an autocrine stimulation pathway in cancer cells. Several murine monoclonal antibody have been demonstrated to be able to bind EGF receptors, block the binding of ligand to EGF receptors, and inhibit proliferation of a variety of human cancer cell lines in culture and in xenograft medels. Mendelsohn and Baselga (1995) Antibodies to growth factors and receptors, in Biologic Therapy of Cancer, $2^{nd}$ Ed., JB Lippincott, Philadelphia, pp607–623. Thus, fully human antibodies selected against these growth factors by using the method of the present invention can be used to treat a variety of cancer.

The target protein may also be cell surface protein or receptor associated with coronary artery disease such as platelet glycoprotein Iib/IIIa receptor, autoimmune diseases such as CD4, CAMPATH-1 and lipid A region of the gram-negative bacterial lipopolysaccharide. Humanized antibodies against CD4 has been tested in clinical trials in the treatment of patients with mycosis fungoides, generalized postular psoriasis, severe psorisis, and rheumatoid arthritis. Antibodies against lipid A region of the gram-negative bacterial lipopolysaccharide have been tested clinically in the treatment of septic shock. Antibodies against CAMPATH-1 has also been tested clinically in the treatment of against refractory rheumatoid arthritis. Thus, fully human antibodies selected against these growth factors by using the method of the present invention can be used to treat a variety of autoimmune diseases. Vaswani et al. (1998) "Humanized antibodies as potential therapeutic drugs" Annals of Allergy, Asthma and Immunology 81:105–115.

The target protein or peptide may also be proteins or peptides associated with human allergic diseases, such as those inflammatory mediator protein, e.g. Interleukin-1 (IL-1), tumor necrosis factor (TNF), leukotriene receptor and 5-lipoxygenase, and adhesion molecules such as V-CAM/VLA4. In addition, IgE may also serve as the target antigen because IgE plays pivotal role in type I immediate hypersensitive allergic reactions such as asthma. Studies have shown that the level of total serum IgE tends to correlate with severity of diseases, especially in asthma. Burrows et al. (1989) "Association of asthma with serum IgE levels and skin-test reactivity to allergens" New Engl. L. Med. 320:271–277. Thus, fully human antibodies selected against IgE by using the method of the present invention may be used to reduce the level of IgE or block the binding of IgE to mast cells and basophils in the treatment of allergic diseases without having substantial impact on normal immune functions.

The target protein may also be a viral surface or core protein which may serve as an antigen to trigger immune response of the host. Examples of these viral proteins include, but are not limited to, glycoproteins (or surface antigens, e.g., GP120 and GP41) and capsid proteins (or structural proteins, e.g., P24 protein); surface antigens or core proteins of hepatitis A, B, C, D or E virus (e.g. small hepatitis B surface antigen (SHBsAg) of hepatitis B virus and the core proteins of hepatitis C virus, NS3, NS4 and NS5 antigens); glycoprotein (G-protein) or the fusion protein (F-protein) of respiratory syncytial virus (RSV); surface and core proteins of herpes simplex virus HSV-1 and HSV-2 (e.g., glycoprotein D from HSV-2).

The target protein may also be a mutated tumor suppressor gene that have lost its tumor-suppressing function and may render the cells more susceptible to cancer. Tumor suppressor genes are genes that function to inhibit the cell growth and division cycles, thus preventing the development of neoplasia. Mutions in tumor suppressor genes cause the cell to ignore one or more of the components of the network of inhibitory signals, overcoming the cell cycle check points and resulting in a higher rate of controlled cell growth-cancer. Examples of the tumor suppressor genes include, but are not limited to, DPC-4, NF-1, NF-2, RB, p53, WT1, BRCA1 and BRCA2.

DPC-4 is involved in pancreatic cancer and participates in a cytoplasmic pathway that inhibits cell division. NF-1 codes for a protein that inhibits Ras, a cytoplasmic inhibitory protein. NF-1 is involved in neurofibroma and pheochromocytomas of the nervous system and myeloid leukemia. NF-2 encodes a nuclear protein that is involved in meningioma, schwanoma, and ependymoma of the nervous system. RB codes for the pRB protein, a nuclear protein that is a major inhibitor of cell cycle. RB is involved in retinoblastoma as well as bone, bladder, small cell lung and breast cancer. P53 codes for p53 protein that regulates cell division and can induce apoptosis. Mutation and/or inaction of p53 is found in a wide ranges of cancers. WT1 is involved in Wilms tumor of the kidneys. BRCA1 is involved in breast and ovarian cancer, and BRCA2 is involved in breast cancer. Thus, fully human antibodies selected against a mutated tumor suppressor gene product by using the method of the present invention can be used to block the interactions of the gene product with other proteins or biochemicals in the pathways of tumor onset and development.

2. Construction of the Library of Expression Vectors of the Present Invention The library of expression vectors described above can be constructed using a variety of recombinant DNA techniques. The present invention provides novel and efficient methods of constructing these libraries of expression vectors with extreme diversity of V1 and V2 in vivo and in vitro.

The methods of the present invention are provided by exploiting the inherent ability of yeast cells to facilitate homologous recombination at an extremely high efficiency. The mechanism of homologous recombination in yeast and its applications is briefly described below.

Yeast *Saccharomyces cerevisiae* has an inherited genetic machinery to carry out efficient homologous recombination in the cell. This mechanism is believed to benefit the yeast cells for chromosome repair purpose and traditionally also called gap repair or gap filling. By this mechanism of efficient gap filling, mutations can be introduced into specific loci of the yeast genome. For example, a vector carrying the mutant gene contains two sequence segments that are homologous to the 5' and 3' open reading frame (ORF) sequences of the gene that is intended to be interrupted or mutated. The plasmid also contains a positive selection marker such a nutritional enzyme allele, such as ura3, or an antibiotic resistant marker such as Geneticine (g418) that are flanked the be two homologous segments. This plasmid is linearized and transformed into the yeast cells. Through homologous recombination between the plasmid and the yeast genome at the two homologous recombination sites, a reciprocal exchange of the DNA content occurs between the wild type gene in the yeast genome and the mutant gene (including the selection marker gene) that are flanked by the two homologous sequence segments. By selecting for the positive nutritional marker, surviving yeast cells will loose the original wild type gene and will adopt the mutant gene. Pearson B M, Hernando Y, and Schweizer M, (1998) Yeast 14: 391–399. This mechanism has also been used to make systematic mutations in all 6,000 yeast genes or ORFs for functional genomics studies. Because the exchange is reciprocal, similar approach has been used successfully for cloning yeast genomic fragments into plasmid vector. Iwasaki T, Shirahige K, Yoshikawa H, and Ogasawara N, Gene 1991, 109 (1): 81–87.

By using homologous recombination in yeast, gene fragments or synthetic oligonucleotides can also be cloned into a plasmid vector without a ligation step. In this application, a targeted gene fragment is usually obtained by PCR amplification (or by using the conventional restriction digestion out of an original cloning vector). Two short fragment sequences that are homologous to the plasmid vector are added to the 5' and 3' of the target gene fragment in the PCR amplification. This can be achieved by using a pair of PCR primers that incorporate the added sequences. The plasmid vector typically includes a positive selection marker such as nutritional enzyme allele such as ura3, or an antibiotic resistant marker such as geneticin (g418). The plasmid vector is linearized by a unique restriction cut in between the sequence homologies that are shared with the PCR-amplified target, thereby creating an artificial gap at the cleavage site. The linearized plasmid vector and the target gene fragment flanked by sequences homologous to the plasmid vector are co-transformed into a yeast host strain. The yeast recognizes the two stretches of sequence homologies between the vector and target fragment, and facilitates a reciprocal exchange of DNA contents through homologous recombination at the gap. As the consequence, the target fragment is automatically inserted into the vector without ligation in vitro.

There are a few factors that may influence the efficiency of homologous recombination in yeast. The efficiency of the gap repair is correlated with the length of the homologous sequences flanking both the linearized vector and the targeted gene. Preferably, a minimum of 30 base pairs may be required for the length of the homologous sequence, and 80 base pairs may give a near-optimized result. Hua, S. B. et al. (1997) "Minimum length of sequence homology required for in vitro cloning by homologous recombination in yeast" Plasmid 38:91–96. In addition, the reciprocal exchange between the vector and gene fragment is strictly sequence-dependent, i.e. not causing frame shift in this type of cloning. Therefore, such a unique characteristic of the gap-repair cloning assures insertion of gene fragments with both high efficiency and precision. The high efficiency makes it possible to clone two or three targeted gene fragments simultaneously into the same vector in one transformation attempt. Raymond K., Pownder T. A., and Sexson S. L., (1999) Biotechniques 26: 134–141. The nature of precision sequence conservation through homologous recombination makes it possible to clone targeted genes in question into expression or fusion vectors for direct function examinations. So far many functional or diagnostic applications have been reported using homologous recombination. El-Deiry W. W., et al., Nature Genetics1: 45–49, 1992 (for p53), and Ishioka C., et al., PNAS, 94: 2449–2453, 1997 (for BRCA1 and APC).

A library of gene fragments may also be constructed in yeast by using homologous recombination. For example, a human brain cDNA library can be constructed as a two-hybrid fusion library in vector pJG4-5. Guidotti E., and Zervos A. S. (1999) "In vivo construction of cDNA library for use in the yeast two-hybrid systems" Yeast 15:715–720. It has been reported that a total of 6,000 pairs of PCR primers were used for amplification of 6,000 known yeast ORFs for a study of total yeast genomic protein interaction. Hudson, J. Jr, et al. (1997) Genome Res. 7:1169–1173. Uetz et al. conducted a comprehensive analysis of protein-protein interactions in *Saccharomyces cerevisiae*. Uetz et al. (2000) Nature 403:623–627. The protein-protein interaction map of the budding yeast was studied by using a comprehensive system to examine two-hybrid interactions in all possible combinations between the yeast proteins. Ito et al. (2000) Proc. Natl. Acad. Sci. USA. 97:1143–1147. The genomic protein linkage map of Vaccinia virus was studied by McCraith S., Holtzman T., Moss B., and Fields, S. (2000) Proc. Natl. Acad. Sci. USA 97: 4879–4884.

According to the present invention, the V1 and V2 sequences are introduced into an expression vector by homologous recombination performed directly in yeast cells.

1) Cloning of V1 and V2 in Separate Fragments into an Expression Vector Through Two Independent Events of Homologous Recombination in Yeast In one embodiment of the method for generating the library of expression vectors, the V1 and V2 sequences may be cloned into an expression vector in vivo in two separate fragments through two independent events of homologous recombination in yeast.

The method comprises:
a) transforming into yeast cells i) a linearized yeast expression vector having a 5'- and 3'-terminus sequence at a first site of linearization; and ii) a library of first insert nucleotide sequences that are linear, double stranded, each of the first insert sequences comprising a first nucleotide sequence V1 encoding a first polypeptide subunit, a 5'- and 3'-flanking sequence at the ends of the first insert sequence which are sufficiently homologous to the 5'- and 3'-terminus sequences of the vector at the first site of linearization, respectively, to enable homologous recombination to occur;
b) having homologous recombination occur between the vector and the first insert sequence in the transformed yeast cells, such that the first insert sequence is included in the vector;
c) isolating from the transformed yeast cells the vectors that contain the library of the first insert sequences;
d) linearizing the vectors containing the library of the first insert sequences to generate a 5'- and 3'-terminus sequence at a second site of linearization;
e) transforming into yeast cells
   i) the linearized yeast expression vectors in step d), and
   ii) a library of second insert nucleotide sequences that are linear, double stranded, each of the second insert sequences comprising a second nucleotide sequence V2 encoding a second polypeptide subunit, a 5'- and 3'-flanking sequence at the ends of the second insert sequence which are sufficiently homologous to the 5'- and 3'-terminus sequences of the vector at the second site of linearization, respectively, to enable homologous recombination to occur; and
f) having homologous recombination occur between the linearized yeast expression vector at the second linearization site and the second insert sequences in the transformed yeast cells, such that the second insert sequence is included in the vector and the first and second nucleotide sequences are linked by a linker sequence L.

In this embodiment, the expression vector expresses the first polypeptide subunit, the second polypeptide subunit, and the linker polypeptide as a single fusion protein. Also, the first and second nucleotide sequences each independently varies within the library of expression vectors.

According to the embodiment, the 5'- or 3'-flanking sequence of the insert nucleotide sequence is preferably between about 30–120 bp in length, more preferably between about 40–90 bp in length, and most preferably between about 60–80 bp in length.

Figure 2:
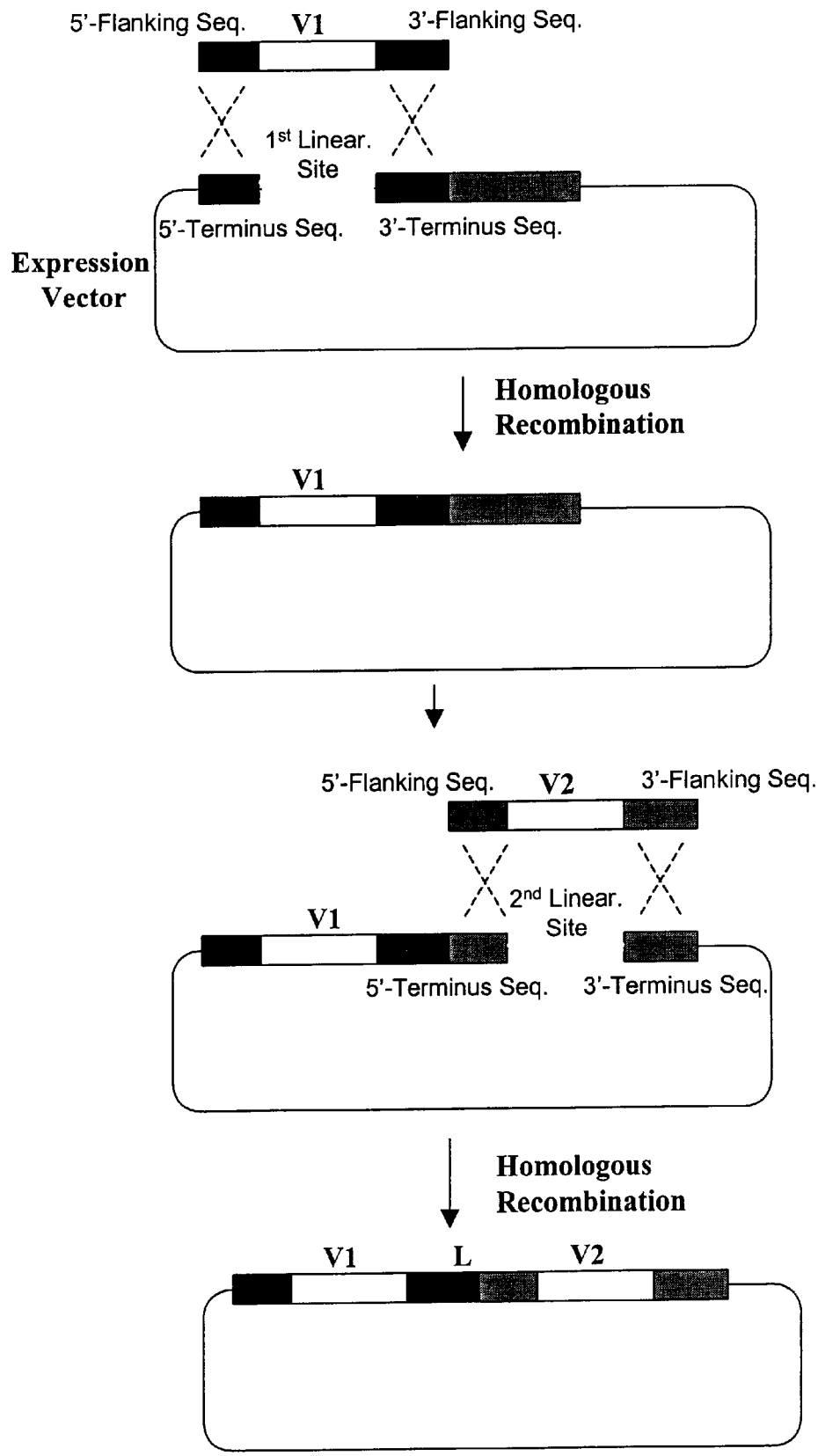
FIG. 2 illustrates an embodiment of a method for generating a library of expression vectors by sequentially inserting V1 and V2 fragments into a linearized expression vector via homologous recombination.

FIG. 2 illustrates an embodiment of this method according to the present invention. The coding sequences for V1 (e.g., $V_H$) and V2 (e.g., $V_L$) are carried by separate PCR fragments and cloned into an expression vector sequentially following two independent events of homologous recombination in yeast.

As illustrated in FIG. 2, the V1 fragment has a 5' flanking sequence and a 3' flanking sequence that are homologous to the 5' and 3' terminus of a linearized expression vector, respectively. When the V1 fragment and the linearized expression vector are introduced into a host cell, for example, transformed into a yeast cell, the "gap" (the first linearization site) created by linearization of the expression vector is filled by the V1 fragment insert through recombination of the homologous sequences at the 5' and 3' terminus of these two linear double-stranded DNA. Through this event of homologous recombination, a library of circular vectors carrying the variable sequence V1 is generated.

This library of circular vectors is then cleaved at a second linearization site, for example, a site downstream of V1. The V2 fragment has a 5' flanking sequence and a 3' flanking sequence that are homologous to the 5' and 3' terminus of the linearized expression vector at the second linearization site. The V2 fragment and the linearized expression vector are transformed into a yeast cell. Through a second event of homologous recombination, the V2 fragment is inserted into the linearized expression vector at the second linearization site. As a result, a library of circular vectors carrying the variable sequences V1 and V2 is generated.

Each flanking sequence added to the V1 and V2 coding sequence may be preferably between about 30–120 bp in length, more preferably between about 40–100 bp in length, and most preferably 60–80 bp in length.

The region between the V1 and V2 sequences, i.e. the linker sequence L, is preferably be 30–120 bp in length, more preferably 45–102 bp in length, and more most preferably 45–63 bp in length. The linker sequence preferably codes for an amino acid sequence of Gly-Gly-Gly-Gly-Ser ($G_4S$) in multiple tandem repeats, more preferably codes for $(G_4S)_{3-6}$ and most preferably codes for $(G_4S)_{3-4}$. Optionally, the linker sequence may further include a site-specific homologous recombination site, such as a loxP site.

When the V1 and V2 coding sequences are inserted into an expression vector containing an AD domain, it is preferred that the reading frames of the V1 and V2 fragments are conserved with upstream AD reading frame.

Depending on the cloning expression vector used, additional features such as affinity tags and unique restriction enzyme recognition sites may be added to the expression for the convenience of detection and purification of the inserted V1 and V2 sequences. Examples of affinity tags include, but are not limited to, a polyhistidine tract, polyarginine, glutathione-S-transferase (GST), maltose binding protein (MBP), a portion of staphylococcal protein A (SPA), and various immunoaffinity tags (e.g. protein A) and epitope tags such as those recognized by the EE (Glu-Glu) antipeptide antibodies.

In a preferred embodiment, the V1 and V2 sequences may be the coding sequences for a heavy-chain variable region $V_H$ and a light-chain variable region $V_L$, respectively, which are derived from a human antibody repertoire. To generate the V1 and V2 coding sequences from the human antibody repertoire, a complex human scFv cDNA gene pool may generated by using the methods known in the art. Sambrook, J., et al. (1989) Molecular Cloning: a laboratory manual. Cold Spring Harbor Laboratory, Cold Spring Harbor, N.Y.; and Ausubel, F. M. et al. (1995) Current Protocols in Molecular Biology" John Wiley & Sons, NY.

Total RNA may be isolated from sources such as the white cells (mainly B cells) contained in peripheral blood supplied by un-immunized humans, or from human fetal spleen and lymph nodes. First strand cDNA synthesis may be synthesized performed by using methods known in the art, such as those described by Marks et al. Marks et al. (1991) Eur. J. Immunol. 21:985–991.

Specifically, a mixture of heavy and light chain cDNA primer sets designed to anneal to the constant regions may be used for priming the synthesis of cDNA of heavy chain and light chains (both kappa Vκ and lambda Vλ) antibody genes. Examples of how to generate the cDNA library of human $V_H$ and $V_L$ genes are illustrated in Example 1.

The coding sequences of human heavy and light chain genes may be amplified from the $V_H$ and $V_L$ cDNA library generated above by using PCR primer sets used in combination to prime the heavy chain variable region $V_H$, and the light chain variable regions Vλ and Vκ. The each of the PCR primers may include both a $V_H$, Vλ or Vκ partial sequence and a 5' or 3' flanking sequence for facilitating homologous recombination between the $V_H$ and $V_L$ fragments and a cloning expression vector. Examples of these primers are listed in Table 2.

2) Cloning of V1 and V2 that is Assembled in a Single Fragment into an Expression Vector via Homologous Recombination in Yeast In another embodiment of the method for generating the library of expression vectors, the V1 and V2 sequences may be assembled into a single DNA fragment in vitro by using, for example, a PCR method. The single fragment comprising V1, V2 and L may then be cloned into an expression vector via homologous recombination in yeast.

The method comprises: transforming into yeast cells a linearized yeast expression vector having a 5'- and 3'-terminus sequence at the site of linearization and a library of insert nucleotide sequences that are linear and double-stranded. Each of the insert sequences comprises a first nucleotide sequence V1 encoding a first polypeptide subunit, a second nucleotide sequence V2 encoding a second polypeptide subunit, and a linker sequence L encoding a linker peptide that links the first and second polypeptide subunits. Each of the insert sequences also comprises a 5'- and 3'-flanking sequence at the ends of the insert sequence. The 5'- and 3'-flanking sequence of the insert sequence are sufficiently homologous to the 5'- and 3'-terminus sequences of the linearized yeast expression vector, respectively, to enable homologous recombination to occur. The homologous recombination occurring between the vector and the insert sequence results in inclusion of the insert sequence into the vector in the transformed yeast cells.

In this embodiment, the first polypeptide subunit, the second polypeptide subunit, and the linker polypeptide are expressed as a single fusion protein. Also, the first and second nucleotide sequences each independently varies within the library of expression vectors.

According to the embodiment, the 5'- or 3'-flanking sequence of the insert nucleotide sequence is preferably between about 30–120 bp in length, more preferably between about 40–90 bp in length, and most preferably between about 60–80 bp in length.

Figure 3:
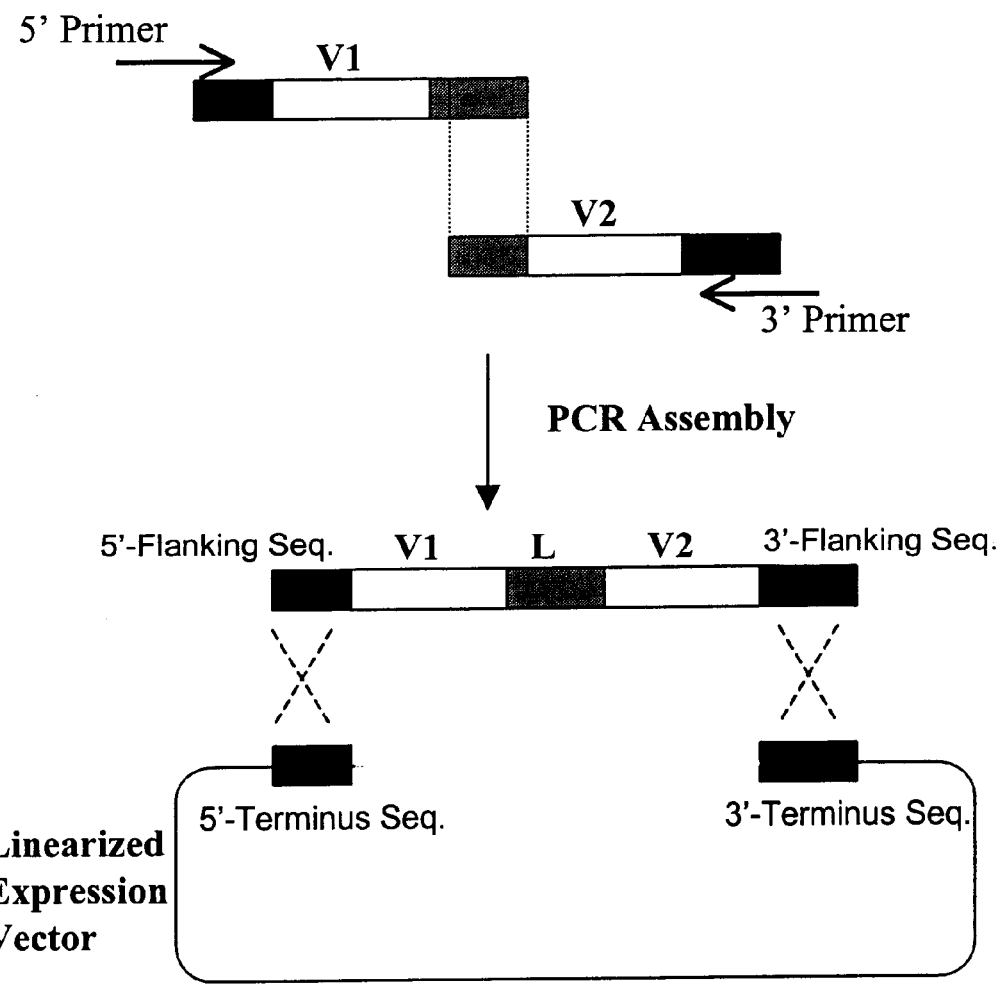
FIG. 3 illustrates an embodiment of a method for generating a library of expression vectors by inserting a single fragment comprising V1 and V2 segments into a linearized expression vector via homologous recombination.
Figure 3:
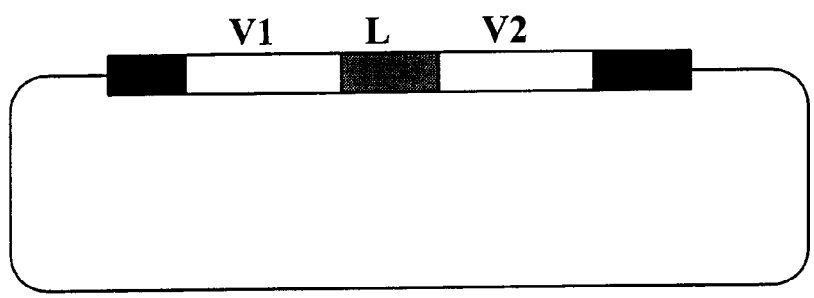

FIG. 3 illustrates an embodiment of this method according to the present invention. The coding sequences for V1 (e.g., $V_H$) and V2 (e.g., $V_L$) are amplified by PCR to generate separate fragements which are then PCR-assembled into a single PCR fragment carrying both V1 and V2 sequences. This single PCR fragment is then cloned into an expression vector through homologous recombination in one step. The detailed procedures are described in Example 1.

As illustrated in FIG. 3, the V1 fragment has a flanking sequence at its 3' terminus that overlaps with a flanking sequence of the 5' terminus of the V2 fragment. By using a method of overlapping PCR priming, the V1 and V2 fragments are assembled into a single PCR fragment with a linkage sequence L in between, which is referred to as the V1-L-V2 fragment. This single PCR fragment has a 5' flanking sequence and a 3' flanking sequence that are homologous to the 5' and 3' terminus of a linearized expression vector at the cleavage site, respectively. When the V1-L-V2 fragment and the linearized expression vector are introduced into a host cell, for example, transformed into a yeast cell, the "gap" created by linearization of the expression vector is filled by the V1-L-V2 fragment insert through recombination of the homologous sequences at the 5' and 3' terminus of these two linear double-stranded DNA. Through this homologous recombination, a library of circular vectors carrying the variable sequences V1 and V2 is generated.

Each flanking sequence added to the 5' and 3'-terminus of V1 and V2 coding sequence is preferably between about 30–120 bp in length, more preferably between about 40–100 bp in length, and most preferably 60–80 bp in length.

The region between the V1 and V2 sequences, i.e. the linker sequence L, is preferably 30–120 bp in length, more preferably 45–102 bp in length, and more most preferably 45–63 bp in length. The linker sequence preferably codes for an amino acid sequence of Gly-Gly-Gly-Gly-Ser ($G_4S$) in multiple tandem repeats, more preferably codes for $(G_4S)_{3-6}$ and most preferably codes for $(G_4S)_{3-4}$. Optionally, the linker sequence may further include a site-specific homologous recombination site, such as a loxP site.

By using similar methods as described above, the variable sequences V1 and V2 can be inserted into an expression vector containing an activation domain (AD) or a DNA-binding domain (BD) of a transcription activator. The AD or BD domain may be positioned upstream or downstream of V1 and V2. It is preferred that the reading frames of the V1 and V2 fragments are conserved with the AD or BD reading frame.

The expression vector containing an AD (or BD) domain may be any vector engineered to carry the coding sequence of the AD domain. The expression vector is preferably a yeast vector such as pGAD10 (Feiloter et al. (1994) "Construction of an improved host strain for two hybrid screening" Nucleic Acids Res. 22: 1502–1503), pACT2 (Harper et al (1993) "The p21 Cdk-interacting protein Cip1 is a protein inhibitor of G1 cyclin-dependent kinase" Cell 75:805–816), and pGADT7 ("Matchmaker Gal4 two hybrid system 3 and libraries user manual" (1999), Clontech PT3247-1, supplied by Clontech, Palo Alto, Calif.).

Optionally, the expression vector containing an AD (or BD) domain may also include another expression unit which is capable of expressing one or more proteins other than the fusion proteins encoded by V1 and V2, such as the scFv antibodies. These proteins may be modifying enzymes such as kinase, glycosylase, and enzymes that help to form the disulfide bonds present in a mature antibody structure. Expression of the enzymes should facilitate or enhance posttranslational modifications that may be required for full functions of the fusion proteins encoded by V1 and V2.

Expression of these proteins may be under the transcriptional control of a constitutive promoter or an inducible promoter. One example of such an expression vector is available from Clontech, pBridge® (catalog No. 6184-1). The expression vector, pBridge®, contains one expression unit that controls expression of a Gal 4 BD domain and another expression unit that includes an inducible promoter Pmat25. Tirode, E. et al. (1997) J. Biol. Chem. 272:22995–22999.

The linearized vector DNA may be mixed with equal or excess amount of the PCR insert fragment: either V1 (or V2) in a separate fragment or in the single fragment comprising V1 and V2. The linearized vector DNA and the PCR fragment are co-transformed into host cells, such as competent yeast cells. Recombinant clones may be selected based on survival of cells in a nutritional selection medium or based on other phenotypic markers. Either the linearized vector or the insert DNA fragment alone may be used as a control for determining the efficiency of recombination and transformation.

Other homologous recombination systems may be used to generate the library of expression vectors of the present invention. For example, the recombination between the library of V1 and V2 sequences and the recipient expression vector may be facilitated by site-specific recombination.

The site-specific recombination employs a site-specific recombinase, a enzyme which catalyzes the exchange of DNA segments at specific recombination sites. Site-specific recombinases present in some viruses and bacteria, and have been characterized to have both endonuclease and ligase properties. These recombinases, along with associated proteins in some cases, recognize specific sequences of bases in DNA and exchange the DNA segments flanking those segments. Landy, A. (1993) Current Opinion in Biotechnology 3:699–707.

A typical site-specific recombinase is CRE recombinase. CRE is a 38-kDa product of the cre (cyclization recombination) gene of bacteriophage P1 and is a site-specific DNA recombinase of the Int family. Sternberg, N. et al. (1986) J. Mol. Biol. 187: 197–212. CRE recognizes a 34-bp site on the P1 genome called loxP (locus of X-over of P1) and efficiently catalyzes reciprocal conservative DNA recombination between pairs of loxP sites. The loxP site [SEQ ID NO: 1] consists of two 13-bp inverted repeats flanking an 8-bp nonpalindromic core region. CRE-mediated recombination between two directly repeated loxP sites results in excision of DNA between them as a covalently closed circle. Cre-mediated recombination between pairs of loxP sites in inverted orientation will result in inversion of the intervening DNA rather than excision. Breaking and joining of DNA is confined to discrete positions within the core region and proceeds on strand at a time by way of transient phophotyrosine DNA-protein linkage with the enzyme.

The CRE recombinase also recognizes a number of variant or mutant lox sites relative to the loxP sequence. Examples of these Cre recombination sites include, but are not limited to, the loxB, loxL and loxR sites which are found in the E. coli chromosome. Hoess et al. (1986) Nucleic Acid Res. 14:2287–2300. Other variant lox sites include, but are not limited to, loxB, loxL, loxR, loxP3, loxP23, loxΔ86, loxΔ117, loxP511 [SEQ ID NO:2], and loxC2 [SEQ ID NO:3]. Table 1 lists examples of lox sites that may be used in the present invention, including wild-type loxP sites LoxP WT [SEQ ID NO: 1] and loxP2 [SEQ ID NO: 5], and other loxP variants with mutations in the 13-bp inverted repeats region and/or the 8-bp nonpalindromic core region (underlined), loxP511 [SEQ ID NO: 2], loxC2 [SEQ ID NO: 3], loxP1 [SEQ ID NO: 4], loxP3 [SEQ ID NO: 6], loxP4 [SEQ ID NO: 7], loxP5 [SEQ ID NO: 8], loxP6 [SEQ ID NO: 9], loxP7 [SEQ ID NO: 10], loxP8 [SEQ ID NO: 11], loxP9 [SEQ ID NO: 12], and loxP10 [SEQ ID NO: 13].

Examples of the non-CRE recombinases include, but are not limited to, site-specific recombinases include: att sites recognized by the Int recombinase of bacteriophage λ (e.g. att1, att2, att3, attP, attB, attL, and attR), the FRT sites recognized by FLP recombinase of the 2 pi plasmid of Saccharomyces cerevisiae, the recombination sites recognized by the resolvase family, and the recombination site recognized by transposase of Bacillus thruingiensis.

Subsequent analysis may also be carried out to determine the efficiency of homologous recombination that results in correct insertion of the V1 and V2 sequences into the expression vector. For example, PCR amplification of the V1 and V2 inserts directly from the selected yeast clone may reveal how many clones are recombinant. Libraries with minimum of 90% recombinant clones are preferred. The same PCR amplification of selected clones may also reveal the insert size. Although a small fraction of the library may contain double or triple inserts, the majority (>90%) is preferably to have a single insert with the expected size.

To verify sequence diversity of the inserts in the selected clones, PCR amplification product with the correct size of insert may be fingerprinted with frequent digesting restriction enzymes. From a gel electrophoresis pattern, it may be determined whether the clones analyzed are of the same identity or of the distinct or diversified identity. The PCR products may also be sequenced directly to reveal the identity of inserts and the fidelity of the cloning procedure and to prove the independence and diversity of the clones.

In an embodiment where the V1 and V2 sequences are the coding sequences for a heavy-chain variable region $V_H$ and a light-chain variable region $V_L$ derived from a human antibody repertoire, respectively, mouse scFv fragments may be generated from hybridoma cell lines as controls by following the same procedures described above. Examples of hybridoma cell lines include, but are not limit to, anti-GFP antibody producing cell line (Clontech), anti-p53 antibodies producing cell lines (NeoMarker), and other hybridoma cell lines available from ATCC (Atlanta). The hybridoma cell line is subjected to the same procedures described above, i.e., RNA isolation, cDNA synthesis, PCR amplification, and homologous recombination into yeast. Other scFv antibody libraries may also be generated from mouse fetal liver and fetal spleen using the same principle.

The mouse scFV library generated can provide a direct control for existing individual mouse monoclonal antibody with its cognate antigen. Most studies for antigen-antibody interaction have been performed with mouse antibodies. The mouse scFV library should serve as an excellent control in the selection of human scFv antibody library against a target antigen by yeast two-hybrid method described below.

3) Chain-shuffling of Expression Vectors via CRE/loxP-mediated Site-specific Recombination In a variation of the above-described methods for generating the library of expression vectors, the diversity of the library of expression vectors may be increased by chain shuffling via site-specific recombination. Accordingly, the method further comprises: causing site-specific recombination between the members of the library of the yeast expression vectors at the 5'- and 3'-recombination sites, the recombination resulting in exchange of the first V1 or second V2 nucleotide sequences between the members of the library of the yeast expression vectors.

According to the variation, the 5'- and 3'-flanking sequences at the ends of the first or second insert nucleotide sequence comprise a 5'- and 3'-recombination site, respectively, that are recognized by a site-specific recombinase.

Also according to the variation, the 5'- and 3'-site-specific recombination sites may preferably be different site-specific recombination sites, more preferably be sites each of which is independently selected from the group consisting of SEQ ID Nos: 1–13, most preferably be loxP of coliphase P1, and the other be a mutant loxP sequence.

Also according to the variation, the site-specific recombinase may be constitutively or inducibly expressed in the yeast cells. The site-specific recombinase may be CRE recombinase that cause the site-specific recombination.

Figure 4A:
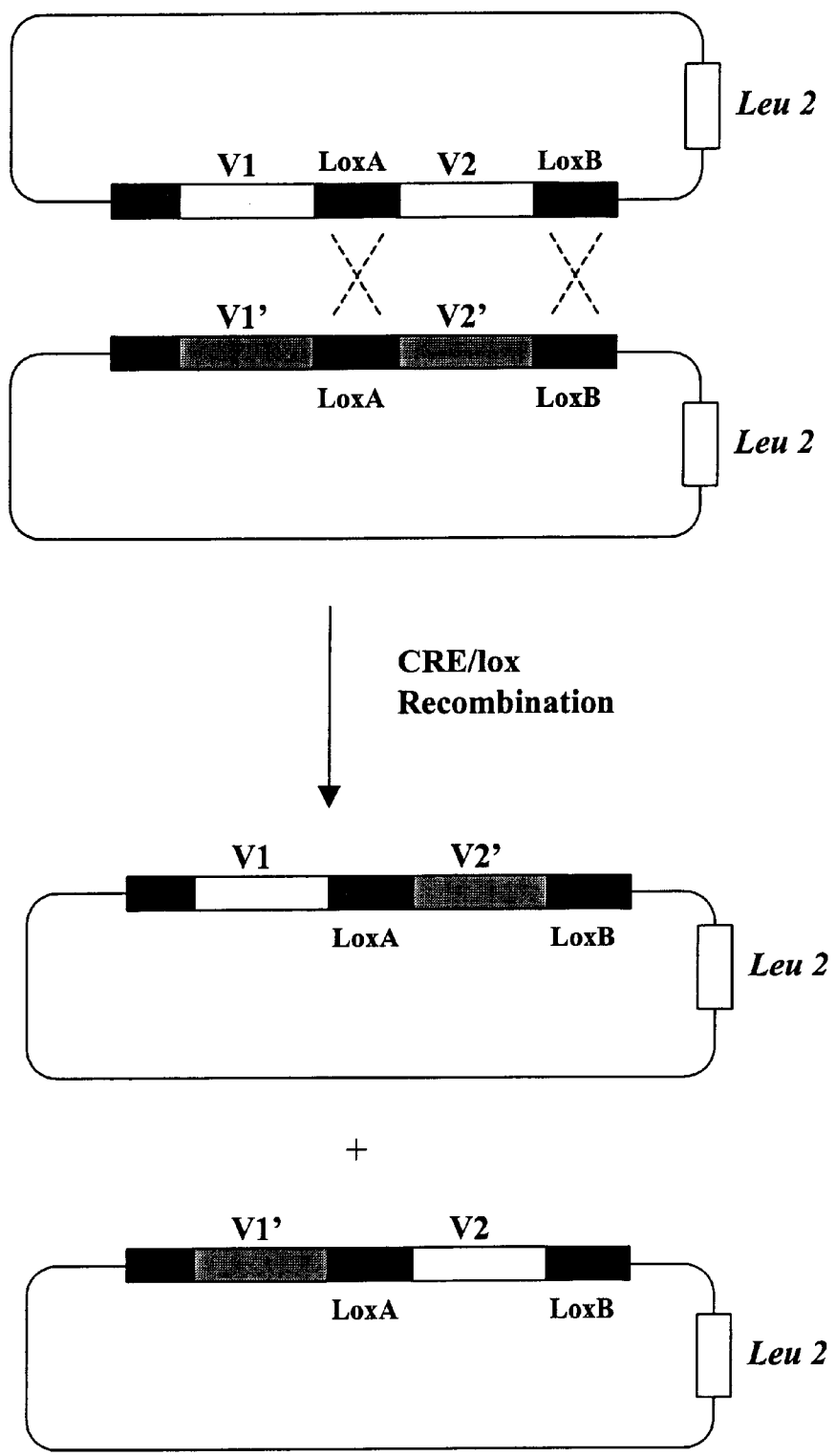
FIG. 4A illustrates an embodiment of a method for increasing the complexity of a library of expression vectors via CRE/LoxP mediated recombination.

FIG. 4A illustrates an embodiment of this method according to the present invention, the library of expression vectors containing V1 and V2 are subject to mutagenesis in vivo through site-specific homologous recombination. Each of the expression vector may contain the same yeast selection marker such as Leu 2. Through this mutagenesis, the diversity of the sequences encoding V1 and V2 can be further increased.

As illustrated in FIG. 4A, both the 5' and the 3' flanking sequences of the V2 (or V1) include a recombination site recognized by a site-specific recombinase. Preferably, the recombination site may be a lox site that is recognized by the CRE recombinase of bacteriophage P1. Table 1 lists examples of lox sites that may be used in the present invention, including wild-type loxP sites LoxP WT [SEQ ID NO: 1] and loxP2 [SEQ ID NO: 5], and other loxP variants with mutations in the 13-bp inverted repeats region and/or the 8-bp nonpalindromic core region (underlined), loxP511 [SEQ ID NO: 2], loxC2 [SEQ ID NO: 3], loxP1 [SEQ ID NO: 4], loxP3 [SEQ ID NO: 6], loxP4 [SEQ ID NO: 7], loxP5 [SEQ ID NO: 8], loxP6 [SEQ ID NO: 9], loxP7 [SEQ ID NO: 10], loxP8 [SEQ ID NO: 11], loxP9 [SEQ ID NO: 12], and loxP10 [SEQ ID NO: 13].

More preferably, the recombination sites in the 5' and the 3' flanking sequences are of different lox sites, loxA and loxB as illustrated in FIG. 4A. In the presence of CRE recombinase, the expression vector having the lox sites in the 5' (loxA) and 3' (loxB) flanking sequence of V2 (or V1) undergoes a "chain-shuffling" with another expression vector having the same lox sites in the 5' and 3' flanking sequence of V2' (or V1'), respectively. As a result, the V2 chain of the expression vector is replaced with the V2' chain of another expression vector, thereby increasing the complexity of the library from $10^n$ to $10^n \times 10^n = 10^{2n}$ theoretically.

Optionally, the recombination site may be a recombination site that is recognized by a recombinase other than CRE. Examples of the non-CRE recombinases include, but are not limited to, site-specific recombinases include: att sites recognized by the Int recombinase of bacteriophage λ (e.g. att1, att2, att3, attP, attB, attL, and attR), the FRT sites recognized by FLP recombinase of the 2pi plasmid of *Saccharomyces cerevisiae*, the recombination sites recognized by the resolvase family, and the recombination site recognized by transposase of *Bacillus thruingiensis*.

In a preferred embodiment where V1 is $V_H$ and V2 is $V_L$, the scFv library generated by the yeast homologous recombination is mutagenized by a CRE/loxP mediated site-specific recombination. For example, the scFv library may comprise $10^6$ or more highly diverse and complex V-region gene repertoire derived from heavy chain and light chain origin of human antibodies. One pool (e.g., the light chain gene pool $V_L$) is flanked by two non-identical Lox P sites that provide the recombination signals for light chain "shuffling" mediated by CRE recombinase.

The entire scFv library may be isolated from yeast and transformed into bacterial strain (e.g. KC8) through bacteria-yeast leucine nutritional marker complementation, and large scale DNA isolation from bacteria is performed and the DNA pools are mixed. This pooled DNA source is then re-introduced into yeast using conventional single plasmid transformation protocol. The condition of this transformation may preferably be set to enrich for multiple plasmid entry into every single yeast cell.

The yeast cell may be pre-transformed with a plasmid that stably, or more preferably inducibly, expresses CRE recombinase. The expression of CRE in the yeast strain should cause the CRE-mediated homologous recombination at the loxP sites that flank each light chain gene fragment VL on each expression vector. Therefore, while yeast is allowed to grow and the plasmids in the yeast cells are making additional copies, shuffling of the light chain gene segment occurs inside of yeast cells in the presence of CRE recombinase. Therefore, the total number of combination of heavy chain $V_H$ and light chain $V_L$ within the yeast cells may be increased exponentially. Thus, theoretically, the complexity of the library can reach $10^6 \times 10^6 = 10^{12}$ or higher.

One of the advantages of using the site-specific recombination in yeast is that the recombination in yeast does not require any marker selection. For example, CRE/loxP recombination will occur irrespective of with selection or without selection.

The multiple entry of the library of expression vectors into the yeast cells may be tested by using plasmids carrying green fluorescent protein (GFP) genes with different colors. If multiple plasmids are transformed into a single yeast cell, certain fraction of the transformed yeast cell will show a spectrum of combined colors. This test may also be used for optimizing the condition for transformation of multiple expression vectors.

Alternatively, multiple vectors from the library of expression vectors may be transformed into a single yeast cell by using a method of "forced transformation". Under this alternative embodiment, two starting libraries expression vectors containing V1 and V2 may be generated separately in two expression vectors with different selection markers.

Figure 4B:
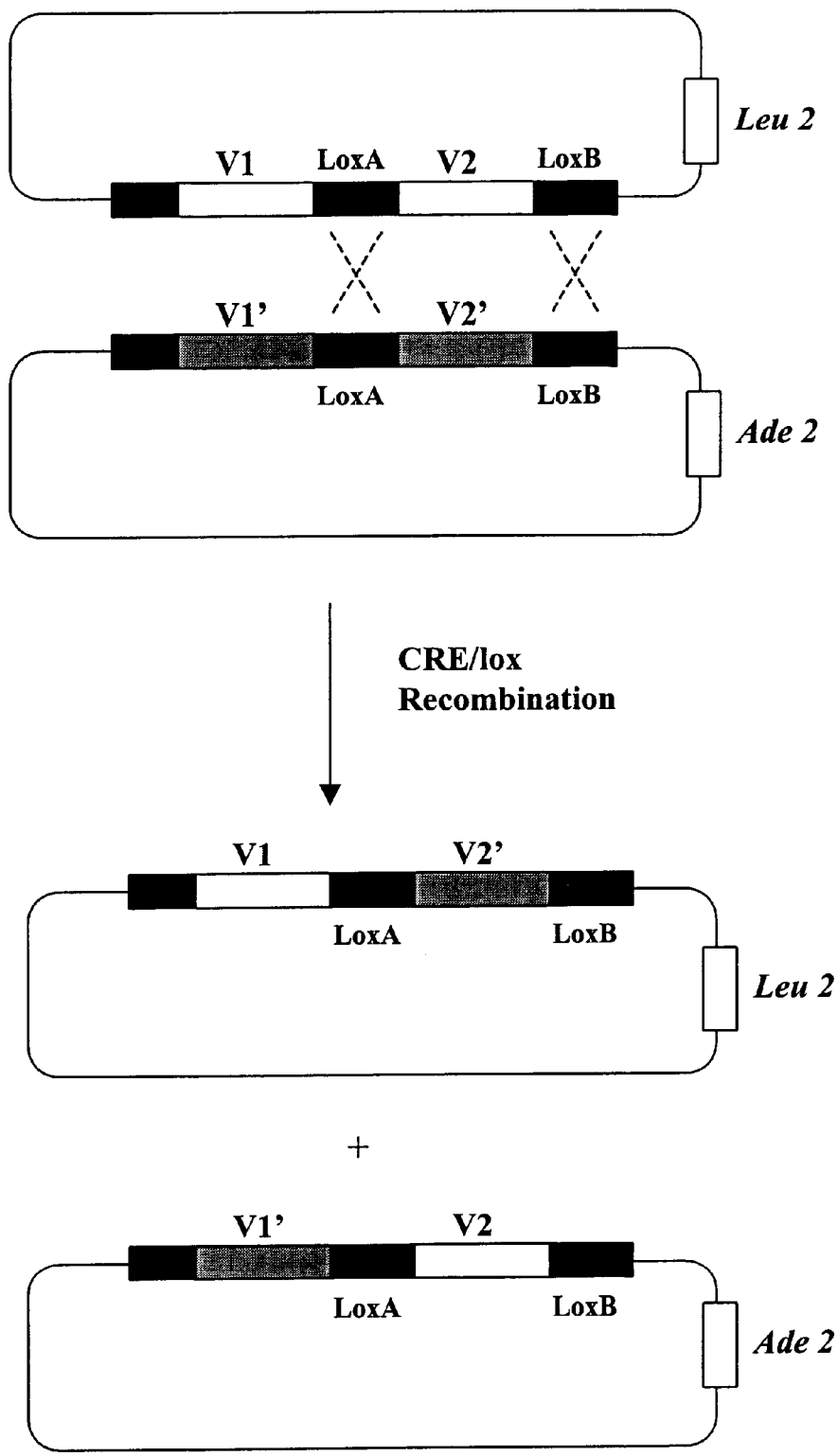
FIG. 4B illustrates a variation of the method illustrated in FIG. 4A where different nutritional markers are included in two libraries of expression vectors.

FIG. 4B illustrates an example of this method. As illustrated in FIG. 4B, two libraries of expression vectors are generated in yeast via homologous recombination by using the procedures described above. The two libraries may be otherwise the same in terms of their source RNA, amplification, and the cloning procedures. The only difference may be the selection marker contained in the vectors.

For example, each of the expression vectors in one library contains Leu 2 as a yeast selection marker, while the other contains Ade 2 as a yeast selection marker. Similar to the method illustrated in FIG. 4A, in the expression vectors in both of two libraries, the recombination sites in the 5' and the 3' flanking sequences of V2 are of different lox sites, loxA and loxB. In the presence of CRE recombinase, the Leu 2-containing expression vector having the lox sites in the 5' (loxA) and 3' (loxB) flanking sequence of V2 (or V1) undergoes a "chain-shuffling" with the Ade 2-containing expression vector having the same lox sites in the 5' and 3' flanking sequence of V2' (or V1'), respectively. As a result, the V2 chain of the expression vector is replaced with the V2' chain of another expression vector, thereby increasing the complexity of the library from $10^n$ on to $10^n \times 10^n = 10^{2n}$ theoretically.

A combined library of both Leu 2- and Ade 2-containing expression vectors are used to transform yeast cells, such as Y187 cells. By Leucine and Adenine complementation in the yeast, transformants are plated in a selection medium such as SD/-Leu/-Ade medium for selecting both types of library plasmids. Any yeast colonies formed on this double selection medium must have transformed by both types of library clones.

Through the selection of both markers it may be ensured that every yeast cell have both types of library clones (each may have with multiple copies). The activation or expression of CRE enzyme in the yeast will allow the Lox P-mediated recombination.

The present invention also provides a method of producing a library of single chain antibodies. In an embodiment, the method comprises: expressing in yeast cells a library of yeast expression vectors. Each of the yeast expression vector comprises a first nucleotide sequence encoding an antibody heavy chain variable region, a second nucleotide sequence encoding an antibody light chain variable region, and a linker sequence encoding a linker peptide that links the antibody heavy chain variable region and the antibody light chain variable region. The antibody heavy chain variable region, the antibody light chain variable region, and the linker peptide are expressed as a single fusion protein. Also, the first and second nucleotide sequences each independently varies within the library of expression vectors to generate a library of single-chain antibodies with a diversity of at least $10^6$.

According to the embodiment, the diversity of the library of single-chain antibodies is preferably between $10^6$–$10^{18}$, more preferably between $10^8$–$10^{18}$, and most preferably between $10^{10}$–$10^{18}$.

3. Selection of Affinity Binding Pairs between the Library of Fusion Proteins of the Present Invention and Target Proteins The present invention also provides methods for screening protein-protein or protein-peptide binding pairs in a yeast two-hybrid system.

The two-hybrid system is a selection scheme designed to screen for polypeptide sequences which bind to a predetermined polypeptide sequence present in a fusion protein. Chien et al. (1991) Proc. Natl. Acad. Sci. (USA) 88: 9578). This approach identifies protein-protein interactions in vivo through reconstitution of a transcriptional activator. Fields and Song (1989) Nature 340: 245), the yeast Gal 4 transcription protein. The method is based on the properties of the yeast Gal 4 protein, which consists of separable domains responsible for DNA-binding and transcriptional activation. Polynucleotides encoding two hybrid proteins, one consisting of the yeast Gal 4 DNA-binding domain (BD) fused to a polypeptide sequence of a known protein and the other consisting of the Gal4 activation domain (AD) fused to a polypeptide sequence of a second protein, are constructed and introduced into a yeast host cell. Intermolecular binding between the two fusion proteins reconstitutes the Gal4 DNA-binding domain with the Gal4 activation domain, which leads to the transcriptional activation of a reporter gene (e.g., lacZ, HIS3) which is operably linked to a Gal4 binding site.

Typically, the two-hybrid method is used to identify novel polypeptide sequences which interact with a known protein. Silver and Hunt (1993) Mol. Biol. Rep. 17: 155; Durfee et al. (1993) Genes Devel. 7; 555; Yang et al. (1992) Science 257: 680; Luban et al. (1993) Cell 73: 1067; Hardy et al. (1992) Genes Devel. 6; 801; Bartel et al. (1993) Biotechniques 14: 920; and Vojtek et al. (1993) Cell 74: 205. The two-hybrid system was used to detect interactions between three specific single-chain variable fragments (scFv) and a specific antigen. De Jaeger et al. (2000) FEBS Lett. 467:316–320. The two-hybrid system was also used to screen against cell surface proteins or receptors such as receptors of hematopoietic super family in yeast. Ozenberger, B. A., and Young, K. H. (1995) "Functional interaction of ligands and receptors of hematopoietic superfamily in yeast" Mol Endocrinol. 9:1321–1329.

Variations of the two-hybrid method have been used to identify mutations of a known protein that affect its binding to a second known protein Li and Fields (1993) FASEB J. 7: 957; Lalo et al. (1993) Proc. Natl. Acad. Sci. (USA) 90: 5524; Jackson et al. (1993) Mol. Cell. Biol. 13; 2899; and Madura et al. (1993) J. Biol. Chem. 268: 12046.

Two-hybrid systems have also been used to identify interacting structural domains of two known proteins or domains responsible for oligomerization of a single protein. Bardwell et al. (1993) Med. Microbiol. 8: 1177; Chakraborty et al. (1992) J. Biol. Chem. 267: 17498; Staudinger et al. (1993) J. Biol. Chem. 268: 4608; and Milne G T; Weaver D T (1993) Genes Devel. 7; 1755; Iwabuchi et al. (1993) Oncogene 8; 1693; Bogerd et al. (1993) J. Virol. 67: 5030).

Variations of two-hybrid systems have been used to study the in vivo activity of a proteolytic enzyme. Dasmahapatra et al. (1992) Proc. Natl. Acad. Sci. (USA) 89: 4159. Alternatively, an E. coli/BCCP interactive screening system was used to identify interacting protein sequences (i.e., protein sequences which heterodimerize or form higher order heteromultimers). Germino et al. (1993) Proc. Natl. Acad. Sci. (U.S.A.) 90: 933; and Guarente L (1993) Proc. Natl. Acad. Sci. (U.S.A.) 90: 1639.

Typically, selection of binding protein using a two-hybrid method relies upon a positive association between two Gal4 fusion proteins, thereby reconstituting a functional Gal4 transcriptional activator which then induces transcription of a reporter gene operably linked to a Gal4 binding site. Transcription of the reporter gene produces a positive readout, typically manifested either (1) as an enzyme activity (e.g., β-galactosidase) that can be identified by a colorimetric enzyme assay or (2) as enhanced cell growth on a defined medium (e.g., HIS3 and Ade 2). Thus, the method is suited for identifying a positive interaction of polypeptide sequences, such as antibody-antigen interactions.

False positives clones that indicate activation of the reporter gene irrespective of the specific interaction between the two hybrid proteins, may arise in the two-hybrid screening. Various procedures have developed to reduce and eliminate the false positive clones from the final positives. For example, 1) prescreening the clones that contains the target vector and shows positive in the absence of the two-hybrid partner (Bartel, P. L., et al. (1993) "Elimination of false positives that arise in using the two-hybrid system" BioTechniques 14:920–924); 2) by using multiple reporters such as His3, β-galactosidase, and Ade2 (James, P. et al. (1996) "Genomic libraries and a host strain designed for highly efficient two-hybrid selection in yeast" Genetics 144:1425–1436); 3) by using multiple reporters each of which is under different GAL 4-responsive promoters such as those in yeast strain Y190 where each of the His 3 and β-Gal reporters is under the control of a different promoter Gal 1 or Gal 10, but both response to Gal 4 signaling (Durfee, T., et al (1993) "The retinoblastoma protein associates with the protein phosphatase type 1 catalytic subunit" Genes Devel. 7:555–569); and 4) by post-screening assays such as testing isolates with target consisting of GAL 4-BD alone.

In addition, the false positive clones may also be eliminated by using unrelated targets to confirm specificity. This is a standard control procedure in the two-hybrid system which can be performed after the library isolate is confirmed by the above-described 1)–4) procedures. Typically, the library clones are confirmed by co-transforming the initially isolated library clones back into the yeast reporter strain with one or more control targets unrelated to the target used in the original screening. Selection is conducted to eliminate those library clones that show positive activation of the reporter gene and thus indicate non-specific interactions with multiple, related proteins.

The present invention provides efficient methods for screening the polypeptide encoded by V1 and V2 in the library of expression vectors for their affinity binding to one or more target proteins.

According to the present invention, the method comprises: expressing a library of tester proteins in yeast cells, each tester protein being a fusion protein comprised of a first polypeptide subunit whose sequence varies within the library, a second polypeptide subunit whose sequence varies within the library independently of the first polypeptide, and a linker peptide which links the first and second polypeptide subunits; expressing one or more target fusion proteins in the yeast cells expressing the tester proteins, each of the target fusion proteins comprising a target peptide or protein; and selecting those yeast cells in which a reporter gene is expressed, the expression of the reporter gene being activated by binding of the tester fusion to the target fusion protein.

According to the method, the diversity of the first or the second polypeptide subunit is preferably between $10^5$–$10^8$, more preferably between $10^4$–$10^8$, and most preferably between $10^5$–$10^8$.

Also according to the method, the diversity of the fusion proteins encoded by the library of expression vectors is preferably between $10^6$–$10^{18}$, more preferably between $10^9$–$10^{18}$, and most preferably between $10^{10}$–$10^{18}$.

A feature of the present invention is that the first and second polypeptide subunits may be selected entirely independent of the target peptide or protein and need not be based on in any way upon one or more proteins known to the bind to the target. As a result, the diversities of the first and second polypeptide subunits may be each independently derived from libraries of precursor sequences that are not specifically designed for the target peptide or protein. For example, the libraries of precursor sequences need not be derived from a small group (e.g. 2–20) of genes with predetermined sequences and encoding proteins that are known to the bind the target peptide or protein.

The diversities of the first and second polypeptide subunits also need not be derived from one or more proteins that are known to bind to the target peptide or protein. For example, the one or more proteins need not be derived from a small group (e.g. 2–20) of proteins with predetermined sequences that are known to bind to the target peptide or protein.

The diversities of the first and second polypeptide subunits also need not be generated by mutagenizing one or more proteins that are known to bind to the target peptide or protein. For example, the first and second polypeptide subunits need not be generated by mutagenizing a small group (e.g. 2–20) of proteins with predetermined sequences and known to bind to the target peptide or protein.

In a variation of the embodiment, a single target fusion protein is expressed and screened against the library of tester proteins. According to the variation, the step of expressing the library of tester fusion proteins may include transforming a library of tester expression vectors into the yeast cells which contain a reporter construct comprising the reporter gene whose expression is under transcriptional control of a transcription activator comprising an activation domain and a DNA binding domain. Each of the tester expression vectors comprises a first transcription sequence encoding either the activation domain AD or the DNA binding domain BD of the transcription activator, a first nucleotide sequence V1 encoding the first polypeptide subunit, a second nucleotide sequence V2 encoding the second polypeptide subunit, and a linker sequence L encoding a linker peptide that links the first nucleotide sequence and the second nucleotide sequence. Optionally, the step of expressing the target fusion proteins includes transforming a target expression vector into the yeast cells simultaneously or sequentially with the library of tester expression vectors. The target expression vector comprises a second transcription sequence encoding either the activation domain AD or the DNA binding domain BD of the transcription activator which is not expressed by the library of tester expression vectors; and a target sequence encoding the target protein or peptide.

Figure 5:
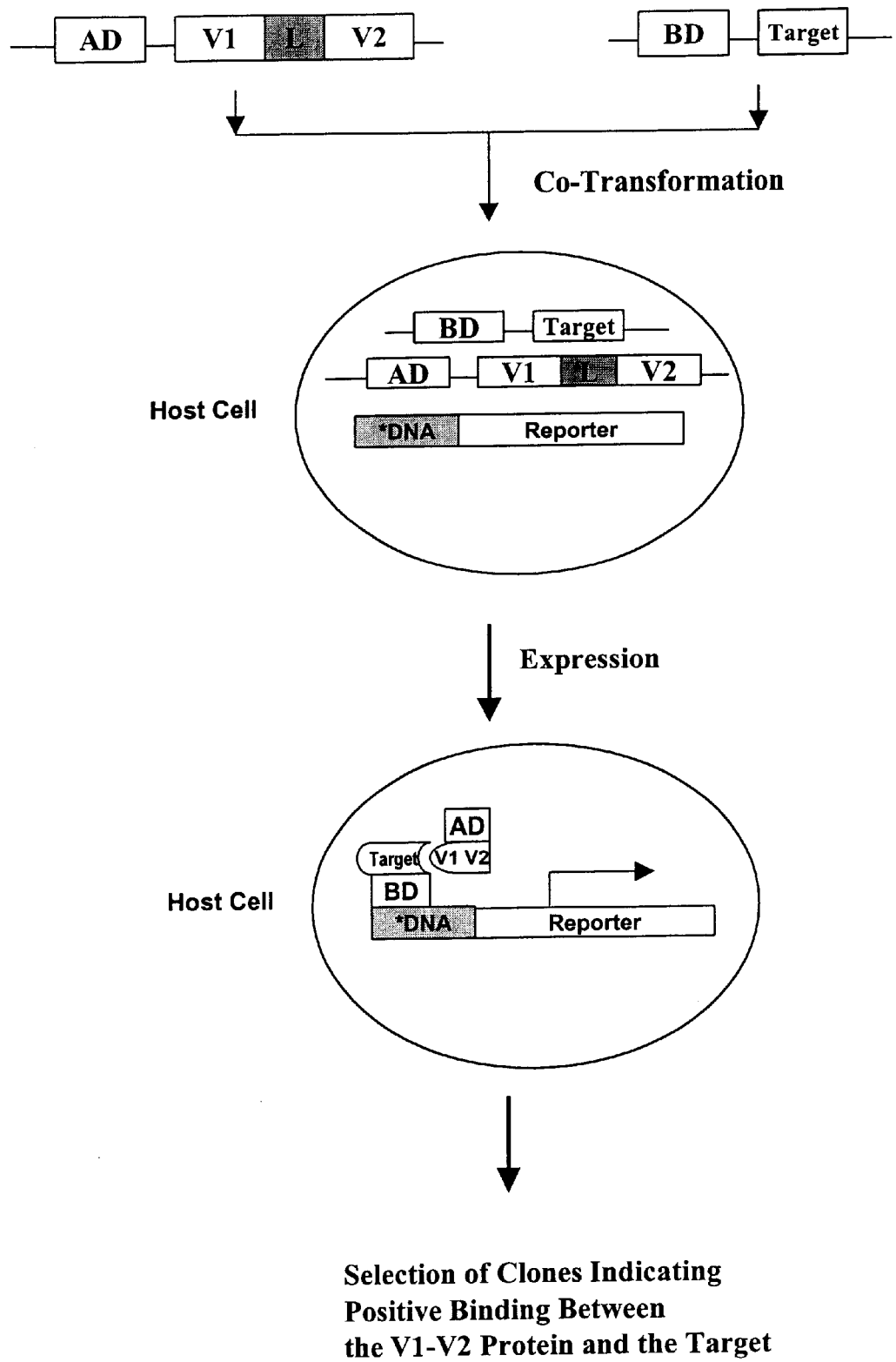
FIG. 5 illustrates an embodiment of a method or selecting protein-protein binding pair in a two-hybrid system where the expression vectors carrying the AD and BD domains are co-transformed into yeast.

FIG. 5 illustrates a flow diagram of a preferred embodiment of the above described method. As illustrated in FIG. 5, the sequence library containing V1 and V2 fused with an AD domain upstream is carried by a library of expression vectors, the AD-V1-V2 vectors. The coding sequence of the target protein (labeled as "Target") is contained in another expression vector and fused with a BD domain, forming the BD-Target vector.

The AD-V1-V2 vector and the BD-Target vector may be co-transformed into a yeast cell by using method known in the art. Gietz, D. et al. (1992) "Improved method for high efficiency transformation of intact yeast cells" Nucleic Acids Res. 20:1425. The construct carrying the specific DNA binding site and the reporter gene (labeled as "Reporter") may be stably integrated into the genome of the host cell or transiently transformed into the host cell. Upon expression of the sequences in the expression vectors, the library of fusion proteins comprising AD, V1 and V2, labeled as the AD-V1-V2 fusion proteins, undergo protein folding in the host cell and adopt various conformations. Some of the AD-V1-V2 fusion proteins may bind to the Target protein expressed by the BD-Target vector in the host cell, thereby bringing the AD and BD domains to a close proximity in the promoter region (i.e., the specific DNA binding site) of the reporter construct and thus reconstituting a functional transcription activator composed of the AD and BD domains. As a result, the AD activates the transcription of the reporter gene downstream from the specific DNA binding site, resulting in expression of the reporter gene, such as the lacZ reporter gene. Clones showing the phenotype of the reporter gene expression are selected, and the AD-V1-V2 vectors are isolated. The coding sequences for V1 and V2 are identified and characterized.

Alternatively, the steps of expressing the library of tester fusion proteins and expressing the target fusion protein includes causing mating between first and second populations of haploid yeast cells of opposite mating types. The first population of haploid yeast cells comprises a library of tester expression vectors for the library of tester fusion proteins. Each of the tester expression vector comprises a first transcription sequence encoding either the activation domain AD or the DNA binding domain BD of the transcription activator, a first nucleotide sequence V1 encoding the first polypeptide subunit, a second nucleotide sequence V2 encoding the second polypeptide subunit, and a linker sequence L encoding a linker peptide that links the first nucleotide sequence V1 and the second nucleotide sequence V2. The second population of haploid yeast cells comprises a target expression vector. The target expression vector comprises a second transcription sequence encoding either the activation domain AD or the DNA binding domain BD of the transcription activator which is not expressed by the library of tester expression vectors; and a target sequence encoding the target protein or peptide. Either the first or second population of haploid yeast cells comprises a reporter construct comprising the reporter gene whose expression is under transcriptional control of the transcription activator.

In this method, the haploid yeast cells of opposite mating types may preferably be α and a type strains of yeast. The mating between the first and second populations of haploid yeast cells of α and a type strains may be conducted in a rich nutritional culture medium.

Figure 6:
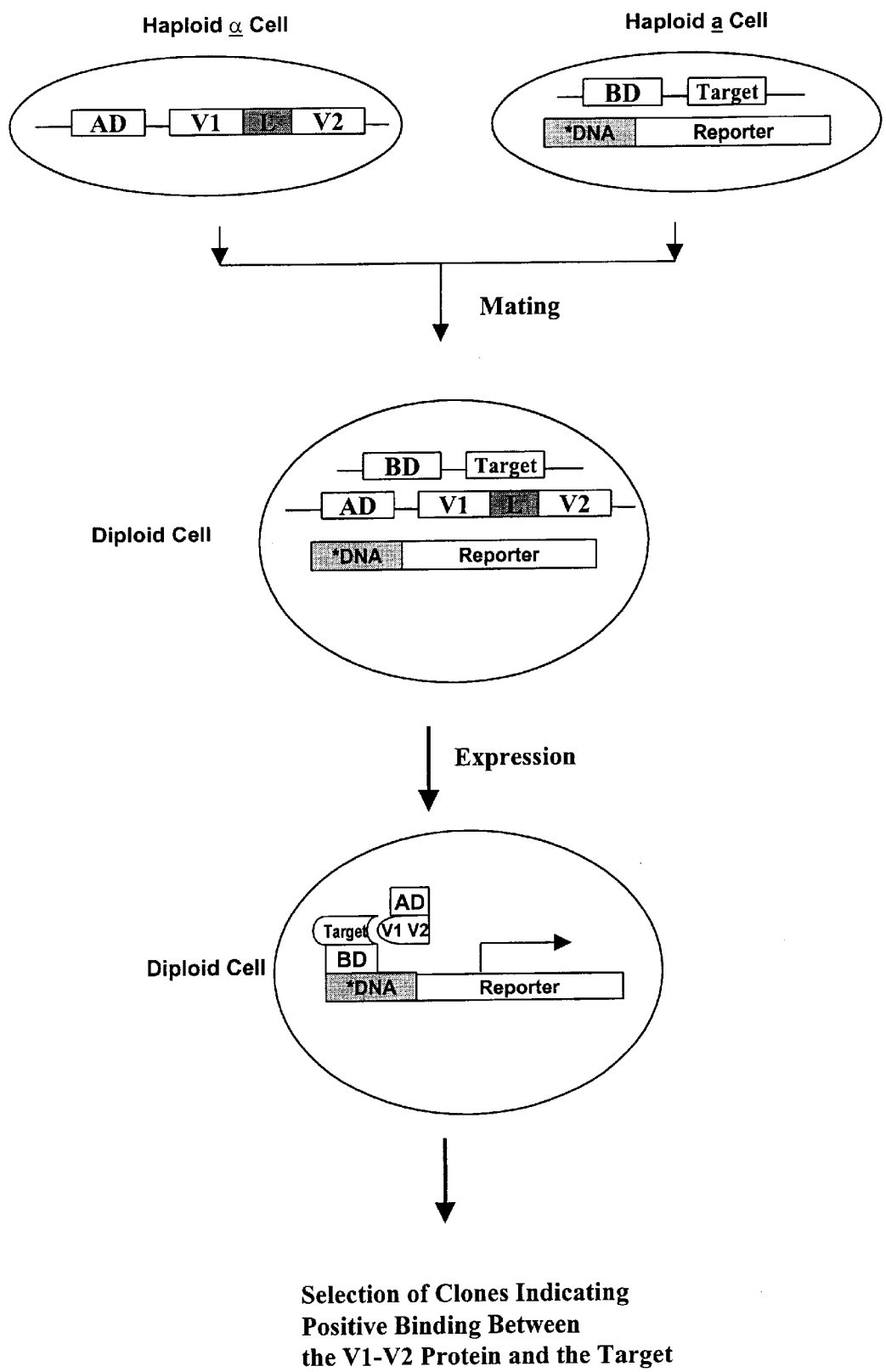
FIG. 6 illustrates an embodiment of the method for selecting protein-protein binding pairs in a two-hybrid system where the expression vectors carrying the AD and BD domains are introduced into diploid yeast cells via mating between two haploid yeast strains.

FIG. 6 illustrates a flow diagram of a preferred embodiment of the above described method. As illustrated in FIG. 6, the sequence library containing V1 and V2 fused with an AD domain upstream is carried by a library of expression vectors, the AD-V1-V2 vectors. The library of the AD-V1-V2 vectors are transformed into haploid yeast cells such as the a type strain of yeast.

The coding sequence of the target protein (labeled as "Target") is contained in another expression vector and fused with a BD domain, forming the BD-Target vector. The BD-Target vector is transformed into haploid cells of opposite mating type of the haploid cells containing the the AD-V1-V2 vectors, such as the α type strain of yeast. The construct carrying the specific DNA binding site and the reporter gene (labeled as "Reporter") may be transformed into the haploid cells of either the type a or type α strain of yeast.

The haploid cells of the type a and type α strains of yeast are mated under suitable conditions such as low speed of shaking in liquid culture, physical contact in solid medium culture, and rich medium such as YPD. Bendixen, C. et al. (1994) "A yeast mating-selection scheme for detection of protein-protein interactions", Nucleic Acids Res. 22: 1778–1779. Finley, Jr., R. L. & Brent, R. (1994) "Interaction mating reveals lineary and ternery connections between Drosophila cell cycle regulators", Proc. Natl. Acad. Sci. USA, 91:12980–12984. As a result, the AD-V1-V2, the BD-Target expression vectors and the Reporter construct are taken into the parental diploid cells of the a and type α strain of haploid yeast cells.

Upon expression of the sequences in the expression vectors in the parental diploid cells, the library of fusion proteins comprising AD, V1 and V2, labeled as the AD-V1-V2 fusion proteins, undergo protein folding in the host cell and adopt various conformations. Some of the AD-V1-V2 fusion proteins may bind to the Target protein expressed by the BD-Target vector in the parental diploid cell, thereby bringing the AD and BD domains to a close proximity in the promoter region (i.e., the specific DNA binding site) of the reporter construct and thus reconstituting a functional transcription activator composed of the AD and BD domains. As a result, the AD activates the transcription of the reporter gene downstream from the specific DNA binding site, resulting in expression of the reporter gene, such as the lacZ reporter gene. Clones showing the phenotype of the reporter gene expression are selected, and the AD-V1-V2 vectors are isolated. The coding sequences for V1 and V2 are identified and characterized.

A wide variety of reporter genes may be used in the present invention. Examples of proteins encoded by reporter genes include, but are not limited to, easily assayed enzymes such as β-galactosidase, α-galactosidase, luciferase, β-glucuronidase, chloramphenicol acetyl transferase (CAT), secreted embryonic alkaline phosphatase (SEAP), fluorescent proteins such as green fluorescent protein (GFP), enhanced blue fluorescent protein (EBFP), enhanced yellow fluorescent protein (EYFP) and enhanced cyan fluorescent protein (ECFP); and proteins for which immunoassays are readily available such as hormones and cytokines. The expression of these reporter genes can also be monitored by measuring levels of mRNA transcribed from these genes.

When the screening of the V1 and V2 library is conducted in yeast cells, certain reporter(s) are of nutritional reporter which allows the yeast to grow on the specific selection medium plate. This is a very powerful screening process, as has been shown by many published papers. Examples of the nutritional reporter include, but are not limited to, His3, Ade2, Leu2, Ura3, Trp1 and Lys2. The His3 reporter is described in Bartel, P. L. et al. (1993) "Using the two-hybrid system to detect protein-protein interactions", in Cellular interactions in Development: A practical approach, ed. Hastley, D. A., Oxford Press, pages 153–179. The Ade2 reporter is described in Jarves, P. et al. (1996) "Genomic libraries and a host strain designed for highly efficient two-hybrid selection in yeast" Genetics 144:1425–1436.

For example, a library of scFV expression vectors that contains the $V_H$ and $V_L$ fused with an AD domain of GAL 4 transcription activator (the AD-scFv library) may be transformed into haploid cells of the α mating type of yeast strain. A BD domain of GAL 4 transcription activator is fused with the sequence encoding the target protein to be selected against the scFV library in a plasmid. This plasmid is transformed into haploid cells of the a mating type of yeast strain.

Equal volume of AD-scFv library-containing yeast stain (α-type) and the BD-target-containing yeast strain (a-type) are inoculated into selection liquid medium and incubated separately first. These two cultures are then mixed and allowed to grow in rich medium such as 1×YPD and 2×YPD. Under the rich nutritional culture condition, the two haploid yeast strains will mate and form diploid cells. At the end of this mating process, these yeast cells are plated into selection plates. A multiple-marker selection scheme may be used to select yeast clones that show positive interaction between the scFVs in the library and the target. For example, a scheme of SD/-Leu-Trp-His-Ade may be used. The first two selections (Leu-Trp) are for markers (Leu and Trp) expressed from the AD-scFv library and the BD-Target vector, respectively. Through this dual-marker selection, diploid cells retaining both BD and AD vectors in the same yeast cells are selected. The latter two markers, His-Ade, are used to screen for those clones that express the reporter gene from parental strain, presumably due to affinity binding between the scFVs in the library and the target.

After the screening by co-transformation, or by mating screening as described above, the putative interaction between the gene probe and the library clone isolates can be further tested and confirmed in vitro or in vivo.

In vitro binding assays may be used to confirm the positive interaction between the tested protein expressed by the clone isolate and the target protein or peptide. For example, the in vitro binding assay may be a "pull-down" method, such as using GST (glutathione S-transferase)-fused gene probe as matrix-binding protein, and with in vitro expressed library clone isolate that are labeled with a radioactive or non-radioactive group. While the probe is bound to the matrix through GST affinity substrate (glutathione-agarose), the library clone isolate will also bind to the matrix through its affinity with the gene probe. The in vitro binding assay may also be a Co-immunoprecipitation (Co-IP) method using two affinity tag antibodies. In this assay, both the target gene probe and the library clone isolate are in vitro expressed fused with peptide tags, such as HA (haemaglutinin A) or Myc tags. The gene probe is first immuno-precipitated with an antibody against the affinity peptide tag (such as HA) that the target gene probe is fused with. Then the second antibody against a different affinity tag (such as Myc) that is fused with the library clone isolate is used for reprobing the precipitate.

In vivo assays may also be used to confirm the positive interaction between the tested protein expressed by the clone isolate and the target protein or peptide. For example, a mammalian two-hybrid system may serve as a reliable verification system for the yeast two-hybrid library screening. In this system, the target gene probe and library clone are fused with Gal 4 DNA-binding domain or an mammalian activation domain (such as VP-16) respectively. These two fusion proteins under control of a strong and constitutive mammalian promoter (such as CMV promoter) are introduced into mammalian cells by transfection along with a reporter responsive to Gal 4. The reporter can be CAT gene (chloramphenical acetate transferase) or other commonly used reporters. After 2–3 days of transfection, CAT assay or other standard assays will be performed to measure the strength of the reporter which is correlated with the strength of interaction between the gene probe and the library clone isolate.

The present invention also provides a kit for selecting selecting tester proteins capable of binding to a target peptide or protein.

In an embodiment, the kit comprises: a library of tester expression vectors and a yeast cell line. Each of the tester expression vectors comprises a first transcription sequence encoding either an activation domain or a DNA binding domain of a transcription activator, a first nucleotide sequence encoding a first polypeptide subunit, a second nucleotide sequence encoding a second polypeptide subunit, and a linker sequence encoding a linker peptide that links the first nucleotide sequence and the second nucleotide sequence. The first and second nucleotide sequences each independently varies within the library of expression vectors. A reporter construct may be contained in the yeast cell line. The reporter construct comprises a reporter gene whose expression is under a transcriptional control of a specific DNA binding site.

Optionally, the kit may further comprise a target expression vector which comprises a second transcription sequence encoding either the activation domain or the DNA binding domain of the transcription activator which is not expressed by the library of tester expression vectors; and a target sequence encoding the target protein or peptide.

In another embodiment, the kit comprises: a first and second populations of haploid yeast cells of opposite mating types. The first population of haploid yeast cells comprises a library of tester expression vectors for the library of tester fusion proteins. Each of the tester expression vector comprises a first transcription sequence encoding either an activation domain or a DNA binding domain of a transcription activator, a first nucleotide sequence encoding a first polypeptide subunit, a second nucleotide sequence encoding a second polypeptide subunit, and a linker sequence encoding a linker peptide that links the first nucleotide sequence and the second nucleotide sequence. The second population of haploid yeast cells comprises a target expression vector. The target expression vector encodes either the activation domain or the DNA binding domain of the transcription activator which is not expressed by the library of tester expression vectors; and a target sequence encoding the target protein or peptide. Either the first or second population of haploid yeast cells comprises a reporter construct comprising a reporter gene whose expression is under transcriptional control of the transcription activator.

Optionally, the second population of haploid yeast cells comprises a plurality of target expression vectors. Each of the target expression vectors encodes either the activation domain or the DNA binding domain of the transcription activator which is not expressed by the library of tester expression vectors; and a target sequence encoding the target protein or peptide. Either the first or second population of haploid yeast cells comprises a reporter construct comprising a reporter gene whose expression is under transcriptional control of the transcription activator.

4. Selection of Affinity Binding Pairs between the Library of Fusion Proteins of the Present Invention and Target Nucleic Acids As described above, the libraries of V1 and V2 sequences of the present invention can be used for selecting protein-protein or protein-peptide binding pairs against single or arrayed multiple protein/peptide targets in a two-hybrid screening system. As described in the following, these libraries can also be used for selecting protein-DNA or protein-RNA binding pairs in an one-hybrid system or three-hybrid system, respectively.

The general scheme for screening protein-DNA binding pair using an one-hybrid system is described in Li and Herskowitz (1993) Science 262:1870–1874. Typically, this method is used to identify genes encoding proteins that recognize a specific DNA sequence. A library of random protein segments tagged with a transcriptional activation domain (AD) is screened for proteins that can activate a reporter gene containing the specific DNA sequence in its promoter region. By using this strategy, an essential protein that interacts in vivo with the yeast origin of DNA replication was identified. In a three-hybrid system, the target nucleic acid is RNA or RNA-associated proteins. SanGupta, et al. (1996) Proc. Natl. Acad. Sci. USA 93:8496–8501.

The present invention provides a method is provided for screening protein-DNA binding pairs in a yeast one-hybrid system.

In an embodiment, the method comprises: expressing a library of tester fusion proteins in yeast cells which contain a reporter construct comprising a reporter gene whose expression is under a transcriptional control of a target DNA sequence; and selecting the yeast cells in which the reporter gene is expressed, the expression of the reporter gene being activated by binding of the tester fusion protein to the target DNA sequence. Each of the tester fusion proteins comprises an activation domain AD of a transcription activator, a first polypeptide subunit whose sequence varies within the library, a second polypeptide subunit, whose sequence varies within the library independently of the first polypeptide subunit, and a linker peptide that links the first polypeptide subunit to the second polypeptide subunit.

In a variation of the embodiment, the step of expressing the library of tester fusion proteins includes transforming into the yeast cells a library of tester expression vectors for the library of tester fusion proteins. Each of the tester expression vectors comprises a transcription sequence encoding the activation domain AD of the transcription activator, a first nucleotide sequence V1 encoding the first polypeptide subunit, a second nucleotide sequence V2 encoding the second polypeptide subunit, and a linker sequence L encoding a linker peptide that links the first nucleotide sequence V1 and the second nucleotide sequence V2.

In another variation of the embodiment, the step of expressing a library of tester fusion proteins in yeast cells includes causing mating between a first and second populations of haploid yeast cells of opposite mating types. The first population of haploid yeast cells comprises a library of tester expression vectors for the library of tester fusion proteins, each tester expression vector comprising a transcription sequence encoding the activation domain AD of the transcription activator, a first nucleotide sequence V1 encoding the first polypeptide subunit, a second nucleotide sequence V2 encoding the second polypeptide subunit, and a linker sequence L encoding a linker peptide that links the first nucleotide sequence V1 and the second nucleotide sequence V2. The second population of haploid yeast cells comprises the reporter construct.

According to the variation, the haploid yeast cells of opposite mating types may preferably be α and a type strains of yeast. The mating between the first and second populations of haploid yeast cells of α and a type strains may preferably conducted in a rich nutritional culture medium.

According to any of the above-described methods for selecting protein-DNA binding pairs, the target DNA sequence in the reporter construct may preferably be positioned in 2–6 tandem repeats 5' relative to the reporter gene.

The target DNA sequence in the reporter construct may be preferably between about 15–75 bp in length and more preferably between about 25–55 bp in length.

Figure 7:
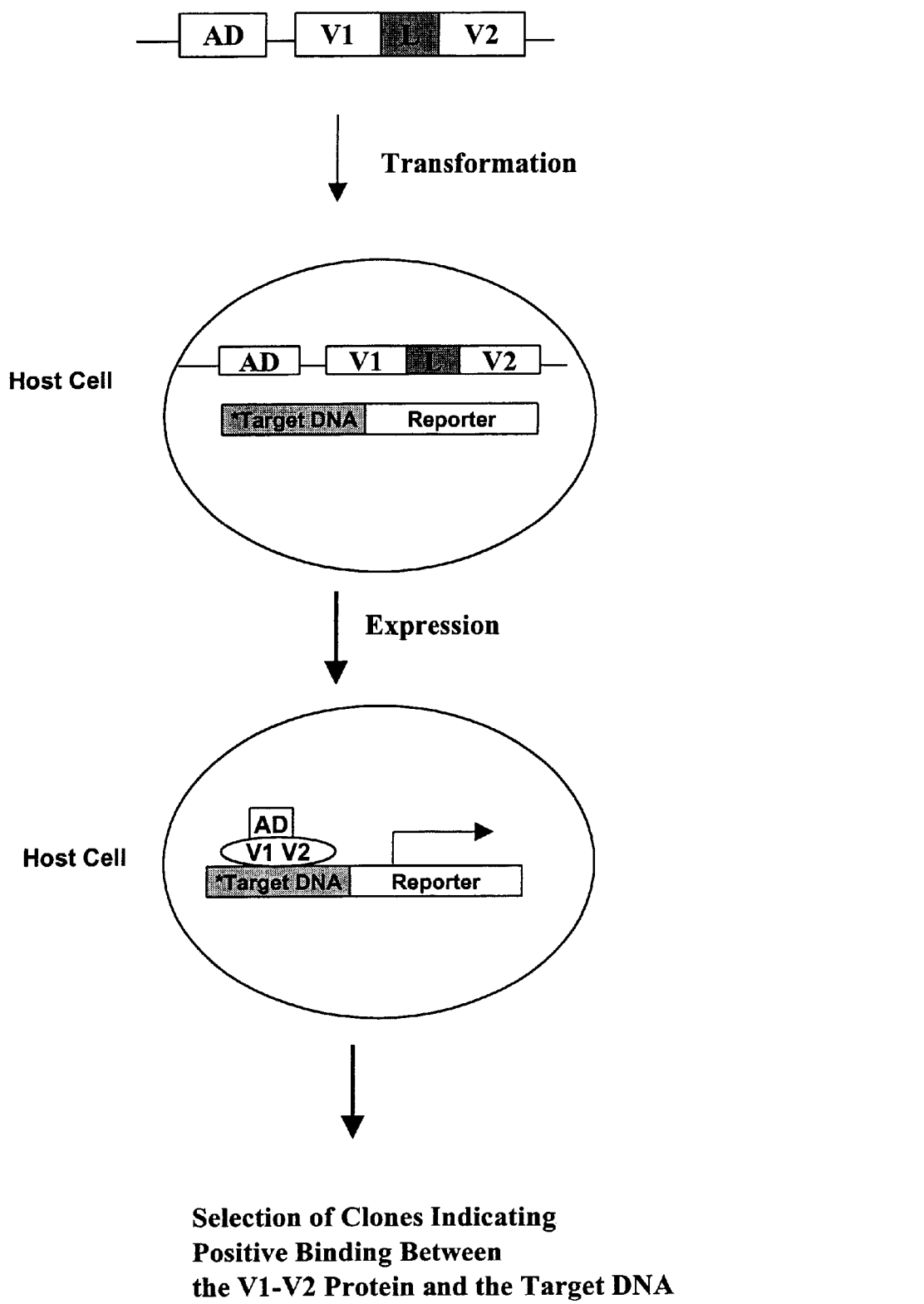
FIG. 7 illustrates an embodiment of a method for selecting protein-DNA binding pair in a one-hybrid system where the expression vector carrying the AD domain is transformed into yeast.

FIG. 7 illustrates a flow diagram of a preferred embodiment of the above-described method. As illustrated in FIG. 7, the tester sequence library containing V1 and V2 fused with an AD domain upstream is carried by a library of expression vectors, the AD-V1-V2 vector. The target DNA sequence (labeled "Target DNA") is positioned in the promoter region of a reporter gene (labeled "Reporter").

The AD-V1-V2 vector is transformed into a yeast cell by using methods known in the art. Gietz, D. et al. (1992) "Improved method for high efficiency transformation of intact yeast cells" Nucleic Acids Res. 20:1425. The construct carrying the target DNA sequence and the reporter gene may be stably integrated into the genome of the host cell or transiently transformed into the host cell.

As illustrated in FIG. 7, upon expression of the tester sequences in the expression vectors, the library of tester proteins comprising AD, V1 and V2, labeled as the AD-V1-V2 fusion proteins, undergo protein folding in the host cell and adopt various conformations. Some of the AD-V1-V2 fusion proteins may bind to the target DNA sequence in the promoter region of the reporter gene, thereby bringing the AD domain to a close proximity in the promoter region. As a result, the AD activates the transcription of the reporter gene downstream from the target DNA sequence, resulting in expression of the reporter gene, such as the lacZ reporter gene. Clones showing the phenotype of the reporter gene expression are selected, and the AD-V1-V2 vectors are isolated. The coding sequences for V1 and V2 are identified and characterized.

Alternatively, the AD-V1-V2 vector and the reporter construct may be introduced a diploid yeast cell by mating between two haploid yeast strains. For example, the AD-V1-V2 vector may be transformed into a haploid yeast strain such as the α strain; and the reporter construct may be transformed into another haploid yeast strain such as the s the a strain. Upon mating between these two haploid strains, diploid cells are formed to merge the genetic materials carried by the two haploid cells. As a result, the AD-V1-V2 vector and the reporter construct are introduced into a diploid cell which is then screened for positive interactions between the tester protein and the target DNA in the cell.

The target DNA sequence may be a regulatory element, or a putative chromosome remodeling protein complex opening site, preferably in a short stretch of DNA sequence (20–80 bp). The target DNA sequence may be cloned into a yeast one-hybrid system reporter vector, e.g., pHIS (Clontech, Palo Alto, Calif.; Luo et al. (1996) "Cloning and analysis of DNA-binding proteins by yeast one-hybrid and one-two-hybrid system" Biotechniques 20:564–568). To increase the sensitivity, the target sequence may be cloned as in a few tandem repeats (e.g., 4–5 copies) into the reporter vector. The recombinant reporter vector may be integrated into the yeast reporter strain by a transformation with linearized vector and selection for rescuing the integration marker. The integration should be at a single chromosome location and usually at high efficiency.

The tester sequence library containing V1 and V2 may encode a library of scFv that can be used to screen against a target DNA antigen. The scFv expression library may be introduced into yeast by transformation or by mating with the yeast strain of the opposite mating type and harboring the reporter construct. The transformation and mating procedures are described in detail in Example 3. Pre-screening of self-activating clones may be necessary for eliminating the false positive clones. The procedures are similar to the two-hybrid library pre-screening described in Section 3.

The library clones isolated from such a one-hybrid system screening may indicate that scFv antibody(s) expressed from these clones are capable of binding to the DNA target. Such antibody may be have significant applications in DNA vaccine and diagnostics of diseases.

The one-hybrid system of the present invention may also be modified to screen for novel co-factors that bind to a known DNA-binding factor. The library of polypeptides comprising V1 and V2 subunits fused with an AD domain may be screened for affinity binding toward a specific factor that binds to a DNA sequence in the promoter region of a reporter gene.

In one embodiment, the method comprises: expressing a library of tester fusion proteins in yeast cells which contain a reporter construct comprising a reporter gene whose expression is under a transcriptional control of a specific DNA binding site; expressing a target protein in the yeast cells expressing the tester fusion proteins, where the target protein binds to the specific DNA binding site; and selecting the yeast cells in which the reporter gene is expressed, the expression of the reporter gene being activated by binding of the tester fusion protein to the target protein. Each of the tester fusion proteins comprises an activation domain AD of a transcription activator, a first polypeptide subunit, a second polypeptide subunit, and a linker peptide that links the first polypeptide subunit to the second polypeptide subunit, wherein the sequences of the first and second polypeptide subunits each independently varies within the library of the tester fusion protein.

In a variation of the embodiment, the step of expressing the library of tester fusion proteins includes transforming into the yeast cells a library of tester expression vectors for the library of tester fusion proteins. Each of the tester expression vectors comprises a transcription sequence encoding the activation domain AD of the transcription activator, a first nucleotide sequence V1 encoding the first polypeptide subunit, a second nucleotide sequence V2 encoding the second polypeptide subunit, and a linker sequence L encoding a linker peptide that links the first nucleotide sequence V1 and the second nucleotide sequence V2.

In another variation of the embodiment, the steps of expressing the library of tester fusion proteins and expressing the target fusion protein includes causing mating between a first and second populations of haploid yeast cells of opposite mating types. The first population of haploid yeast cells comprises a library of tester expression vectors for the library of tester fusion proteins. Each of the tester expression vectors comprises a transcription sequence encoding the activation domain AD of the transcription activator, a first nucleotide sequence V1 encoding the first polypeptide subunit, a second nucleotide sequence V2 encoding the second polypeptide subunit, and a linker sequence L encoding a linker peptide that links the first nucleotide sequence V1 and the second nucleotide sequence V2. The second population of haploid yeast cells comprises a target expression vector comprising a target sequence encoding the target protein. Either the first or second population of haploid yeast cells comprises the reporter construct.

Figure 8:
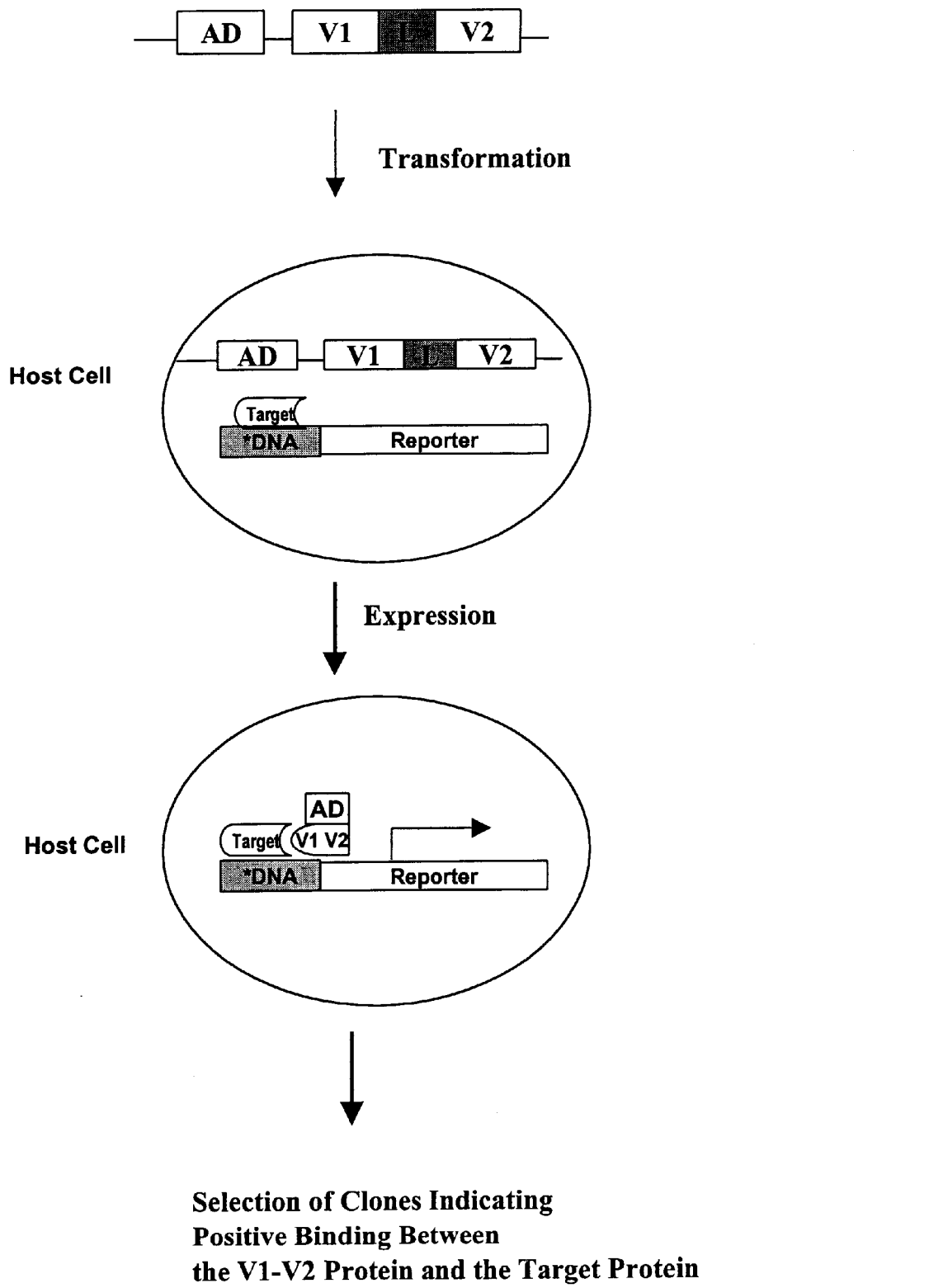
FIG. 8 illustrates an embodiment of the method for selecting protein-protein binding pairs in a one-hybrid system where the expression vector carrying the AD domain is transformed into yeast.

FIG. 8 illustrates a flow diagram of a preferred embodiment of the above-described method. As illustrated in FIG. 8, the tester sequence library containing V1 and V2 fused with an AD domain upstream is carried by a library of expression vectors, the AD-V1-V2 vector. The AD-V1-V2 vectors are introduced into host cells, for example, by transformation. The target protein (labeled "Target") that is known to bind to a specific DNA sequence may be expressed by an expression vector in the host cells or otherwise present in the cells. The specific DNA sequence (labeled "*DNA") is positioned in the promoter region of a reporter gene (labeled "Reporter"). The construct carrying the specific DNA sequence and the reporter gene may be stably integrated into the genome of the host cell or transiently transformed into the host cell.

As illustrated in FIG. 8, upon expression of the tester sequences in the expression vectors, the library of tester proteins comprising AD, V1 and V2, labeled as the AD-V1-V2 fusion proteins, undergo protein folding in the host cell and adopt various conformations. Some of the AD-V1-V2 fusion proteins may bind to the target protein that binds to the specific DNA sequence in the promoter region of the reporter gene, thereby bringing the AD domain to a close proximity in the promoter region. As a result, the AD activates the transcription of the reporter gene downstream from the target DNA sequence, resulting in expression of the reporter gene, such as the lacZ reporter gene. Clones showing the phenotype of the reporter gene expression are selected, and the AD-V1-V2 vectors are isolated. The coding sequences for V1 and V2 are identified and characterized.

The specific target protein may be any protein that has been characterized to be a DNA-binding fact by using various assays such as in vitro gel shifting assays, or through conventional one-hybrid screening. The target protein (without being fused to an AD domain) may be expressed in the yeast one-hybrid reporter strain. The level of target protein expression is then adjusted to such an extent that no measurable activation is observed. The yeast strain may also contain the reporter construct that is integrated into the yeast genome.

The tester sequence library containing V1 and V2 may encode a library of scFv that can be used to screen against a target protein that a DNA-binding factor. The library clones isolated from such a modified one-hybrid system screening may indicate that scFv antibody(s) expressed from these clones are capable of binding to the protein target. Such antibody may be have significant applications in therapeutics and diagnostics of diseases.

5. High Throughput Selection of Affinity Binding Pairs between the Library of Fusion Proteins of the Present Invention and a Library of Target Proteins The present invention also provides a method for high throughput screening of the above-described libraries of fusion proteins encoded by V1and V2. The library of expression vectors, for example, the AD-scFv yeast expression vector library, may be screen for the binding of the scFvs to multiple target proteins expressed by a yeast clone library (BD-Target library), each clone carrying a BD-Target vector for each target protein to be selected against. The BD-Target clone library may be arrayed in multiple-well plates, such as 96- and 384-well plates, and then screened against the scFv library in an automated and high throughput manner.

For example, a collection of EST clones (or a total library of EST) from human, mouse or other organisms may be screened against the scFv library generated by using the methods of the present invention. Such a collection of EST clones may be ordered from a public resource in a library format with individually clones arrayed in 96-well or 384-well plates. Lennon, G. et al. (1996) "The I.M.A.G.E. Consortium: an integrated molecular analysis of genomes and their expression" Genomics 33:151–152. The EST inserts from the original collection (usually in bacterial cloning and sequencing vectors) may be PCR amplified with extended homologous sequences at both ends following similar procedures used in the generation of the scFv library. Through the same homologous recombination procedure as used in the generation of the scFv library, the EST inserts are inserted into an expression vector containing a BD domain of a transcription activator in yeast cells.

Optionally, a collection of certain domain structures, such as zinc finger and helix-loop-helix protein domains, may be inserted into the AD-containing expression vector in yeast cell via homologous recombination. The yeast clones containing the vector with BD fused to each domain structure may be arrayed in multiple-well plates and screened against the scFv library for affinity binding between the scFv and each domain structure. The domain structure may be 18–20 amino acids at length and its sequence may not be totally random. Such a collection of domain structures may be generated by using synthetic oligonucleotides with characteristic conserved and random/degenerate residues to cover most of the rational domain structures.

Also optionally, the coding sequences of a random peptide library may be inserted into the BD-containing expression vector in yeast cell via homologous recombination. The yeast clones containing the vector with AD fused to each random peptide may be arrayed in multiple-well plates and screened against the scFv library for affinity binding between the scFv and each random peptide target. The random peptide may be 16–20 amino acid at length. Such a library of random peptide can generated by random oligonucleotide synthesis or by partially random oligonucleotide synthesis biased toward a sequence encoding a specific target.

Alternatively, a library of short peptides may also be may be inserted into the BD-containing expression vector in yeast cell via homologous recombination. Accordingly, the scFv library may be fused with the AD domain in the expression vector and screened against this library of short peptide. Through this selection, peptide ligands may be selected for each scFv. Strutural and functional analysis of the selected peptides should aid in the rational design of antigens and structural improvement of specific target antigens.

Figure 9:
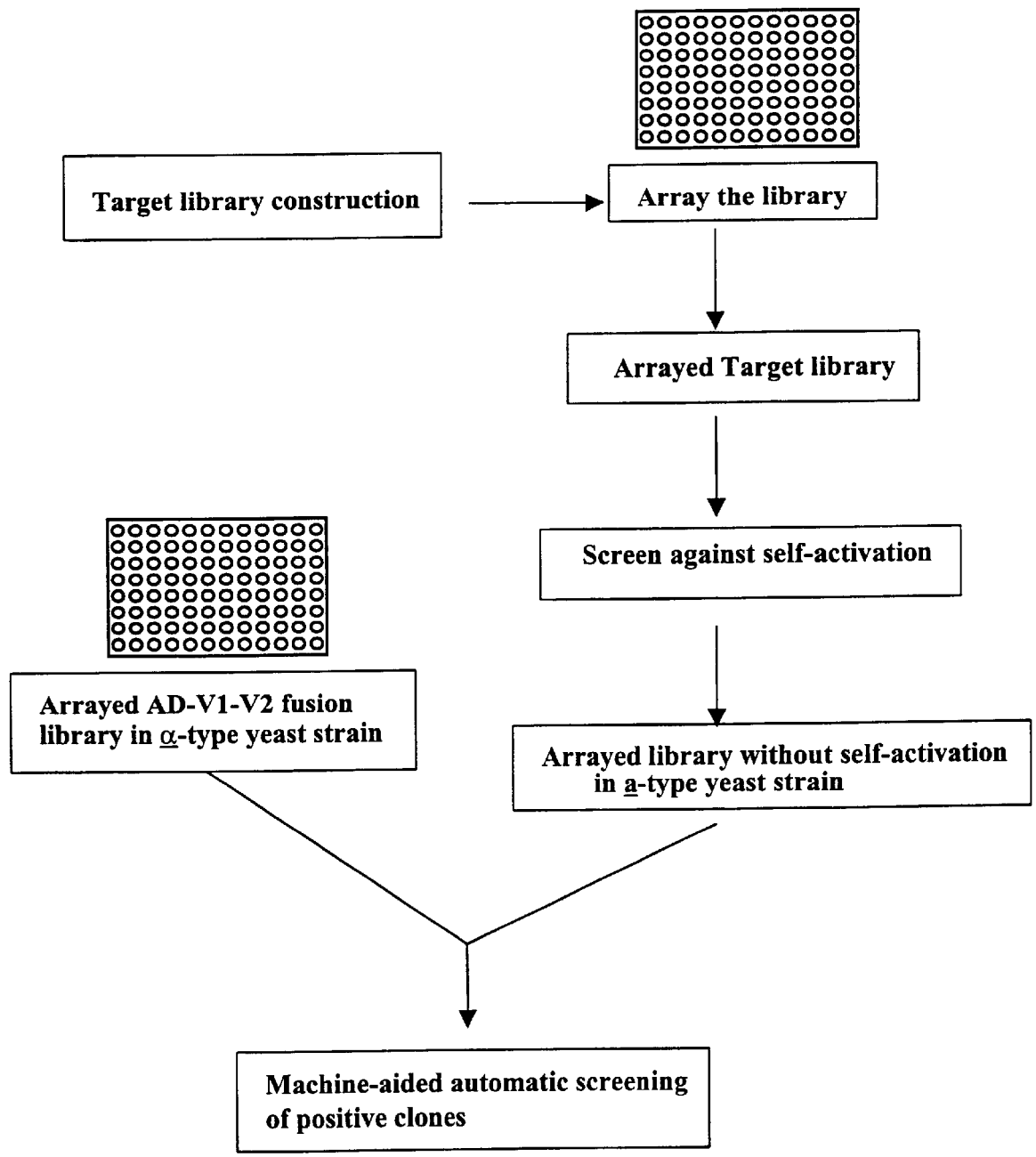
FIG. 9 illustrates an embodiment of a high throughput method for selecting protein-protein binding pairs in a two-hybrid system where the library of the tester expression vectors and the library of expression vector carrying the target expression vectors are each arrayed in multi-well plates.

FIG. 9 depicts a general scheme of high throughput screening of the scFv library against a library of target proteins in yeast via mating of two strains of yeast haploid cells.

As illustrated in FIG. 9, the each member of the library of target proteins or peptides is fused with the DB domain of an expression vector contained in yeast a-type of host strain.

The yeast clones of the library of target proteins may be arrayed as a clone library. This may be achieved by depositing each clone containing the BD-Target fusion into a well of a 96- or 384-well plate. Optionally, prior to using this library of BD-Target clones, the BD-Target library may be preselected to filter out any self-activating clones. This selection may be accomplished by allowing the yeast clones that contain the BD-Target fusion to grow in a selection medium used for two-hybrid selection at a later stage, such as the medium SD/-Trp-His. The clones are checked for self-activation of the reporter gene in the absence of the AD domain.

Alternatively, the BD-Target library may be preselected in a selection medium with β- or α-galactosidase substrate. Any positive clones will produce a colored reaction catalyzed the galactosidase expressed from a LacZ reporter gene and can be easily detected by naked eyes or by an instrument. Such clones are self-activating clones that express the reporter gene in the absence of the AD domain. The clones may be excluded from the library of BD-Target clones.

Still referring to FIG. 9, the BD-target clones of a-strain of yeast may be inoculated into a plate which is pre-seeded with an arrayed library of scFv library of α-strain of yeast haploid cells. The two haploid yeast strains mate in the rich medium and form diploid. The parental clones are screened for expression of the reporter gene which indicates positive interactions between a scFV and a target protein expressed by the clones in the same well. The scoring of the positive clones may be conveniently carried out by machine-aided automatic screening using β- or α-galactosidase substrate. Aho, S. et al. (1997) "A novel reporter gene MEL1 for the yeast two-hybrid system" Anal. Biochem. 253:270–272.

Compared to the screening of a single target protein against a library of scFv proteins, the method illustrated in FIG. 9 is based on a clonal mating, i.e., individual target protein against individual scFv protein. The advantage of such clonal mating is that the efficiency of mating and selection may be enhanced through clonal mating when large numbers of target proteins and scFv antibodies are involved.

The methods described can be used for large scale screening of libraries of biomolecules, such as fully human antibody repertoires, against a wide variety target molecules or ligands. The screening process may be automated for high throughput screening of the biomolecules. For example, such screening process allows for efficient isolation and collection of scFv antibodies against any EST (human, mouse, or any other organisms), or any known structural/functional protein domains (Zinc finger, helix-loop-helix, etc.), or totally random peptides with various lengths.

In contrast, by using conventional methods for screening antibody in vivo, such as the hybridoma and "XENOMOUSE" technologies, such a large-scale and comprehensive antibody collection may have been impractical due to technical limitations associated with using animal as the host for the libraries of antibodies and target molecules.

By using the method of the present invention, the antibody repertoires can be screened for affinity interaction between an antibody in the library and a target antigen individually in vivo by clonal mating without losing track of individual clones. The screening should be more efficient than the procedure performed on mice, owing the to fast proliferation rate and ease of handling of yeast cells.

The method of the present invention should provide vary useful tools for profiling functions of genes, in particular, functional proteomics, efficiently and economically. With the completion of human genome sequencing, the demands are tremendous for efficient large-scale screening for functional proteins aimed at large numbers of target molecules. The high affinity and functional scFv antibodies, as well as other multimeric proteins, that are selected by using the methods of the present invention should find a wide variety applications in prevention, diagnosis, therapeutic treatment of diseases and in other biomedical or industrial uses.

6. Mutagenesis of the Fusion Protein Leads Positively Selected Against Target Protein(s)

As described above, protein leads, such as scFv antibody leads, can be identified through the selection of the primary library carrying V1 and V2 against one or more target proteins. The coding sequences of these protein leads may be mutagenized in vitro or in vivo to generated a secondary library more diverse than these leads. The mutagenized leads can be selected against the target protein(s) again in vivo following similar procedures described for the selection of the primary library carrying V1 and V2. Such mutagenesis and selection of primary antibody leads effectively mimics the affinity maturation process naturally occurring in a mammal that produces antibody with progressive increase in the affinity to the immunizing antigen.

The coding sequences of the fusion protein leads may be mutagenized by using a wide variety of methods. Examples of methods of mutagenesis include, but are not limited to site-directed mutagenesis, error-prone PCR mutagenesis, cassette mutagenesis, random PCR mutagenesis, DNA shuffling, and chain shuffling.

Site-directed mutagenesis or point mutagenesis may be used to gradually change the V1 and V2 sequences in specific regions. This is generally accomplished by using oligonucleotide-directed mutagenesis. For example, a short sequence of a scFv antibody lead may be replaced with a synthetically mutagenized oligonucleotide. The method may not be efficient for mutagenizing large numbers of V1 and V2 sequences, but may be used for fine toning of a particular lead to achieve higher affinity toward a specific target protein.

Cassette mutagenesis may also be used to mutagenize the V1 and V2 sequences in specific regions. In a typical cassette mutagenesis, a sequence block, or a region, of a single template is replaced by a completely or partially randomized sequence. However, the maximum information content that can be obtained may be statistically limited by the number of random sequences of the oligonucleotides. Similar to point mutagenesis, this method may also be used for fine toning of a particular lead to achieve higher affinity toward a specific target protein.

Error-prone PCR, or "poison" PCR, may be used to the V1 and V2 sequences by following protocols described in Caldwell and Joyce (1992) PCR Methods and Applications 2:28–33. Leung, D. W. et al. (1989) Technique 1:11–15. Shafikhani, S. et al. (1997) Biotechniques 23:304–306. Stemmer, W. P. et al. (1994) Proc. Natl. Acad. Sci. USA 91:10747–10751.

Figure 10:
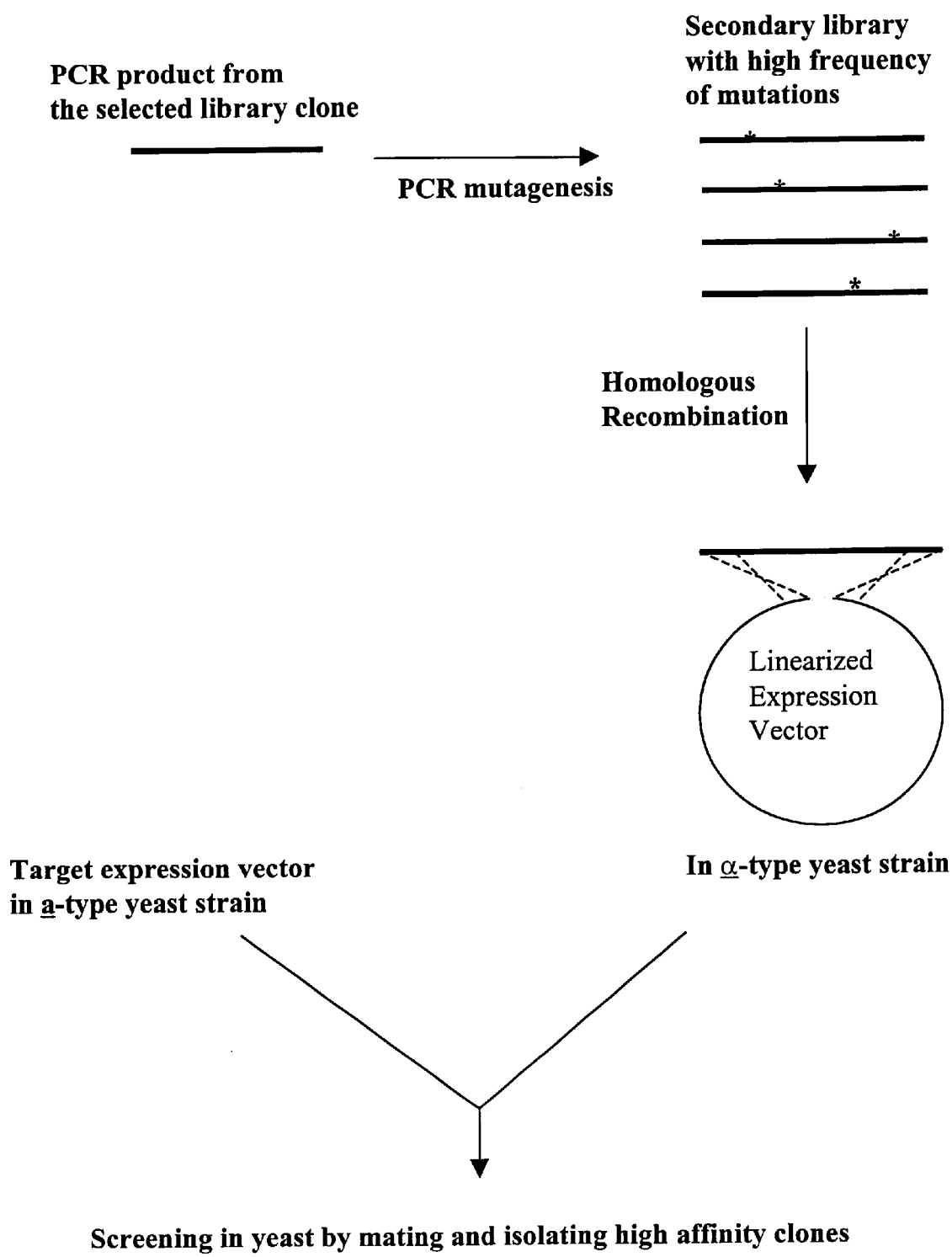
FIG. 10 illustrates an embodiment of a method used for mutagenesis and further screening of the clones selected from a primary screening of the tester proteins carried by the expression vector of the present invention.

FIG. 10 illustrates an example of the method of the present invention for affinity maturation of antibody leads selected from the primary scFv library. As illustrated in FIG. 10, the coding sequences of the scFv leads selected from clones containing the primary scFv library are mutagenized by using a poison PCR method. Since the coding sequences of the scFV library are contained in the expression vectors isolated from the selected clones, one or more pairs of PCR primers may be used to specifically amplify the $V_H$ and $V_L$ region out of the vector. The PCR fragments containing the $V_H$ and $V_L$ sequences are mutagenized by the poison PCR under conditions that favors incorporation of mutations into the product.

Such conditions for poison PCR may include a) high concentrations of $Mn^{2+}$ (e.g. 0.4–0.6 mM) that efficiently induces malfunction of Taq DNA polymerase; and b) disproportionally high concentration of one nucleotide substrate (e.g., dGTP) in the PCR reaction that causes incorrect incorporation of this high concentration substrate into the template and produce mutations. Additionally, other factors such as, the number of PCR cycles, the species of DNA polymerase used, and the length of the template, may affect the rate of mis-incorporation of "wrong" nucleotides into the PCR product. Commercially available kits may be utilized for the mutagenesis of the selected scFv library, such as the "Diversity PCR random mutagenesis kit" (catalog No. K1830-1, Clontech, Palo Alto, Calif.).

The PCR primer pairs used in mutagenesis PCR may preferably include regions matched with the homologous recombination sites in the expression vectors. This design allows re-introduction of the PCR products after mutagenesis back into the yeast host strain again via homologous recombination. This also allows the modified $V_H$ and $V_L$ region to be fused with the AD domain directly in the expression vector in the yeast.

Still referring to FIG. 10, the mutagenized scFv fragments are inserted into the expression vector containing an AD domain via homologous recombination in haploid cells of α type yeast strain. Similarly to the selection of scFv clones from the primary antibody library, the AD-scFv containing haploid cells are mated with haploid cells of opposite mating type (e.g. a type) that contains the BD-Target vector and the reporter gene construct. The parental diploid cells are selected based on expression of the reporter gene and other selection criteria as described in detail in Section 3.

Other PCR-based mutagenesis method can also be used, alone or in conjunction with the poison PCR described above. For example, the PCR amplified $V_H$ and $V_L$ segments may be digested with DNase to create nicks in the double DNA strand. These nicks can be expanded into gaps by other exonucleases such as Bal 31. The gaps may be then be filled by random sequences by using DNA Klenow polymerase at low concentration of regular substrates dGTP, dATP, dTTP, and dCTP with one substrate (e.g., dGTP) at a disproportionately high concentration. This fill-in reaction should produce high frequency mutations in the filled gap regions. These method of DNase I digestion may be used in conjunction with poison PCR to create highest frequency of mutations in the desired $V_H$ and $V_L$ segments.

The PCR amplified $V_H$ and $V_L$ segments or the scFv segments amplified from the primary antibody leads may be mutagenized in vitro by using DNA shuffling techniques described by Stemmer (1994) Nature 370:389–391; and Stemmer (1994) Proc. Natl. Acad. Sci. USA 91:10747–10751. The $V_H$, $V_L$ or scFV segments from the primary antibody leads are digested with DNase I into random fragments which are then reassembled to their original size by homologous recombination in vitro by using PCR methods. As a result, the diversity of the library of primary antibody leads are increased as the numbers of cycles of molecular evolution increase in vitro.

The $V_H$, $V_L$ or scFv segments amplified from the primary antibody leads may also be mutagenized in vivo by exploiting the inherent ability of mution in pre-B cells. The Ig gene in pre-B cells is specifically susceptible to a high-rate of mutation in the development of pre-B cells. The Ig promoter and enhancer facilitate such high rate mutations in a pre-B cell environment while the pre-B cells proliferate. Accordingly, $V_H$ and $V_L$ gene segments may be cloned into a mammalian expression vector that contains human Ig enhancer and promoter. This construct may be introduced into a pre-B cell line, such as 38B9, which allows the mutation of the $V_H$ and $V_L$ gene segments naturally in the pre-B cells. Liu, X., and Van Ness, B. (1999) Mol. Immunol. 36:461–469. The mutagenized $V_H$ and $V_L$ segments can be amplified from the cultured pre-B cell line and re-introduced back into the AD-containing yeast strain via, for example, homologous recombination.

The secondary antibody library produced by mutagenesis in vitro (e.g. PCR) or in vivo, i.e., by passing through a mammalian pre-B cell line may be cloned into an expression vector and screened against the same target protein as in the first round of screening using the primary antibody library. For example, the expression vectors containing the secondary antibody library may be transformed into haploid cells of α type yeast strain. These α cells are mated with haploid cells a type yeast strain containing the BD-target expression vector and the reporter gene construct. The positive interaction of scFvs from the secondary antibody library is screened by following similar procedures as described for the selection of the primary antibody leads in yeast.

Alternatively, since the secondary antibody library may be relatively low in complexity (e.g., $10^4$–$10^5$ independent clones) as compared to the primary libraries (e.g., $10^7$–$10^{14}$), the screening of the secondary antibody library may be performed without mating between two yeast strains. Instead, the linearized expression vectors containing the AD domain and the mutagenized $V_H$ and $V_L$ segments may be directly co-transformed into yeast cells containing the BD-target expression vector and the reporter gene construct. Via homologous recombination in yeast, the secondary antibody library are expressed by the recombined AD-scFv vector and screened against the target protein expressed by the BD-target vector by following similar procedures as described for the selection of the primary antibody leads in yeast.

7. Functional Expression and Purification of Selected Antibody

The library of fusion protens encoded by V1 and V2 that are generated and selected in the screening against the target protein(s) may be expressed in hosts after the V1 and V2 sequences are operably linked to an expression control DNA sequence, including naturally-associated or heterologous promoters, in an expression vector. By operably linking the V1 and V2 to an expression control sequence, the V1 and V2 coding sequences are positioned to ensure the transcription and translation of these inserted sequences. The expression vector may be replicable in the host organism as episomes or as an integral part of the host chromosomal DNA. The expression vector may also contain selection markers such as antibiotic resistance genes (e.g. neomycin and tetracycline resistance genes) to permit detection of those cells transformed with the expression vector.

Preferably, the expression vector may be a eukaryotic vector capable of transforming or transfecting eukaryotic host cells. Once the expression vector has been incorporated into the appropriate host cells, the host cells are maintained under conditions suitable for high level expression of the single-chains polypeptide encoded by V1 and V2, such as scFvs. The polypeptides expressed are collected and purified depending on the expression system used.

Figure 12:
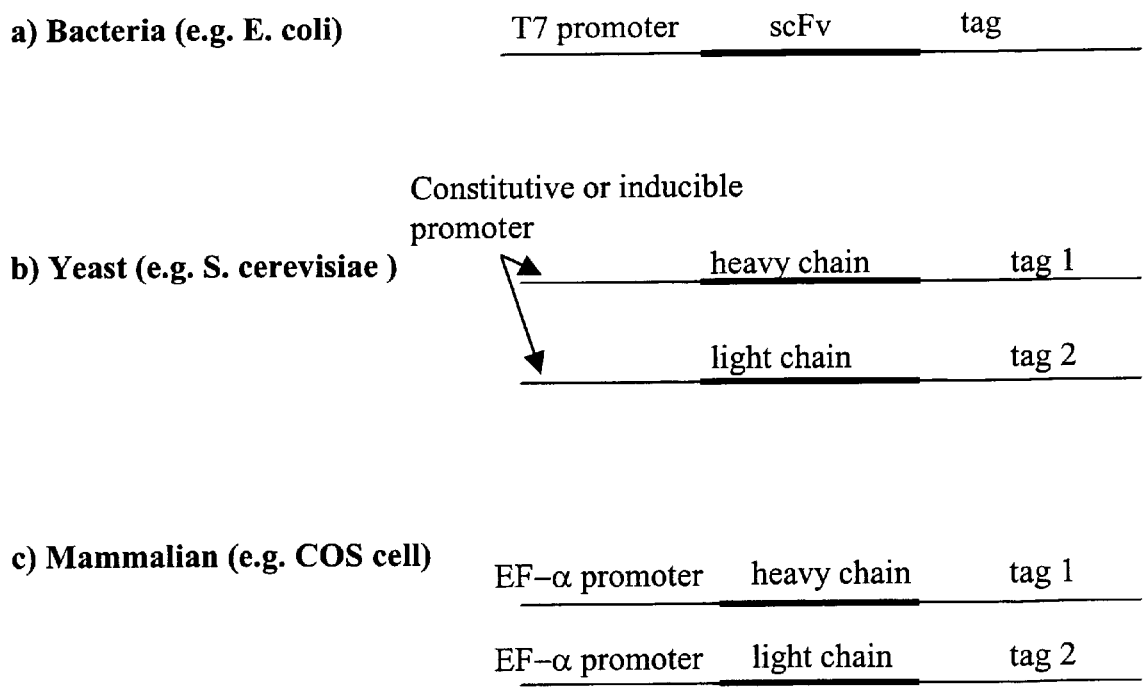
FIG. 12 illustrates examples of functional expression systems for antibody selected by using the method of the present invention.

The scFv, Fab, or fully assembled antibodies selected by using the methods of the present invention may be expressed in various scales in any host system. FIG. 12 illustrates examples of host systems: bacteria (e.g. *E. coli*), yeast (e.g. *S. cerevisiae*), and mammalian cells (COS). The bacteria expression vector may preferably contain the bacterial phage T7 promoter and express a single chain variable fragment (scFv). The yeast expression vector may contain a constitutive promoter (e.g. ADGI promoter) or an inducible promoter such as (e.g. GCN4 and Gal 1 promoters). All three types of antibody, scFv, Fab, and full antibody, may be expressed in a yeast expression system.

The expression vector may be a mammalian express vector that can be used to express the single-chains polypeptide encoded by V1 and V2 in mammalian cell culture transiently or stably. Examples of mammalian cell lines that may be suitable of secreting immunoglobulins include, but are not limited to, various COS cell lines, HeLa cells, myeloma cell lines, CHO cell lines, transformed B-cells and hybridomas.

Typically, a mammalian expression vector includes certain expression control sequences, such as an origin of replication, a promoter, an enhancer, as well as necessary processing signals, such as ribosome binding sites, RNA splice sites, polyadenylation sites, and transcriptional terminator sequences. Examples of promoters include, but are not limited to, insulin promoter, human cytomegalovirus (CMV) promoter and its early promoter, simian virus SV40 promoter, Rous sarcoma virus LTR promoter/enhancer, the chicken cytoplasmic β-actin promoter, promoters derived from immunoglobulin genes, bovine papilloma virus and adenovirus.

One or more enhancer sequence may be included in the expression vector to increase the transcription efficiency. Enhancers are cis-acting sequences of between 10 to 300 bp that increase transcription by a promoter. Enhancers can effectively increase transcription when positioned either 5' or 3' to the transcription unit. They may also be effective if located within an intron or within the coding sequence itself. Examples of enhancers include, but are not limited to, SV40 enhancers, cytomegalovirus enhancers, polyoma enhancers, the mouse immunoglobulin heavy chain enhancer. and adenovirus enhancers. The mammalian expression vector may also typically include a selectable marker gene. Examples of suitable markers include, but are not limited to, the dihydrofolate reductase gene (DHFR), the thymidine kinase gene (TK), or prokaryotic genes conferring antibiotic resistance. The DHFR and TK genes prefer the use of mutant cell lines that lack the ability to grow without the addition of thymidine to the growth medium. Transformed cells can then be identified by their ability to grow on non-supplemented media. Examples of prokaryotic drug resistance genes useful as markers include genes conferring resistance to G418, mycophenolic acid and hygromycin.

The expression vectors containing the V1 and V2 sequences can then be transferred into the host cell by methods known in the art, depending on the type of host cells. Examples of transfection techniques include, but are not limited to, calcium phosphate transfection, calcium chloride transfection, lipofection, electroporation, and microinjection.

The V1 and V2 sequences may also be inserted into a viral vector such as adenoviral vector that can replicate in its host cell and produce the polypeptide encoded by V1 and V2 in large amounts.

In particular, as illustrated in FIG. 12, the scFv, Fab, or fully assembled antibody may be expressed in mammalian cells by using a method described by Persic et al. (1997) Gene, 187:9–18. The mammalian expression vector that is described by Persic and contains EF-α promoter and SV40 replication origin is preferably utilized. The SV40 origin allows a high level of transient expression in cells containing large T antigen such as COS cell line. The expression vector may also include secretion signal and different antibiotic markers (e.g. neo and hygro) for integration selection.

Once expressed, polypeptides encoded by V1 and V2 may be isolated and purified by using standard procedures of the art, including ammonium sulfate precipitation, fraction column chromatography, and gel electrophoresis. Once purified, partially or to homogeneity as desired, the polypeptides may then be used therapeutically or in developing, performing assay procedures, immunofluorescent stainings, and in other biomedical and industrial applications. In particular, the antibodies generated by the method of the present invention may be used for diagnosis and therapy for the treatment of various diseases such as cancer, autoimmune diseases, or viral infections.

In a preferred embodiment, the scFv human antibody with $V_H$ and $V_L$ segments that are generated and screened by using the methods of the present invention may be expressed directly in yeast. According to this embodiment, the $V_H$ and $V_L$ regions from the selected expression vectors may be PCR amplified with primers that simultaneously add appropriate homologous recombination sequences to the PCR products. These PCR segments of $V_H$ and $V_L$ may then be introduced into a yeast strain together with a linearized expression vector containing desirable promoters, expression tags and other transcriptional or translational signals.

For example, the PCR segments of $V_H$ and $V_L$ regions may be homologously recombined with a yeast expression vector that already contains a desirable promoter in the upstream and stop codons and transcription termination signal in the downstream. The promoter may be a constitutive expression promoter such as ADH1, or an inducible expression promoter, such as Gal 1, or GCN4 (A. Mimran, I. Marbach, and D. Engelberg, (2000) Biotechniques 28:552–560). The latter inducible promoter may be preferred because the induction can be easily achieved by adding 3-AT into the medium.

The yeast expression vector to be used for expression of the scFv antibody may be of any standard strain with nutritional selection markers, such as His 3, Ade 2, Leu 2, Ura 3, Trp 1 and Lys 2. The marker used for the expression of the selected scFv may preferably be different from the AD vector used in the selection of scFv in the two-hybrid system. This may help to avoid potential carryover problem associated with multiple yeast expression vectors.

For expressing the scFv antibody in a secreted form in yeast, the expression vector may include a secretion signal in the 5' end of the $V_H$ and $V_L$ segments, such as an alpha factor signal and a 5-pho secretion signal. Certain commercially available vectors that contain a desirable secretion signal may also be used (e.g., pYEX-S1, catalog #6200-1, Clontech, Palo Alto, Calif.).

The scFv antibody fragments generated may be analyzed and characterized for their affinity and specificity by using methods known in the art, such as ELISA, western, and immune staining. Those scFv antibody fragments with reasonably good affinity (with dissociation constant preferably above $10^{-6}$ M ) and specificity can be used as building blocks in Fab expression vectors, or can be further assembled with the constant region for full length antibody expression. These fully assembled human antibodies may also be expressed in yeast in a secreted form.

Figure 11:
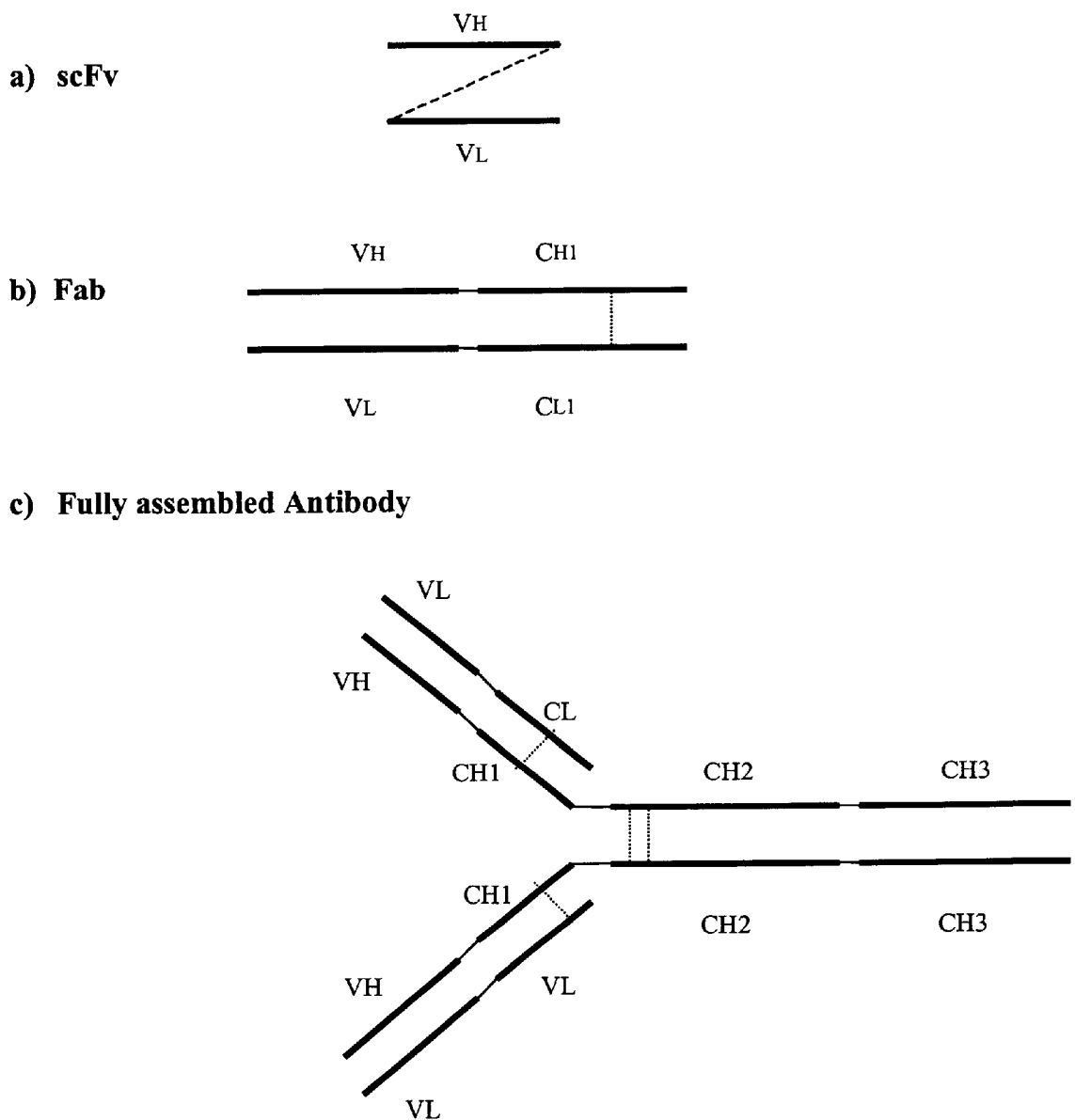
FIG. 11 illustrates secondary structures of single-chain variable fragments (scFv), antibody fragments (Fab), and a fully-assembled antibody.

FIG. 11 illustrates the secondary structures of the scFv, Fab and a fully assembled antibody. The $V_H$ sequence encoding the selected scFv protein may be linked with the constant regions of a full antibody, CH1, CH2 and CH3. Similarly, the VL sequence may be linked with the constant region CL. The assembly of two units of VH-CH1-CH2-CH3 and VL-CL leads to formation of a fully functional antibody. The present invention provides a method for producing fully functional antibody in yeast. Fully functional antibody retaining the rest of the constant regions may have a higher affinity (or avidity) than a scFv or a Fab. The full antibody should also have a higher stability, thus allowing more efficient purification of antibody protein in large scale.

The method is provided by exploiting the ability of yeast cells to uptake and maintain multiple copies of plasmids of the same replication origin. According to the method, different vectors may be used to express the heavy chain and light chain separately, and yet allows for the assembly of a fully functional antibody in yeast. This approach has been successfully used in a two-hybrid system design where the BD and AD vectors are identical in backbone structure except the selection markers are distinct. This approach has been used in a two-hybrid system design for expressing both BD and AD fusion proteins in the yeast. The BD and AD vectors are identical in their backbone structures except the selection markers are distinct. Both vectors can be maintained in yeast in high copy numbers. Chien, C. T., et al. (1991) "The two-hybrid system: a method to identify and clone genes for proteins that interact with a protein of interest" Proc. Natl. Acad. Sci. USA 88:9578–9582.

In the present invention, the heavy chain gene and light chain genes are placed in two different vectors. Under a suitable condition, the VH-CH1-CH2-CH3 and VL-CL sequences are expressed and assembled in yeast, resulting in a fully functional antibody protein with two heavy chains and two light chains. This fully functional antibody may be secreted into the medium and purified directly from the supernatant.

The scFv with a constant region, Fab, or fully assembled antibody can be purified using methods known in the art. Conventional techniques include, but are not limited to, precipitation with ammnonium sulfate and/or caprylic acid, ion exchange chromatography (e.g. DEAE), and gel filtration chromatography. Delves (1997) "Antibody Production: Essential Techniques", New York, John Wiley & Sons, pages 90–113. Affinity-based approaches using affinity matrix based on Protein A, Protein G or Protein L may be more efficiency and results in antibody with high purity. Protein A and protein G are bacterial cell wall proteins that bind specifically and tightly to a domain of the Fc portion of certain immunoglobulins with differential binding affinity to different subclasses of IgG. For example, Protein G has higher affinities for mouse IgG1 and human IgG3 than does Protein A. The affinity of Protein A of IgG1 can be enhanced by a number of different methods, including the use of binding buffers with increased pH or salt concentration. Protein L binds antibodies predominantly through kappa light chain interactions without interfering with the antigen-binding site. Chateau et al. (1993) "On the interaction between Protein L and immunoglobulins of various mammalian species" Scandinavian J. Immunol., 37:399–405. Protein L has been shown to bind strongly to human kappa light chain subclasses I, III and IV and to mouse kappa chain subclasses I. Protein L can be used to purify relevant kappa chain-bearing antibodies of all classes (IgG, IgM, IgA, IgD, and IgE) from a wide variety of species, including human, mouse, rat, and rabbit. Protein L can also be used for the affinity purification of scFv and Fab antibody fragments containing suitable kappa light chains. Protein L-based reagents is commercially available from Actigen, Inc., Cambridgem, England. Actigen can provide a line of recombinant Protein products, including agarose conjugates for affinity purification and immobilized forms of recombinant Protein L and A fusion protein which contains four protein A antibody-binding domains and four protein L kappa-binding domains.

Other affinity matrix may also be used, including those that exploit peptidomimetic ligands, anti-immunoglobulins, mannan binding protein, and the relevant antigen. Peptidomimetic ligands resemble peptides but they do not correspond to natural peptides. Many of Peptidomimetic ligands contain unnatural or chemically modified amino acids. For example, peptidomimetic ligands designed for the affinity purification of antibodies of the IGA and IgE classes are commercially available from Tecnogen, Piana di Monte Verna, Italy. Mannan binding protein (MBP) is a mannose- and N-acetylglucosamine-specific lectin found in mammalian sera. This lectin binds IgM. The MBP-agarose support for the purification IgM is commercially available from Pierce.

Immunomagnetic methods that combine an affinity reagent (e.g. protein A or an anti-immunoglobulin) with the ease of separation conferred by paramagnetic beads may be used for purifying the antibody produced. Magnetic beads coated with Protein or relevant secondary antibody may be commercially available from Dynal, Inc., NY; Bangs Laboratories, Fishers, Ind.; and Cortex Biochem Inc., San Leandro, Calif.

Direct expression and purification of the selected antibody in yeast is advantageous in various aspects. As a eukaryotic organism, yeast is more of an ideal system for expressing human proteins than bacteria or other lower organisms. It is more likely that yeast will make the scFv, Fab, or fully assembled antibody in a correct conformation (folded correctly), and will add post-translation modifications such as correct disulfide bond(s) and glycosylations.

Yeast has been explored for expressing many human proteins in the past. Many human proteins have been successfully produced from the yeast, such as human serum albumin (Kang, H. A. et al. (2000) Appl. Microbiol. Biotechnol. 53:578–582) and human telomerase protein and RNA complex (Bachand, F., et al. (2000) RNA 6:778–784).

Yeast has fully characterized secretion pathways. The genetics and biochemistry of many if not all genes that regulate the pathways have been identified. Knowledge of these pathways should aid in the design of expression vectors and procedures for isolation and purification of antibody expressed in the yeast.

Moreover, yeast has very few secreted proteases. This should keep the secreted recombinant protein quite stable. In addition, since yeast does not secrete many other and/or toxic proteins, the supernatant should be relatively uncontaminated. Therefore, purification of recombinant protein from yeast supernatant should be simple, efficient and economical.

Additionally, simple and reliable methods have been developed for isolating proteins from yeast cells. Cid, V. J. et al. (1998) "A mutation in the Rho&GAP-encoding gene BEM2 of *Saccharomyces cerevisiae* affects morphogenesis and cell wall functionality" Microbiol. 144:25–36. Although yeast has a relatively thick cell wall that is not present in either bacterial or mammalian cells, the yeast cells can still keep the yeast strain growing with the yeast cell wall striped from the cells. By growing the yeast strain in yeast cells without the cell wall, secretion and purification of recombinant human antibody may be made more feasible and efficient.

By using yeast as host system for expression, a streamlined process can be established to produce recombinant antibodies in fully assembled and purified form. This may save tremendous time and efforts as compared to using any other systems such as humanization of antibody in vitro and production of fully human antibody in transgenic animals.

In summary, the compositions, kits and methods provided by the present invention should be very useful for selecting proteins such as human antibodies with high affinity and specificity against a wide variety of targets including, but not limited to, soluble proteins (e.g. growth factors, cytokines and chemokines), membrane-bound proteins (e.g. cell surface receptors), and viral antigens. The whole process of library construction, functional screening and expression of highly diverse repertoire of human antibodies can be streamlined, and efficiently and economically performed in yeast in a high throughput and automated manner. The selected proteins can have a wide variety of applications. For example, they can be used in therapeutics and diagnosis of diseases including, but not limited to, autoimmune diseases, cancer, transplant rejection, infectious diseases and inflammation.

EXAMPLE

Example 1

Construction of Expression Vectors Containing Human Single-Chain Antibody scFv Library Using Homologous Recombination in Vivo The following illustrates examples of how to use general homologous recombination as an efficient way of constructing recombinant human scFv library. The coding sequence of each member of the scFV library includes a heavy-chain variable region $V_H$ and a light-chain variable region $V_L$ derived from a library of human antibody repertoire. The scFv library is fused with a two-hybrid system activation domain (AD) to form a two-hybrid expression vector in the yeast.

1) Isolation of Human scFv cDNA Gene Pool

A complex human scFv cDNA gene pool is generated by using the method described in Sambrook, J., et al. (1989) Molecular Cloning: a laboratory manual. Cold Spring Harbor Laboratory, Cold Spring Harbor, N.Y.; and Ausubel, F. M. et al. (1995) Current Protocols in Molecular Biology" John Wiley & Sons, NY.

Briefly, total RNA is isolated from the white cells (mainly B cells) contained in peripheral blood supplied by un-immunized humans. Blood sample at 500 ml, which contains approximately $10^8$ B-lymphocytes, are obtained from healthy donors from Stanford Hospital Blood Center. The white blood cells are separated on Ficoll and RNA is isolated by a modified method. Sambrook, J., et al. (1989), supra; and Zhu, L. et al. (1997) "Yeast Gal 4 activation domain fusion expression libraries" in "The Yeast Two-Hybrid System", S. Fields and P. Bartel, Ed., Oxford University Press, pages 73–98.

If starting from tissue, RNA is first isolated using standard procedures. Ramirez, F. et al. (1975) "Changes in globin messenger rNA content during erythroid cell differentiation" J. Biol. Chem. 250:6054–6058; and Sambrook, J., et al. (1989), supra. First strand cDNA synthesis is performed using the method of Marks et al. in which a set of heavy and light chain cDNA primers are designed to anneal to the constant regions for priming the synthesis of cDNA of heavy chain and light chains (both kappa and lambda) antibody genes in separate tubes. Marks et al. (1991) Eur. J. Immunol. 21:985–991.

Alternatively, human spleen or leukocyte cDNA can be purchased directly from commercial source, such as Clontech, Palo Alto, Calif.

2) PCR Amplification of Heavy and Light Chain Genes

The coding sequences of human heavy and light chain genes are amplified from the cDNA library generated above by using a method described by Sblattero and Bradbury (1998) Immunotechnology 3:271–278. This method allows almost 100% coverage of all human $V_H$, Vλ and Vκ genes from the known Ig gene database. Specifically, cDNA pool from human spleen is used (human spleen Marathon-Ready cDNA, Cat.#7412-1, Clontech, Palo Alto, Calif.). Alternatively, cDNA pool from human leukocytes can also be used (human leukocyte Marathon-Ready cDNA, Cat.#7406-1. Clontech, Palo Alto, Calif.).

The $V_H$, Vλ and Vκ genes are amplified separately by PCR using a set of mixed 5' and 3' primers for each class. The 5' and 3' primers for $V_H$, Vλ and Vκ genes also contain flanking sequences at both ends homologous to a cloning library vector, pACT2 (catalog No. K1604-A, Clontech, Palo Alto, Calif.; Harper et al (1993) "The p21 Cdk-interacting protein Cip1 is a protein inhibitor of G1 cyclin-dependent kinase" Cell 75:805–816). Each flanking sequence added to the primary PCR product is 60 bp in length. The design of the flanking sequence of primer is such that the reading frame of the $V_H$ and $V_L$ fragments are conserved with upstream GAL 4 reading frame that is encoded by the cloning vector. Depending on the cloning vector used in the next step, additional features such as epitope tags (for detection and purification) and unique restriction enzyme recognition sites (for subcloning) can also be integrated at this step by primer design.

The amplified $V_H$, Vλ and Vκ genes are cloned sequentially into the pACT2 cloning vector in yeast via homologous recombination following the schemed depicted in FIG. 2.

Table 2 lists the primer sets used in combination in this method of sequential homologous recombination. Each of the $V_H$5'-primers (back primers), VH1b–VH7b, contains a 60-bp flanking sequence (underlined) homologous to the upstream of the MCS site of pACT2. Each of the $V_H$3'-primers (forward primers), VH1f–VH6f, contains a 60-bp flanking sequence encoding a linker peptide sequence $(G_4S)_4$ (underlined) [SEQ ID NO: 75]. The $V_H$5'-primers and the $V_H$3'-primers are used in combination to amplify the heavy-chain regions of the human antibody gene pool from the cDNA library. The resulting PCR fragments can be used for subsequent insertion into the pACT2 vector via the first-step homologous recombination.

Each of the Vλ (or Vκ) 5'-primers (back primers), Vλ1b–Vλ9b (or Vκ1b–Vκ4b) contains the 60-bp flanking sequence encoding a linker peptide sequence $(G_4S)_4$ (underlined). Each of the Vλ (or Vκ) 3'-primers (forward primers), Vλ1f and Vλ2f (or Vκ1f–Vκ4f), contains a 60-bp flanking sequence (underlined) homologous to the downstream of the MCS site of pACT2. The Vλ (or Vκ) 5'-primers and the Vλ or Vκ 3'-primers are used in combination to amplify the light-chain regions of the human antibody gene pool from the cDNA library. The resulting PCR fragments can be used for subsequent insertion into the pACT2 vector via second-step homologous recombination.

The PCR reaction is done in the volume of 50 ul containing 5 ul of the cDNA synthesized from step 2, 20 pmol concentration of the mixed 5' and 3' primers, 250 uM dNTPs, 10 mM KCl, 10 mM $(NH4)_2SO_4$, 20 mM Tris.HCl (pH 8.8), 2.0 mM $MgCl_2$, 100 mg/ml BSA, and 1 ul (1 unit) of KlenTaq DNA polymerase (New England Biolabs, Massachusetts). The reaction mixture is subjected to 30 cycles of amplification using a Perkin-Elmer thermal cycler. The cycle is 94° C. for 1 min (denaturation), 57° C. for 1 min (annealing), and 72° C. for 2.5 min (extension). Vλ and Vκ chain PCR products are pooled together at this stage. The PCR products are checked by electrophoresis and purified from 1.0% agarose gel using Qiax affinity matrix (Qiagen, California) and resuspended in 25 ul of $H_2O$.

3) Alternative Design: PCR Assembly of $V_H$ and $V_L$ into a Single Fragment $V_H$ and $V_L$ (Vλ and Vκ) gene fragments isolated and amplified above can be assembled into a single fragment by the overlapping PCR priming method. This is a step utilizing the linker region sequence added to the 3' end of $V_H$ and 5' of $V_L$ fragments. A typical linker region is a tandem repeat of 4 amino acids $(G_4S)_{3-4}$, and the linker used in this example is $(G_4S)_4$ [SEQ ID NO: 75]. Each single $V_H$ or $V_L$ PCR product is about 420–480 bp, whereas the combined $V_H$ and $V_L$ fragment, is about 800–850 bp. The $V_H$ and $V_L$ (Vλ and Vκ) gene fragments amplified and isolated as described above are assembled in PCR reactions via the homologous linker sequences shared between the 3'-primers of the $V_H$ gene and the 5'-primers of the $V_L$ gene (Vλ and Vκ). The result PCR fragment combining $V_H$ and $V_L$ linked by the $(G_4S)_4$ linker L is referred as VH-L-VL. Conditions used for the PCR assembly is same the PCR for amplifying the $V_H$ and $V_L$ genes separately as described above, except that the cycle number is 20.

The PCR assembled product containing both $V_H$ and $V_L$ gene fragments are analyzed by agarose electrophoresis, and are purified from agarose gel by Qiax method (Qiagen, California).

4) Cloning of Heavy- and Light-chain Fv Fragments into a Two-hybrid AD Vector by Homlogous Recombination in Yeast The PCR fragments of $V_H$ and $V_L$ cDNA gene pool generated above are cloned into a two-hybrid vector containing an activation domain (AD) by homologous recombination in one step by using the combined single fragments VH-L-VL generated above.

The two-hybrid vector containing an AD domain, pACT2 is purchased from Clontech, Palo Alto, Calif. In this example, 10 μg of pACT2 is linearized with restriction enzymes digestion in the multiple cloning sites (MCS). This is done in 20 ul volume containing the following reagents: 10 μg of vector DNA, 1–2 ul of each restriction enzyme BamH I and Xho I, 2 ul of 10×buffer. Digestion is carried out at 37° C. overnight. The completion of the enzyme digestion is checked by electrophoresis. No further modification or purification of linearized vector is necessary.

The linearized vector DNA (10 μg) is mixed with equal amount of the PCR amplified VH-L-VL fragments (about 5–10 molar excess of the insert fragment) in a single fragment as described in section 3). The linearized vector DNA and the PCR fragment are co-transformed into competent yeast strain Y187 (α mating type, from Clontech).

Transformation is performed as the following. Yeast competent cells are prepared by LiAc protocol (Gietz et al. (1992) "Improved method for high efficiency transformation of intact yeast cells" Nucleic Acids Res. 20:1425), or obtained from a commercial source (Life Technology Inc., Maryland). Minimum yeast competency of $10^6$ transformant/ug DNA may be required for library construction. Yeast competent cells derived from 1 liter culture of OD600=0.2 are used for each transformation in 50 ml conical bottom tubes. Yeast cells are thawed at 4° C., washed with de-ionized water and resuspended in 8 ml of 1×TE/LiAc (1×TE/LiAc is made up of 40% polyethylene glycol 4000, 10 mM Tris-HCl, 1 mM EDTA, pH 7.5, and 0.1 M lithium acetate). The mixture of DNA containing the linearized vector and PCR amplified inserts with extended ends is added to the tube and vortexed to mix. The tube is incubated at 30° C. for 30 min, with shaking (200 rpm). DMSO (Dimethyl sulfoxide, 700 ul) is added into the tube and mixed gently. The cells in the tube are heat shocked at 42° C. in a water bath for 15 minutes with occasional swirl. After the heat shock, the cells are pelleted by a brief centrifugation at 4° C. and washed one or two time with water. The cells are resuspended in 1.5 ml of 1×TBE buffer.

Yeast cells are plated into plates made up of selection medium. For Y187 strain of yeast, the SD/-Leu medium is used. Harper et al. (1993), supra. The library scale transformation requires approximately 100 large plates of 150 mm in diameter. Y187 transformed with either linearized vector without insert DNA fragment or vise versa is also plated onto the same selection plates as controls. Y187 transformed with unlinearized vector pACT2 is used as transformation efficiency control and is plated with series dilutions. The plates are incubated bottom up at 30° C. for 3 days or more. Colony number is examined and recorded. If the yeast control transformation with unlinearized pACT2 yields at least 1 million transformants, as expected, 10 millions of single chain library recombinant clones are expected to obtain from each such transformation. Any control transformation with either the linearized vector or insert DNA fragment alone is expected to yield only ¹/₁₀ or less number of colonies as compared with the combined vector/insert transformation. This single step of transformation is repeated until 100 million or more independent clones are obtained.

For the separate PCR fragments of $V_H$ and $V_L$ as described in section 2), the $V_H$ and $V_L$ fragments are inserted into a modified pACT2 cloning vector separately following the scheme depicted in FIG. 2. This is achieved by sequential transformations consisting of two independent events of homologous recombination in vivo.

Figure 13:
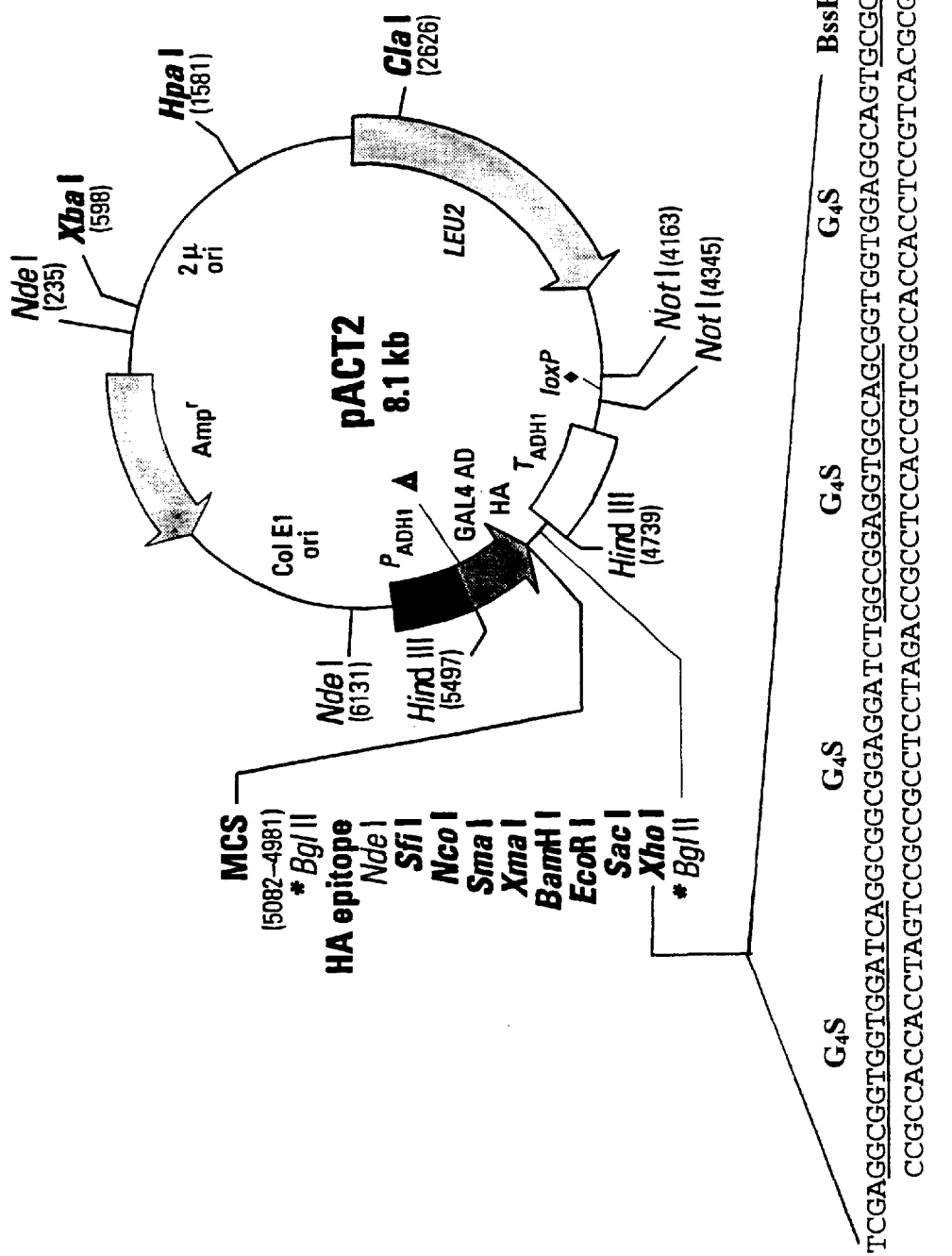
FIG. 13 illustrates the plasmid map of pACT2 and a method of modifying pACT2 in order to introduce a $(G_4S)_4$ linker into the plasmid.

The original pACT2 plasmid is modified by oligonucleotide-directed mutation. FIG. 13 illustrated the plasimid map of pACT2 and the method of modification. As illustrated in FIG. 13, an oligonucleotide containing the linker sequence encoding the linker peptide $(G_4S)_4$ and a few unique restriction sites (e.g. BssH I and Pac I) is inserted downstream from the stop codon of the AD domain in pACT2. Table 3 lists sense [SEQ ID NO: 46] and antisense strands [SEQ ID NO: 47] of the oligonucleotides used to modify pACT2.

The sense and antisense strands listed in Table 3 are annealed and phosphorylated by T4 DNA kinase (New England Biolabs, Massachusetts). The annealed double-stranded DNA fragment contains these features in this order: a cohesive end of Xho I (functional after ligation), the $(G_4S)_4$ linker sequence, BssH 2 site, Pac I site, and another cohesive end of Xho I (not functional after ligation). As illustrated in FIG. 13, the annealed fragment are then ligated to a Xho I-digested pACT2 which has been dephosphorylated by calf intestinal alkaline phosphatase. After the orientation of the inserted fragment in the new vector (designated pACT2-GS) is confirmed, the two-step homologous recombination is performed.

The modified yeast cloning vector, pACT2-GS, is digested with BamH I and Xho I. The $V_H$ and $V_L$ inserts in separate PCR fragments as described in section 2), are incorporated sequentially into the linearized pACT2-GS vector in Y187 yeast cells via homologous recombination.

The PCR fragments of $V_H$ are inserted into the BamH I and Xho I-linearized pACT2-GS vector downstream of the AD domain, but upstream of the $(G_4S)_4$ linker sequence via homologous recombination. This transformation is preferred to yield at least 1 million independent clones.

After this first round of homologous recombination, the yeast cells are pooled and the plasmid DNA with the $V_H$ insert is recovered and transformed into bacterial cells for plasmid preparation. Competent E. coli strain KC8, either chemical or electrical competent (available from Clontech, Palo Alto, Calif., Cat #C2004-1 or #C2023-1, respectively) is used for a convenient amino acid complementation as selection for pACT2 with its leucine marker. The plasmid are prepared from KC8 cells in large scales for a second round yeast transformation by an independent homologous recombination.

The pACT2 vector having the $V_H$ insert is linearized by Pac I, downstream from the $(G_4S)_4$ linker sequence. The resulting Pac I-linearized vector (10 µg) and the PCR-fragments of VL are transformed into Y187 yeast cells where the VL fragments are inserted into the vector via a second homologous recombination. The transformants are plated again in SD/-Leu selection plates. Such single transformation is preferred to yield 100 million or more independent clones. These clones are double homologous recombined library clones with both human $V_H$ and $V_L$ chains.

The yeast library recombinant colonies generated as described above are scraped from the final culture plates after growing for 5–7 days. The majority of the yeasts are mixed with 50% (volume) of glycerol and stored at −80° C. for future library screening use. A small fraction of the yeast clones are subjected to the following quality analyses:

a. Percentage of Recombinant Clones:

PCR amplification of the insert (either the VH-L-VL insert in a single PCR fragment, or $V_H$ and $V_L$ in separate PCR fragments, depending on the procedure used in 2) OR 3) above) directly from yeast with a primer pair matched with flanking vector sequences (e.g., Long PCR primer pair for AD vectors supplied by Clontech) should reveal how many clones are recombinant. Since our design of extended homologous regions for recombination between the insert and cloning vector is sufficient long (about 60 bp), a high percentage of recombinant clone (higher than 95%) should be expected. Libraries with minimum of 90% recombinant clones are preferably to be saved for screening use.

b. Insert Size:

The same PCR amplification of selected clones should reveal the insert size. Although a small fraction of the library may contain double or other forms of multiple inserts, the majority (>95%) should have single insert with expected size.

c. Fingerprinting Verification of Sequence Diversity:

PCR amplification product with the correct size is fingerprinted with frequent digesting restriction enzymes, such as Bst NI or any other 3–4 base cutters. From the agarose gel electrophoresis pattern, one can determine whether clones analyzed are of the same identity or of the distinct or diversified identity. The PCR products can also be sequenced directly. This will reveal the identity of inserts and the fidelity of the cloning procedure, and will prove the independence and diversity of the clones. If 100 clones are sequenced, it should be expected that only small fraction (<5%) of clones will have multiple isolates.

Example 2

Construction of Human scFv Library by Using CRE/loxP-mediated Recombination in Vivo In this example, the construction of a highly complex and diverse combinatorial repertoire in yeast using V-region gene segments as building blocks is described.

First, a special type of human scFv library is generated in yeast by the standard homologous recombination procedure underlined in Example 1. This library is consisting of $10^7$ or more of highly diverse and complex V-region gene repertoire derived from heavy chain and light chain origin. One pool (e.g., VL or light chain gene segment) is flanked on both sides by two non-identical lox P sites. The loxP sites are designed into the primer sequences used in one of the PCR amplification steps. Examples of the loxP sites are listed in Table 1.

Specifically, two nonidentical loxP sites, loxP1 [SEQ ID NO: 4] and loxP2 [SEQ ID NO: 5] (Table 1), are incorporated into the PCR primers for amplifying the $V_H$ and $V_L$ gene segments from the cDNA library as described in Example 1, Section 2).

Table 4 lists the primer sets used in combination for amplifying the $V_H$ and $V_L$ gene segments from the cDNA library. Each of the $V_H5'$-primers (back primers), VH1b–VH7b, contains a 60-bp flanking sequence (underlined) homologous to the upstream of the MCS site of pACT2. These primers are the same as those used for amplifying $V_H$ gene segments without incorporating the loxP sites.

Each of the $V_H3'$-primers (forward primers), VH1'f–VH6'f, contains a 63-bp flanking sequence (underlined). The $V_H5'$-primers and the $V_H3'$-primers are used in combination to amplify the heavy-chain regions of the human antibody gene pool from the cDNA library. (Note: The resulting PCR fragments can be used for subsequent insertion into the pACT2 vector via the first-step homologous recombinatiQo as illustrated in FIG. 2.)

Each of the Vλ (or Vκ) 5'-primers (back primers), Vλ1'b–Vλ9'b (or Vκ1'b–Vκ4'b), contains a 63-bp flanking sequence that is complementary to the 63-bp flanking sequence of the $V_H3'$-primers and comprises these sequences in 5' to 3' order: a $(G_4S)$ coding sequence a loxP1 site, and a $G_3S$ coding sequence (underlined).

Each of the Vλ (or Vκ) 3'-primers (forward primers), Vλ1'f and Vλ2'f (or Vκ1'f–Vκ4'f), contains a 30-bp flanking sequence (underlined) that is a partial loxP2 site. The Vλ (or Vκ) 5'-primers and the Vλ or Vκ 3'-primers are used in combination to amplify the light-chain regions of the human antibody gene pool from the cDNA library. The resulting PCR fragments are further amplified by using a new 3' primer (listed as the Vλ/Vκf primer in Table 4) in a secondary PCR to incorporate the full loxP M2 site and a sequence homologous to the downstream of the MCS site of pACT2. This design allows amplification of the VL gene segments by using shorter primers. (Note: The amplified VL segments can be used for subsequent insertion into the pACT2 vector via the second-step homologous recombination as illustrated in FIG. 2).

The PCR reaction is done in the volume of 50 ul containing 5 ul of the cDNA synthesized from step 2, 20 pmol concentration of the mixed 5' and 3' primers, 250 uM dNTPs, 10 mM KCl, 10 mM $(NH4)_2SO_4$, 20 mM Tris.HCl (pH 8.8), 2.0 mM MgCl2, 100 mg/ml BSA, and 1 ul (1 unit) of KlenTaq DNA polymerase (New England Biolabs, Massachusetts). The reaction mixture is subjected to 30 cycles of amplification using a Perkin-Elmer thermal cycler. The cycle is 94° C. for 1 min (denaturation), 57° C. for 1 min (annealing), and 72° C. for 2.5 min (extension). Vλ and Vκ chain PCR products are pooled together at this stage. The PCR products are checked by electrophoresis and purified from 1.0% agarose gel using Qiax affinity matrix (Qiagen, Calif.) and resuspended in 25 ul of $H_2O$.

$V_H$ and $V_L$ (Vλ and Vκ) gene fragments isolated and amplified above are assembled into a single fragment by the overlapping PCR priming method as illustrated in FIG. 3. This is a step utilizing the linker sequence added to the 3' end of $V_H$ and 5' of $V_L$ fragments. In this case, the linker sequence contains a $(G_4S)$ coding sequence, a loxP1 site, and a $G_3S$ coding sequence.

Each single $V_H$ or $V_L$ PCR product is about about 420–480 bp, whereas the combined $V_H$ and $V_L$ fragment is about 800–850 bp. The $V_H$ and $V_L$ (Vλ and Vκ) gene fragments amplified and isolated as described above are assembled in PCR reactions via the homologous linker sequences shared between the 3'-primers of the $V_H$ gene and the 5'-primers of the $V_L$ gene (Vλ and Vκ). The resulting PCR fragment combining $V_H$ and $V_L$, wherein VL is flanked by loxP1 and loxP2 sites, is referred as VH-loxP1-VL-loxP2. Conditions used for the PCR assembly is the same PCR for amplifying the $V_H$ and $V_L$ genes separately as described above, except that the cycle number is 20.

The PCR assembled product containing both $V_H$ and $V_L$ gene fragments (the VH-loxP1-VL-loxP2 fragments) are analyzed by agarose electrophoresis, and are purified from agarose gel by Qiax method (Qiagen, Calif.).

The VH-loxP1-VL-loxP2 fragments are inserted into the pACT2 vector via homologous recombination in vivo following the general scheme depicted in FIG. 3. The procedure is the same as the one used for homologous recombination between pACT2 and the VH-L-VL fragments described in section Example 1, Section 4).

After a library is generated and $10^7$ of independent clones are accumulated, this entire library of pACT2 plasmids containing the VH-loxP1-VL-loxP2 sequences is isolated from pooled yeast clones and then transformed into E. coli strain KC8 through the shared leucine nutritional marker complementation. Bacterial strain KC8 carries hisB, leuB, and trpC mutations. These mutations exhibit amino acids deficiency and can be complemented by the corresponding genes from yeasts. See Yeast Protocol Handbook, Clontech, PT3024-1, page 33.

Isolation of the plasmid pool from the yeast cells is done using the lyticase protocol. Guthrie and Fink (1991) "Guide to yeast genetics and molecular biology" in Methods in Enzymology (Academic Press, San Diego) 194:1–932. Briefly, the library clones grown in selection plates are scraped out and resuspended in 1×TE. A freshly made 5 units/ul lyticase (Sigma, St. Luis, Miss.) solution is added to the yeast suspension at 1:5 v:v ratio and the mixture is incubated at 37 C for 60 min with occasional swirling. Using dissect microscope to check the degree of yeast wall digestion. If the yeast wall is completely digested, yeast cells will burst immediately in water or low salt solution. When the digestion is completed, add 20% of SDS at 1:5 v:v ratio and continue to incubate for a few minutes. The yeast suspension is subject to several freeze-thaw cycles by placing the tube in dried ice and water bath (37° C.). At this stage, the suspension is passed through a DNA fractionation column, e.g., CHROMA Spin 1000 from Clontech, Palo Alto, Calif. The column cleans up the cell debris and other components, only letting plasmid DNA to pass through. The plasmid DNA can be collected by washing the column with 1×TE.

This collection of yeast plasmid DNA is then used for transformation into E. coli stain KC8 (Chemical or electrical competent KC8 cells can be ordered from Clontech, Cat #C2004-1 or #C2023-1). In either case, when the bacterial cell is transformed with the plasmid pool isolated from yeast, selection plates made of M9 minimum medium is used for plating the bacteria. Because the shared nutritional selection marker, leucine deficiency, is present in both the yeast strain and the bacterial strain, the plasmid which carries the dominant marker, can be rescued from the bacteria. Finally, the KC8 cells are let to grow and a large-scale DNA isolation from KC8 is done for DNA pools which are subsequently mixed.

This pooled DNA source is then re-introduced into yeast host strain Y187 using conventional single plasmid transformation protocol. The condition of this transformation is set to enrich for multiple plasmid entry into every single yeast cells. Yeast can take multiple plasmids as demonstrated by the two-hybrid system design where both AD and BD plasmids are co-existing in the same yeast host cells. A normal small-scale yeast transformation with 1 ug level of DNA will give rise to an average of yeast transformants with 30–50 copies of plasmid.

The multiple plasmid entry into yeast is maximized by using higher DNA-yeast ratio in the transformation step. The yeast cells are also pre-transformed with a plasmid that inducibly expresses CRE recombinase. The inducible expression of CRE in the yeast strain causes the CRE-mediated site-specific recombination at the Lox P sites that flank each light chain gene fragment. Therefore, while yeast is allowed to grow and the plasmids in the yeast cells are making additional copies, shuffling of the light chain gene segment VL (Vλ and Vκ) should occur inside of yeast cells. This process of CRE/loxP-mediated chain shuffling is illustrated in FIG. 4A.

Assuming this shuffling is totally random and complete with the entire pool, the total number of combination of heavy chain and light chain within the yeast cells will be increased exponentially. Thus, a library with at least $10^9$ of recombinant clones can be generated. Theoretically, the complexity of the library can reach $10^{14}$ if the starting library has a complexity of $10^7$.

This recombination in yeast should not require any marker selection. The CRE/loxP recombination should occur irrespective of with selection or without selection. The key to success in this example is multiple entry of plasmid into the yeast cells which is a norm in the yeast transformation. This mode of multiple plasmid entry is tested by using different color GFP variant plasmids. For example, plasmids harboring GFP (encodes green fluorescent protein) or YFP (a mutant form of GFP that encodes yellow fluorescent protein) are mixed at 1:1 ratio and used for yeast transformation. These plasmids should have no difference in their structures in terms of selection marker or plasmid composition except for the expression cassette (either GFP or YFP). The coding regions of these two fluorescent proteins are of the same length and only differ from each other in very few amino acids (S65 G, V68A, S72A and T203Y) Miller D. M., (1999) Biotechniques 26:914–918. These plasmids resemble the library of expression vectors that carry the human antibody coding variable regions in that all antibody molecules are essentially of the same length and differ from each other only in a small number of amino acid compositions, most in the hypo-variable regions. If yeast takes multiple fluorescent protein plasmids, certain fraction of yeast transformed should show a combined color spectrum. Some colonies will show a mosaic phenotype. This test also allows for optimization of the condition for multiple plasmid transformation.

Example 3

Construction of Human scFv Library of Very High Complexity by Using CRE/loxP-Mediated Recombination in Vivo-Second Design An alternative method to the method described in Example 2 for construction of human scFv library using CRE/loxP-mediated recombination is to use a "forced" multiple transformation. In this design, two starting human scFv libraries containing human heavy and light chain gene segments are generated separately in two vectors with different selection markers (e.g., Leu 2 and Ade 2, respectively). By selection of both markers will ensure that every yeast cell have both types of library clones (each may have multiple but variable number of copies). The activation or expression of Cre combinase in the yeast should allow the CRE/loxP-mediated recombination as illustrated in FIG. 4B.

Two special human scFv libraries are generated in yeast via homologous recombination by using the procedures described in Example 2. The two libraries are otherwise the same in terms of their source RNA, amplification, and the cloning procedures. The only difference is the cloning vector used. One library contains the human scFv library carried by an unmodified pACT2 with Leu 2 as a yeast selection marker, while the other contains the human scFv library carried by a modified pACT2 with Ade 2 as a yeast selection marker. Each library includes $10^7$ or more of highly diverse and complex V-region gene repertoire derived from heavy chain and light chain origins of human antibody. The VH-loxP1-VL-loxP2 PCR fragments generated in Example 2 are inserted into the linearized pACT2 vector with Leu 2 and the linearized pACT2 vector with Ade 2 respectively, via homologous recombination in yeast. The results in two library of scFv carried by two different pACT2 vectors with different selection markers.

After $10^7$ of independent clones are accumulated in each of these two libraries, this entire library DNA is isolated from pooled yeast library clones and then transformed into bacterial strain KC8 through bacteria-yeast leucine nutritional marker complementation. The procedures are similar to those described in Example 2. Large-scale DNA isolations from KC8 are done from the two libraries and the two DNA pools are kept separately. These two pooled DNA sources are co-transformed into yeast Y187 cells at 1:1 ratio by using conventional single plasmid transformation protocols.

Y187 has the following genotype: Matα, ura3-52, his3-200, ade2-101, trp1-901, leu2-3, 112, gal4Δ, met, gal80Δ, URA3::GAL1$_{UAS}$-GAL1$_{TATA}$-lacZ. Harper, et al. (1993) Cell 75:805–816. It allows both types of plasmids to be selected and maintained by Leucine and Adenine complementation. The condition of this transformation is similar to the standard plasmid transformation and can be modified to reach a maximum efficiency of transformation.

The transformants are plated onto SD/-Leu/-Ade medium for selecting both types of library plasmids. Any yeast colonies formed on this double selection medium must have transformed by both types of library clones. Each type of the library clone is in multiple copies, usually at 30–50 copies per cell. Except for a few particular individual cells, the pairing of the two library clones should be totally random.

Similar to the yeast cells in Example 2, the yeast cell is also pretransformed with a plasmid that inducibly expresses CRE recombinase. The inducible expression of CRE recombinase in the yeast strain causes the Cre-mediated homologous recombination at loxP sites flanking each light chain gene fragment.

Therefore, while yeast is allowed to grow and the plasmids in the yeast cells are making additional copies, shuffling of the light chain gene segment VL should occur inside of yeast cells. This process of CRE/loxP-mediated site specific recombination is illustrated in FIG. 4B. Assuming this shuffling is totally random and is complete with the entire pool, the total number of combination of heavy chain and light chain within the yeast cells will be increased exponentially. We can thus generate a library with at least $10^9$ of recombinant clones. Theoretically, the complexity of the library can reach $10^{14}$ if the starting two libraries each has a complexity of $10^7$.

Example 4

Screening of Antibody Single Chain Fv Libraries in Yeast with the Two-hybrid System Against Defined Protein Antigens via Mating Between Two Yeast Strains This example describes a procedure used to screen the antibody scFv libraries generated in the Examples 1, 2 and/or 3. The scFv libraries containing human $V_H$ and $V_L$ segments are generated in yeast strain with an α mating type. This mating type of yeast can be readily mated with an a type of yeast with simple mating procedure to form diploid yeast cells. Guthrie and Fink (1991) "Guide to yeast genetics and molecular biology" in Methods in Enzymology (Academic Press, San Diego) 194:1–932. The a-yeast contains the target (probe, or bait) plasmid.

The target plasmid contains a fusion formed between the GAL 4 DNA binding domain (BD) and any desired target protein that is to be used as a probe to fish out the antibodies as its affinity ligand. When the two types of yeast cell mate and form diploid cells, the probe plasmid and the library clone plasmid also come together in a same cell. Therefore, if a specific antibody scFv clone recognizes and binds to the probe protein, each of these proteins or protein fragments should bring their fusion partners (GAL 4 AD and GAL 4 BD) to a close proximity in the promoter region of reporter (s). Under such a circumstance, the reporter(s) construct built in the yeast cells (the parental a- and/or α-type of haploid cells) should be activated by the active GAL 4 proteins. Thus the reporter is expressed and a positive signal in the library screen is detected. Certain reporter(s) are of nutritional reporter, which allows the yeast to grow on a specific selection medium plate.

In practice, equal volume of bait-containing yeast strain (a-type) and scFv library-containing yeast stain (α-type) are inoculated into selection liquid medium and incubated with rigorous shaking at 30° C. for 20 hours. These cultures are then mixed in a single flask and allowed to grow in rich medium 1×YPD (20 g/l Difco peptone, 10 g/l yeast extract, and 2% glucose) for 12–16 additional hours with slow shaking at 30° C. Under the rich nutritional culture condition, the two haploid yeast strains encounter and mate to form diploid cells. At the end of this mating process, a good fraction—5–10% of the yeast population present in the mating pool will form diploids. Bendixen, C., Gangloff, S., and Rothstein, R. (1994) "A yeast mating-selection scheme for detection of protein-protein interactions" Nucleic Acids Res. 22:1778–1779.

After mating, the yeast cells are washed with $H_2O$ several times and plated into selection plates by using the SD/-Leu-Trp-His-Ade selections. The first two selections are for selection markers (Leu and Trp) expressed from the vectors and are for retaining both BD and AD vectors in the same yeast cells. The selected cells should be diploid cells, since either haploid cell only expresses one of these markers. The latter two markers are expressed by the reporter from the host strains and are for selection of clones that show positive interaction between the members of the scFv library and the target protein.

Example 5

Screening of Single Chain Fv Antibody Libraries Against a Library of Antigens in a Yeast Two-hybrid System For small number of pre-selected probes, the procedure of individual mating screening as described above is sufficient. However, this procedure can also be modified to suit for screening against large number of targets or probes. The following list describes the potential probes that are in large number and may not suitable for individual mating screening:

a. A collection of human EST clones, or total library of human EST. Such EST collection can be ordered from public resource in a library format with individually clones arrayed in 96-well or 384-well plates. The EST inserts from the original collection (usually in bacterial cloning and sequencing vectors) are PCR amplified with extended homologous sequences at both ends. The EST inserts can be PCR amplified and additional flanking sequences can be added to both ends of the ESTs by PCR for mediating homologous recombination in yeast. Then through the same homologous recombination procedure describe in Examples 1 and 2, the EST insert can be cloned into the AD vector. A maximum of three homologous recombination events should be sufficient for the read-through fusion of each EST with the GAL4 AD. Hua, S. B. et al. (1997) "Minimum length of sequence homology required for in vitro cloning by homologous recombination in yeast" Plasmid 38:91–96.

b. A collection of certain domain structures, such as zinc finger protein domains each having 18–20 amino acids. These domain structures may not be completely random. Synthetic oligonucleotides with characteristic conserved and random/degenerate residues can be made to cover most of the rational domain structures;

c. A completely random peptide library each having 16–20 amino acid residues. Such a library can also be made by random oligonucleotide synthesis. Such library has been constructed in an AD vector. Yang, M. et al. "(1995) "Protein-protein interactions analyzed with the yeast two-hybrid system" Nucleic Acids Res. 23:1152–1157. Such a library of probes can also be built in an BD vector. Each clone of such library represents a short peptide. The scFv antibody library (built in AD vector) is screened against this library of probes, peptide ligands for each scFv antibody can be selected. Such peptides may have potential applications in rational design and structural improvement of antigens.

The library of probes are cloned into a DB vector and each is fused with GAL4 DB domain. This library are made as an arrayed clone library by depositing every clone obtained with BD-probe fusion into a well in 96 or 384 well plates. This arrayed format facilitates large scale library screening with machine-aided automation.

Prior to using the library of probes to screen against the scFv library, the library of probes are transformed into yeast a-type of host strain to select out any self-activating clones. This pre-selection is to allow the yeast harboring only the probe plasmids to grow in a selection medium (SD/-Trp-His) and check for activation without the AD mating partner, the so-called self activation.

Alternatively, the pre-selection is conducted in selection medium with α- or β-galactosidase substrate. Any positive clones will produce a colored reaction and can be easily detected by naked eye or by instrument. The clone that send out positive signals indicating activation of the reporter gene(s) are self-activating clones which are excluded from the subsequent use as the targets for the scFv library.

The machine-aided automatic screening is performed by using 96- or 384-well plates. The target clones of a-strain are sequentially inoculated into a plate which is pre-seeded with an arrayed library of the scFv library of α-strain. The two haploid yeast strains mate in the rich medium and form diploid. The wells sending positive signals of reporter gene expression are detected. The screening process is similar to the individual target screening against a library in the mixed culture as described in Example 3. The difference in this case is that clonal mating (a mating between an individual target against an individual scFv) is performed here to enhance the efficiency when large numbers of targets and scFv antibodies are involved.

Example 6

Maturation of scFv Primary Isolates by Random Mutagenesis in vitro and Re-screening in vivo in a Yeast Two-hybrid System The scFv clones isolated from in Examples 1–3 can be of various degree of affinity. Although high affinity clones may be obtained with a low marginal possibility, the majority of the clones may need further modification to reach affinity compatible with natural antibodies (dissociation constant at $10^{-9}$ M or lower).

In this example, the sequences of primary scFv clones are mutagenized in vitro to incorporate random mutations into the $V_H$ and $V_L$ regions, thereby creating a secondary library of scFv with increased complexity. Complexity of the secondary library is expected to be at $10^4$ or higher. So the combined diversity of primary and secondary libraries screened should be at $10^{14}$–$10^{18}$, no less than the natural antibody diversification through selection/maturation in an animal.

Coding sequences of the $V_H$ and $V_L$ regions of the selected scFv are amplified from the corresponding scFV clones by PCR. The $V_H$ and $V_L$ region is resided in the AD vector and is fused with GAL4 AD domain. A pair of PCR primers are used to specifically amplify the $V_H$ and $V_L$ region out of the vector. The pair of primers are designed to match with the regions of the cloning vectors that flank the V-regions genes. These regions contains sequences for homologous recombination between the cloning vector and the amplified product. The PCR product is predicted to be about 0.8 kB.

This primary PCR product is checked by agarose gel electrophoresis for correct size and amount. An aliquot of the primary PCR product is then subjected to a secondary PCR. This secondary PCR is designed to incorporate mutations into the product under these conditions: high concentration of $Mn^{2+}$ and over-proportionaly high concentration of one nucleotide substrate in the PCR reaction in the PCR reaction. $Mn^{2+}$ at a concentration of between 0.4 and 0.6 mM can efficiently cause Taq polymerase to incorporate mutations into the PCR product. This mis-incorporation is caused by the malfunction of Taq DNA polymerase. Single nucleotide (e.g., dGTP) at an extra higher concentration than the other 3 essential nucleotides (dATP, dTTP, and dCTP) causes the incorrect incorporation of this high concentration substrate into the template and produce mutations.

Besides the two conditions listed above, other condition may influence the rate of mis-incorporation of "wrong" nucleotide into the PCR product, including the number of PCR cycles, the species of DNA polymerase used, and the length of the template. In this example, a pre-made kit is used (Diversity PCR Random Mutagenesis Kit, Cat.#K1830-1, Clontech, Palo Alto, Calif.). This kit contains reagents necessary for optimizing the conditions for random mutation by PCR, such as dNTP Mix and additional dGTP solution, Manganese Sulfate, and control PCR template and primer mix.

As suggested by the user manual for this kit, the following condition is used for PCR mutagenesis: 640 uM $MnSO_4$, 200 uM dGTP. Under this condition, an average of 8 mutations is expected to be found in every 1000 bp, a rate that is sufficient for scFv diversification.

This secondary scFv library is reintroduced into yeast through homologous recombination and screened directly in yeast following similar procedures as in the primary screening described in Example 3. This whole process mimics the naturally occurring affinity maturation process that higher organisms including human are inherited.

Example 7

Expression and Purification of Fully Assembled Human Antibodies in Yeast

Through the process of primary screening, affinity maturation, and secondary screening as described in Examples 1–6, specific scFv human antibody with high affinity toward a given target antigen are selected. The selected antibody can be expressed directly in yeast.

Using the yeast as expression host has several advantages. First, as a eukaryotic organism, yeast is more of an ideal system for expressing human proteins than bacteria or other lower organisms. It is more likely that yeast will make the scFv, Fab, or fully assembled antibody in a correct configuration and conformation (with correct protein folding), and will add post-translation modifications such as disulfide bond(s) and glycosylations. Second, yeast has been explored for expressing many human proteins in the past. Many human proteins have been successfully produced from the yeast. Third, yeast has fully characterized secretion pathways. The genetics and biochemistry of many if not all genes that regulate the pathways have been identified. Fourth, yeast has very few secreted proteases. This makes the secreted recombinant protein quite stable. In addition, yeast does not secrete many other proteins, or toxic substance such as PLS. So the supernatant is relatively uncontaminated. Therefore, purification of recombinant protein from yeast supernatant is simple and desirable.

By using yeast as host system for expression, a streamlined process can be established to produce recombinant antibodies in fully assembled and purified form. This should save time and efforts as compared to using other systems involving animals.

The $V_H$ and $V_L$ regions of the selected scFv are amplified from the corresponding clones with primers that simultaneously adding sufficient homologous recombination sequences to the PCR product. These PCR products are then be introduced into a yeast strain together with a linearized expression vector. Through homologous recombination, a new circle vector are generated which includes the $V_H$ and $V_L$ regions linked to the desired promoter upstream and stop codons and transcription termination signal downstream. A secretion signal is also added in the 5' end of the $V_H$ and $V_L$ segments, so the recombinant protein can be expressed as secreted form.

A few commercially available vectors offer the secretion signal. In this example, the PCR fragments of scFv sequences can be cloned into this type of vector for simple final purification. The expression vector includes either a constitutive expression promoter such as ADH1 (Ruohonen, Aalto, and Keranen (1995) "Modification of the ADH1 promoter of *Saccharomyces cerevisiae* for efficient production of heterologous proteins" Journal of Biotechnology 39:193–203), or an inducible expression promoter, such as Gal 1 (Flick and Johnston (1990) "Two systems of glucose repression of the GAL1 promoter in *Saccharomyces cerevisiae*" Mol. Cell Biol. 10:4757–4769), or GCN4 (Mimran, et al. (2000) Biotechniques, 28:552–560). The GCN4 inducible promoter is preferred because the induction can be easily achieved by adding 3-AT into the yeast culture medium. The scFv antibody fragments thus generated will be useful for assessment of affinity and specificity in traditional settings, such as ELISA, western, or immune staining. If they are of good affinity and specificity, they can be used either as building blocks in Fab expression vectors, or can be further assembled with the constant region for full length antibody expression (see below).

The yeast strain to be used for expression can be of any standard strain with a nutritional selection marker. The marker used for expression in this example is different from that of the AD vector. This will help to avoid potential carryover problem.

Moreover, fully assembled human antibodies can also be expressed in yeast in secreted form by taking advantage of the fact that yeast can take and maintain multiple copies of plasmid of the same replication origin. This has been successfully used in the two-hybrid system design where the BD and AD vectors are identical in backbone structure except the selection markers are distinct. So in this example, the heavy chain gene and light chain gene are co-expressed by two different vectors. Thus, a fully functional antibody protein with two heavy chains and two light chains can be assembled in the yeast and secreted into the medium. This step not only confers upon the final product higher affinity (or avidity) and stability but also renders the purification of the secreted product much easier. The same approach can be used for assembling the Fab fragments in the yeast.

The scFv with a constant region, Fab, or fully assembled antibody can be purified using Protein A, Protein L, or Protein G as affinity matrix. These proteins of bacterial origin are naturally occurring high affinity ligands for most classes of Antibody. They are commercially available and have been used widely in small and large-scale antibody purification.

Described below in detail is an example for expression of a secreted scFv fragment in yeast. This approach can be easily adapted for expression of Fab or full-length antibody (e.g., Ig G).

The plasmid pGES426 (Mimran, Marbach, and Engelberg (2000) Biotechniques, 28:552–560) is used as a yeast expression vector. This vector contains a backbone derived from pBluescript, $2\mu$ yeast replication origin for high copy plasmid maintenance, and full length GCN4 upstream regulatory sequence (1067 pb) that offers the highest efficiency of expression of heterologous gene. The experiment results using human serum albumin as testing gene showed that this full-length upstream sequence is required for the highest level of 3-AT induction. A yeast secretion signal sequence such as signal sequence of Suc 2 which encodes invertase gene, Kaizer, C. A. and Botstein, D. 1986, Mol Cell Biol. 6:2382–2391) is cloned into this vector upstream from the unique BamH I insert cloning site. The sequence of Suc 2 [SEQ ID NO: 74] is ATGCTTTTGC AAGCTTTCCT TTTCCTTTTG GCTGGTTTTG CAGCCAAAAT ATCTG-CATCA ATG.

The BamH I site is purposely reserved only in the 3' end of the secretion signal sequence. A scFv fragment that is obtained through yeast two-hybrid screening and with desired specificity against a given antigen probe, is PCR amplified from the original two-hybrid AD-scFv fusion library vector. The PCR primer is designed to amplify the scFv region sequence and contains an additional translation initiation codon ATG at the 5' end, and a translation stop codon TAA at the 3' end. In addition, a BamH I site is also incorporated into each of the PCR primers. After PCR amplification using a high-fidelity DNA polymerase (e.g. KlenTaq, Barnes, W. M. (1994) "PCR amplification of up to 35-kb DNA with high fidelity and high yield from λ bacteriophage templates" Proc. Natl. Acad. Sci. USA 91:2216–2220), the amplified fragment is digested with BamH I. This fragment is further treated with kinase to add phosphoryl group to the 5' ends.

Meanwhile, the vector is also digested with BamH I and dephosphorylated with a phosphotase. After that, the scFv fragment is ligated with the linearized expression vector, and a recombinant clone with correct orientation is isolated. This recombinant clone is then introduced into yeast host strain BJ2168 (from the yeast genetics stock center at the University of California, Berkeley). This yeast strain has the following genotype: MATa, prc1-407, prb1-1122, pep4-3, leu2, trp1, ura3-52. Since this strain carries multiple mutant type genes of protease (prc, prb, etc), it is a desired host strain for heterologous protein expression (Zubenko, Michell, and Jones, 1980 Genetics 96:137–146).

Yeast BJ2168 containing recombinant the plasmids is allowed to grow at 30° C. with rigorous shaking in the selection medium (SD/-URA) to a log phase. The inducing agent, 3-AT (3-amino-1,2,4-triazole, Sigma #A-8056), is added to the medium to reach a concentration of 40 mM and the culture is allowed to grow for additional 6–10 hours. After that, the culture medium containing the secreted protein is collected by centrifugation to remove medium. Protein purification and enrichment is carried out essentially according to the standard procedure described in Rose and Broach (1990) "Propagation and expression of cloned genes in yeast: 2-$\mu$m circle-based vectors" Math. Enzymol. 185:234–279. Expression of scFv is monitored by standard electrophoresis with Cormassie blue staining or by western blot using a tag antibody (tagging sequence such as c-Myc can be included in the PCR primer and integrated into the expression vector in the PCR amplification step).

Once the condition of expression for scFv is optimized using the multi-copy plasmid vector, further optimization is done using an integration vector pGES306. This vector differs from pGES426 only in one aspect: it does not have the $2\mu$ origin of replication. So it has to be integrated into the yeast genome for stable maintenance. Experiments showed that the level of heterologous gene expression by GCN4 promoter does not rely on plasmid copy number. Mimran, Marbach, and Engelberg (2000) Biotechniques 28:552–560. Therefore, an integrated version of GCN4 vector (present in single copy in the yeast) gives an equivalent level of protein expression as compared with the $2\mu$ version plasmid (present in multiple copies usually 30–50 copies in the yeast). The integrated vector offers an advantage: it allows the yeast to grow in the nutrient medium such as YPD. So yeast can grow to very high density and the protein expression yield can be increased significantly under such culture condition. The secreted scFv is isolated and purified using methods known in the art.

---

What is claimed is:

1. A method for selecting tester proteins capable of binding to a target peptide or protein, the method comprising:

expressing a library of tester fusion proteins in yeast cells, each tester fusion protein comprising either an activation domain or a DNA binding domain of a transcription activator and a tester protein having a diversity of at least $1 \times 10^7$ within the library, the tester protein comprising a first polypeptide subunit whose sequence varies within the library, a second polypeptide subunit whose sequence varies within the library independently of the first polypeptide, and a linker peptide which links the first and second polypeptide subunits;

expressing a target fusion protein in the yeast cells expressing the tester fusion proteins, the target fusion protein comprising either the DNA binding domain or the activation domain of the transcription activator which is not comprised in the tester fusion proteins, and a target peptide or protein; and selecting those yeast cells in which a reporter gene is expressed, the expression of the reporter gene being activated by a reconstituted transcriptional activator formed by binding of the tester fusion protein to the target fusion protein.

2. The method of claim 1, wherein expressing the library of tester fusion proteins includes transforming a library of tester expression vectors into the yeast cells which contain a reporter construct comprising the reporter gene whose expression is under transcriptional control of the reconstituted transcription activator, each tester expression vector comprising a first transcription sequence encoding either the activation domain or the DNA binding domain of the transcription activator, and a sequence encoding one of the tester proteins.

3. The method of claim 2, wherein expressing a target fusion protein includes
  transforming a target expression vector into the yeast cells simultaneously or sequentially with the library of tester expression vectors, the target expression vector comprising
    a second transcription sequence encoding either the activation domain or the DNA binding domain of the transcription activator which is not expressed by the library of tester expression vectors; and
    a target sequence encoding the target protein or peptide; and
  expressing the target fusion protein from the target expression vector.

4. The method of claim 1, wherein the steps of expressing the library of tester fusion proteins and expressing the target fusion protein include causing mating between first and second populations of haploid yeast cells of opposite mating types,
  wherein
  the first population of haploid yeast cells comprises
    a library of tester expression vectors for the library of tester fusion proteins, each tester expression vector comprising
      a first transcription sequence encoding either the activation domain or the DNA binding domain of the transcription activator, and
      a sequence encoding one of the tester proteins;
  the second population of haploid yeast cells com prises a target expression vector comprising
    a second transcription sequence encoding either the activation domain or the DNA binding domain of the transcription activator which is not expressed by the library of tester expression vectors, and
    a target sequence encoding the target protein or peptide; and
  either the first or second population of haploid yeast cells comprises a reporter construct comprising the reporter gene whose expression is under transcriptional control of the transcription activator.

5. The method of claim 4, wherein the haploid yeast cells of opposite mating types are α and a type strains of yeast.

6. The method of claim 5, wherein the mating between the first and second populations of haploid yeast cells of α and a type strains is in a rich nutritional culture medium.

7. The method of claim 1, wherein the diversity of tester proteins in the library of tester fusion proteins is at least $1 \times 10^8$.

8. The method of claim 1, wherein the diversity of tester proteins in the library of tester fusion proteins is at least $1 \times 10^{10}$.

9. The method of claim 1, wherein the diversity of tester proteins in the library of tester fusion proteins is at least $1 \times 10^{12}$.

10. The method of claim 1, wherein the first polypeptide subunit in the library of tester proteins comprises an antibody heavy-chain variable region, and the second polypeptide subunit comprises an antibody light-chain variable region.

11. A method for selecting tester proteins capable of binding to a target peptide or protein, comprising:
  (a) transforming a library of tester expression vectors into yeast cells which contain a reporter construct comprising a reporter gene whose expression is under transcriptional control of a transcription activator comprising an activation domain and a DNA binding domain, each tester expression vector comprising
    a first transcription sequence encoding either the activation domain or the DNA binding domain of the transcription activator, and
    a tester protein sequence comprising first nucleotide sequence encoding a first polypeptide subunit, a second nucleotide sequence encoding a second polypeptide subunit, and a linker sequence encoding a linker peptide that links the first and the second polypeptide subunits;
  (b) transforming a target expression vector into the yeast cells simultaneously or sequentially with the library of tester expression vectors, the target expression vector comprising
    a second transcription sequence encoding either the activation domain or the DNA binding domain of the transcription activator which is not expressed by the library of tester expression vectors; and
    a target sequence encoding the target protein or peptide;
  (c) expressing the tester fusion proteins from the library of tester expression vectors and the target fusion protein from the target expression vector;
  (d) selecting those yeast clones in which the reporter gene is expressed, the expression of the reporter gene being activated by binding of the tester fusion protein to the target fusion protein;
  (e) isolating the tester expression vector from the selected yeast clones; and
  (f) mutagenizing the first and second nucleotide sequences in the isolated tester expression vectors to form a library of mutagenized expression vectors.

12. The method of claim 11, wherein the mutagenesis is selected from the group consisting of error-prone PCR mutagenesis, site-directed mutagenesis, DNA shuffling and combinations thereof.

13. The method of claim 1, wherein the target fusion protein comprises an antigen associated with a disease state.

14. The method of claim 1, wherein the target fusion protein comprises a tumor-surface antigen.

15. A method for selecting single chain antibodies capable of binding to a human growth factor receptor, comprising:
  (a) transforming a library of tester expression vectors into yeast cells which contain a reporter construct comprising the reporter gene whose expression is under transcriptional control of a transcription activator comprising an activation domain and a DNA binding domain, each tester expression vector comprising
    a first transcription sequence encoding either the activation domain or the DNA binding domain of the transcription activator, and
    a tester protein sequence comprising first nucleotide sequence encoding an antibody heavy chain variable region, a second nucleotide sequence encoding an antibody light chain variable region, and a linker sequence encoding a linker peptide that links the antibody heavy chain and light chain variable regions;
  (b) transforming a target expression vector into the yeast cells simultaneously or sequentially with the library of tester expression vectors, the target expression vector comprising
    a second transcription sequence encoding either the activation domain or the DNA binding domain of the transcription activator which is not expressed by the library of tester expression vectors, and
    a target sequence encoding a human growth factor receptor;

(c) expressing the tester fusion proteins from the library of tester expression vectors and the target fusion protein from the target expression vector; and (d) selecting those yeast clones in which the reporter gene is expressed, the expression of the reporter gene being activated by binding of the tester fusion protein to the target fusion protein.

16. The method of claim 15, wherein the human growth factor is selected from the group consisting of epidermal growth factors, transferrin, insulin-like growth factor, transforming growth factors, interleukin-1, and interleukin-2.

17. The method of claim 1, wherein the protein encoded by the reporter gene is selected from the group consisting of β-galactosidase, α-galactosidase, luciferase, β-glucuronidase, chloramphenicol acetyl transferase, secreted embryonic alkaline phosphatase, green fluorescent protein, enhanced blue fluorescent protein, enhanced yellow fluorescent protein, and enhanced cyan fluorescent protein.

18. The method of claim 1, wherein the first polypeptide subunit and the second polypeptide subunit are encoded by variable regions of immunoglobulin genes of a human, non-human primates, or rodent.

19. The method of claim 1, wherein the first polypeptide subunit and the second polypeptide subunit are encoded respectively by a heavy-chain variable region and a light-chain variable region of a human immunoglobulin gene.

20. The method of claim 1, wherein the first polypeptide subunit is encoded by a heavy-chain variable region of a first human immunoglobulin gene, and the second polypeptide subunit is encoded by a light chain variable region of a second human immunoglobulin gene different from the first human immunoglobulin gene.

21. The method of claim 13, wherein the first and second polynucleotides encode an antibody heavy chain variable region and an antibody light chain variable region, respectively.

22. A method for selecting tester proteins capable of binding to a target peptide or protein and improving their binding affinity, comprising:

(a) causing mating between a first and a second population of haploid yeast cells of opposite mating types, wherein
   the first population of haploid yeast cells comprises
      a library of tester expression vectors for a library of tester fusion proteins having a diversity of at least $1 \times 10^7$, each tester expression vector comprising
         a first transcription sequence encoding either the activation domain or the DNA binding domain of a transcription activator, and
         a tester protein sequence comprising a first nucleotide sequence encoding a first polypeptide subunit, a second nucleotide sequence encoding a second polypeptide subunit, and a linker sequence encoding a linker peptide that links the first and the second polypeptide subunits;
   the second population of haploid yeast cells comprises
      a target expression vector comprising
         a second transcription sequence encoding either the activation domain or the DNA binding domain of the transcription activator which is not expressed by the library of tester expression vectors, and
         a target sequence encoding the target protein or peptide; and
   either the first or second population of haploid yeast cells comprises a reporter construct comprising a reporter gene whose expression is under transcriptional control of the transcription activator;

(b) expressing the tester fusion proteins from the library of tester expression vectors and the target fusion protein from the target expression vector;

(c) selecting those yeast clones in which the reporter gene is expressed, the expression of the reporter gene being activated by binding of the tester fusion protein to the target fusion protein;

(d) Isolating the tester expression vector from the selected yeast clones;

(f) mutagenizing the first and second nucleotide sequences in the isolated tester expression vectors to form a library of mutagenized expression vectors;

(g) transforming the library of mutagenized expression vectors into the yeast cells of step (a), (h) transforming the target expression vector of step (b) into the yeast cells simultaneously or sequentially with the library of mutagenized expression vectors;

(i) expressing the target fusion protein from the target expression vector; and (j) selecting those yeast clones in which the reporter gene is expressed, the expression of the reporter gene being activated by binding of the tester fusion protein to the target fusion protein.

23. The method of claim 22, wherein the mutagenesis is selected from the group consisting of error-prone PCR mutagenesis, site-directed mutagenesis, DNA shuffling and combinations thereof.

24. The method of claim 22, wherein the haploid yeast cells of opposite mating types are α and a type strains of yeast.

25. A method for selecting single chain antibodies capable of binding to a human growth factor receptor, comprising:

(a) causing mating between a first and a second population of haploid yeast cells of opposite mating types,
   the first population of haploid yeast cells comprising
      a library of tester expression vectors for a library of tester fusion proteins having a diversity of at least $1 \times 10^7$, each tester expression vector comprising
         a first transcription sequence encoding either the activation domain or the DNA binding domain of a transcription activator, and
         a tester protein sequence comprising a first nucleotide sequence encoding an antibody heavy chain variable region, a second nucleotide sequence encoding an antibody light chain variable region, and a linker sequence encoding a linker peptide that links the antibody heavy chain and light chain variable regions,
   the second population of haploid yeast cells comprising
      a target expression vector comprising
         a second transcription sequence encoding either the activation domain or the DNA binding domain of the transcription activator which is not expressed by the library of tester expression vectors, and
         a target sequence encoding a human growth factor receptor; and
   either the first or second population of haploid yeast cells comprises a reporter construct comprising a reporter gene whose expression is under transcriptional control of the transcription activator;

(b) expressing the tester fusion proteins from the library of tester expression vectors and the target fusion protein from the target expression vector; and (c) selecting those yeast clones in which the reporter gene is expressed, the expression of the reporter gene being activated by binding of the tester fusion protein to the target fusion protein.

26. The method of claim 25, wherein the haploid yeast cells of opposite mating types are $\alpha$ and a type strains of yeast.

* * * * *